(12) United States Patent
Seidel et al.

(10) Patent No.: US 7,771,921 B2
(45) Date of Patent: *Aug. 10, 2010

(54) SEPARATION SYSTEMS OF FROZEN-THAWED SPERMATOZOA INTO X-CHROMOSOME BEARING AND Y-CHROMOSOME BEARING POPULATIONS

(75) Inventors: George E. Seidel, LaPorte, CO (US); Kehuan Lu, Guangxi (CN); Tae Kwang Suh, Fort Collins, CO (US); David G. Cran, Aberdeen (GB)

(73) Assignee: XY, LLC, Navasota, TX (US)

( * ) Notice: Subject to any disclaimer, the term of this patent is extended or adjusted under 35 U.S.C. 154(b) by 267 days.

This patent is subject to a terminal disclaimer.

(21) Appl. No.: 11/536,576

(22) Filed: Sep. 28, 2006

(65) Prior Publication Data

US 2007/0042342 A1    Feb. 22, 2007

Related U.S. Application Data

(63) Continuation of application No. 10/433,183, filed as application No. PCT/US01/45023 on Nov. 29, 2001.

(60) Provisional application No. 60/253,787, filed on Nov. 29, 2000, provisional application No. 60/253,785, filed on Nov. 29, 2000.

(51) Int. Cl.
*A01N 1/02*    (2006.01)
*C12Q 1/68*    (2006.01)

(52) U.S. Cl. .............................. 435/2; 435/6
(58) Field of Classification Search .................. None
See application file for complete search history.

(56) References Cited

U.S. PATENT DOCUMENTS

| | | | |
|---|---|---|---|
| 32,350 A | 5/1861 | Bhattacharya |
| 34,782 A | 3/1862 | Dandliker et al. |
| 3,005,756 A | 10/1961 | VanDemark et al. |
| 3,299,354 A | 1/1967 | Hogg |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister |
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter et al. |
| 3,791,517 A | 2/1974 | Friedman |
| 3,810,010 A | 5/1974 | Thorn |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,906,929 A | 9/1975 | Augspurger |
| 3,909,744 A | 9/1975 | Wisner et al. |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| RE29,141 E | 2/1977 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |

(Continued)

FOREIGN PATENT DOCUMENTS

BR    9704313    6/1999

(Continued)

OTHER PUBLICATIONS

Weigel, K. A., Exploring the Role of Sexed Semen in Diary Production Systems; J. Dairy Sci. 87: (E.Suppl.): E120-E130; 2004 American Dairy Science Assoc.

(Continued)

*Primary Examiner*—Rebecca E. Prouty
*Assistant Examiner*—Paul C. Martin
(74) *Attorney, Agent, or Firm*—Cindee Ewell; Ryan Christensen

(57) ABSTRACT

Devices, compositions, and methods for handling, separating, packaging, and utilization of spermatozoa (1) that can be derived from previously frozen sperm samples collected from a male mammal. Specifically, techniques to uniformly stain (2) spermatozoal DNA even when derived from previously frozen sperm and separation techniques to separate and isolate spermatozoa even when derived from previously frozen sperm samples into X-chromosome bearing and Y-chromosome bearing populations having high purity.

20 Claims, 3 Drawing Sheets

U.S. PATENT DOCUMENTS

| | | |
|---|---|---|
| 4,092,229 A | 5/1978 | Bhattacharya |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |
| 4,225,405 A | 9/1980 | Lawson |
| 4,230,558 A | 10/1980 | Fulwyler |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junilla |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,989,977 A | 2/1991 | North, Jr. |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | Grooth et al. |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |
| 5,138,181 A | 8/1992 | Lefevre et al. |
| 5,142,140 A | 8/1992 | Yamazaki et al. |
| 5,142,462 A | 8/1992 | Kashima |

| | | | | | |
|---|---|---|---|---|---|
| 5,144,224 A | 9/1992 | Larsen | 5,601,533 A | 2/1997 | Hancke et al. |
| 5,150,313 A | 9/1992 | Van den Engh et al. | 5,602,039 A | 2/1997 | Van den Engh |
| 5,158,889 A | 10/1992 | Hirako et al. | 5,602,349 A | 2/1997 | Van den Engh |
| 5,159,397 A | 10/1992 | Kosaka et al. | 5,608,519 A | 3/1997 | Gourley et al. |
| 5,159,403 A | 10/1992 | Kosaka | 5,620,842 A | 4/1997 | Davis et al. |
| 5,162,306 A | 11/1992 | Donaldson | 5,622,820 A | 4/1997 | Rossi |
| 5,167,926 A | 12/1992 | Kimura et al. | 5,627,037 A | 5/1997 | Ward et al. |
| 5,180,065 A | 1/1993 | Touge et al. | 5,633,503 A | 5/1997 | Kosaka |
| 5,182,617 A | 1/1993 | Yoneyama et al. | 5,641,457 A | 6/1997 | Vardanega |
| 5,195,979 A | 3/1993 | Schinkel et al. | 5,643,796 A | 7/1997 | den Engh et al. |
| 5,199,576 A | 4/1993 | Corio et al. | 5,650,847 A | 7/1997 | Maltsev et al. |
| 5,204,884 A | 4/1993 | Leary et al. | 5,658,751 A | 8/1997 | Yue et al. |
| 5,215,376 A | 6/1993 | Schulte et al. | 5,660,997 A | 8/1997 | Spaulding |
| 5,219,729 A | 6/1993 | Hodgen | 5,663,048 A | 9/1997 | Winkfein et al. |
| 5,247,339 A | 9/1993 | Ogino | 5,665,315 A | 9/1997 | Robert et al. |
| 5,259,593 A | 11/1993 | Orme et al. | 5,672,880 A | 9/1997 | Kain |
| 5,260,764 A | 11/1993 | Fukuda et al. | 5,674,743 A | 10/1997 | Ulmer |
| 5,274,240 A | 12/1993 | Mathies et al. | 5,675,401 A | 10/1997 | Wangler et al. |
| 5,275,787 A | 1/1994 | Yuguchi et al. | 5,682,038 A | 10/1997 | Hoffman |
| 5,298,967 A | 3/1994 | Wells | 5,684,575 A | 11/1997 | Steen |
| 5,315,122 A | 5/1994 | Pinsky et al. | 5,687,727 A | 11/1997 | Kraus et al. |
| 5,316,540 A | 5/1994 | McMannis et al. | 5,690,815 A | 11/1997 | Krasnoff et al. |
| 5,317,162 A | 5/1994 | Pinsky et al. | 5,690,895 A | 11/1997 | Matsumoto et al. |
| 5,346,990 A | 9/1994 | Spaulding | 5,691,133 A | 11/1997 | Critser et al. |
| 5,359,907 A | 11/1994 | Baker et al. | 5,693,534 A | 12/1997 | Alak et al. |
| 5,366,888 A | 11/1994 | Fry et al. | 5,696,157 A | 12/1997 | Wang et al. |
| 5,367,474 A | 11/1994 | Auer et al. | 5,700,692 A | 12/1997 | Sweet |
| 5,370,842 A | 12/1994 | Miyazaki et al. | 5,701,012 A | 12/1997 | Ho |
| 5,371,585 A | 12/1994 | Morgan et al. | 5,707,808 A | 1/1998 | Roslaniec et al. |
| 5,395,588 A | 3/1995 | North, Jr. et al. | 5,708,868 A | 1/1998 | Ishikawa |
| 5,400,179 A | 3/1995 | Ito | 5,712,807 A | 1/1998 | Bangham |
| 5,412,466 A | 5/1995 | Ogino | 5,719,666 A | 2/1998 | Fukuda et al. |
| 5,437,987 A | 8/1995 | Ten et al. | 5,719,667 A | 2/1998 | Miers |
| 5,439,362 A | 8/1995 | Spaulding | 5,726,009 A | 3/1998 | Connors et al. |
| 5,444,527 A | 8/1995 | Kosaka | 5,726,364 A | 3/1998 | Van den Engh |
| 5,447,841 A | 9/1995 | Grey et al. | 5,726,751 A | 3/1998 | Altendorf et al. |
| 5,447,842 A | 9/1995 | Simons | 5,730,941 A | 3/1998 | Lefevre et al. |
| 5,452,054 A | 9/1995 | Dewa et al. | 5,736,330 A | 4/1998 | Fulton |
| 5,457,526 A | 10/1995 | Kosaka | 5,739,902 A | 4/1998 | Gjelsnes et al. |
| 5,461,145 A | 10/1995 | Kudo et al. | 5,745,308 A | 4/1998 | Spangenberg |
| 5,464,581 A | 11/1995 | van den Engh | 5,747,349 A | 5/1998 | den Engh et al. |
| 5,466,572 A | 11/1995 | Sasaki et al. | 5,759,767 A | 6/1998 | Lakowicz et al. |
| 5,467,189 A | 11/1995 | Kreikebaum et al. | 5,777,732 A | 7/1998 | Hanninen et al. |
| 5,469,375 A | 11/1995 | Kosaka | 5,780,230 A | 7/1998 | Li et al. |
| 5,471,294 A | 11/1995 | Ogino | 5,786,560 A | 7/1998 | Tatah et al. |
| 5,471,299 A | 11/1995 | Kaye et al. | 5,790,692 A | 8/1998 | Price et al. |
| 5,475,487 A | 12/1995 | Mariella, Jr. et al. | 5,793,485 A | 8/1998 | Gourley |
| 5,480,774 A | 1/1996 | Hew et al. | 5,796,112 A | 8/1998 | Ichie |
| 5,480,775 A | 1/1996 | Ito et al. | 5,798,276 A | 8/1998 | Haugland et al. |
| 5,483,469 A | 1/1996 | Van den Engh et al. | 5,799,830 A | 9/1998 | Carroll et al. |
| 5,488,469 A | 1/1996 | Yamamoto et al. | 5,804,436 A | 9/1998 | Okun et al. |
| 5,492,534 A | 2/1996 | Atheyde et al. | 5,815,262 A | 9/1998 | Schrof et al. |
| 5,494,795 A | 2/1996 | Guerry et al. | 5,819,948 A | 10/1998 | Van den Engh |
| 5,495,719 A | 3/1996 | Gray, Jr. | 5,824,269 A | 10/1998 | Kosaka et al. |
| 5,496,272 A | 3/1996 | Chung et al. | 5,831,723 A | 11/1998 | Kubota et al. |
| 5,503,994 A | 4/1996 | Shear et al. | 5,835,262 A | 11/1998 | Iketaki et al. |
| 5,514,537 A | 5/1996 | Chandler | 5,840,504 A | 11/1998 | Blecher |
| 5,523,573 A | 6/1996 | Hanninen et al. | 5,844,685 A | 12/1998 | Gontin |
| 5,532,155 A | 7/1996 | Ranoux | 5,846,737 A | 12/1998 | Kang |
| 5,547,849 A | 8/1996 | Baer et al. | 5,866,344 A | 2/1999 | Georgiou |
| 5,548,395 A | 8/1996 | Kosaka | 5,868,767 A | 2/1999 | Farley et al. |
| 5,548,661 A | 8/1996 | Price et al. | 5,872,627 A | 2/1999 | Miers |
| 5,550,058 A | 8/1996 | Corio et al. | 5,873,254 A | 2/1999 | Arav |
| 5,556,764 A | 9/1996 | Sizto et al. | 5,874,266 A | 2/1999 | Paisson |
| 5,558,998 A | 9/1996 | Hammond et al. | 5,876,942 A | 3/1999 | Cheng et al. |
| 5,559,032 A | 9/1996 | Pomeroy et al. | 5,880,457 A | 3/1999 | Tomiyama et al. |
| 5,578,449 A | 11/1996 | Frasch et al. | 5,880,474 A | 3/1999 | Norton et al. |
| 5,579,159 A | 11/1996 | Ito | 5,883,378 A | 3/1999 | Irish et al. |
| 5,584,982 A | 12/1996 | Dovichi et al. | 5,888,730 A | 3/1999 | Gray et al. |
| 5,589,457 A | 12/1996 | Wiltbank | 5,891,734 A | 4/1999 | Gill et al. |
| 5,596,401 A | 1/1997 | Kusuzawa | 5,893,843 A | 4/1999 | Rodrigues Claro |
| 5,601,234 A | 2/1997 | Larue | 5,895,764 A | 4/1999 | Sklar et al. |
| 5,601,235 A | 2/1997 | Booker et al. | 5,895,922 A | 4/1999 | Ho |

| | | |
|---|---|---|
| 6,704,313 B1 | 4/1999 | De Resende et al. |
| 5,899,848 A | 5/1999 | Haubrich |
| 5,909,278 A | 6/1999 | Deka et al. |
| 5,912,257 A | 6/1999 | Prasad et al. |
| 5,916,144 A | 6/1999 | Prather et al. |
| 5,916,449 A | 6/1999 | Ellwart et al. |
| 5,917,733 A | 6/1999 | Bangham |
| 5,919,360 A | 7/1999 | Contaxis, III et al. |
| 5,919,621 A | 7/1999 | Brown |
| 5,934,885 A | 8/1999 | Farrell et al. |
| 5,962,238 A | 10/1999 | Sizto et al. |
| 5,972,710 A | 10/1999 | Weigl et al. |
| 5,973,842 A | 10/1999 | Spangenberg |
| 5,985,216 A | 11/1999 | Rens et al. |
| 5,985,538 A | 11/1999 | Stachecju |
| 5,990,479 A | 11/1999 | Weiss et al. |
| 5,991,028 A | 11/1999 | Cabib et al. |
| 5,998,140 A | 12/1999 | Dervan et al. |
| 5,998,212 A | 12/1999 | Corio et al. |
| 6,002,471 A | 12/1999 | Quake |
| 6,003,678 A | 12/1999 | Van den Engh |
| 6,042,249 A | 3/2000 | Spangenberg |
| 6,050,935 A | 4/2000 | Ranoux et al. |
| 6,071,689 A | 6/2000 | Seidel et al. |
| 6,079,836 A | 6/2000 | Burr et al. |
| 6,086,574 A | 7/2000 | Carroll et al. |
| 6,087,352 A | 7/2000 | Trout |
| 6,090,947 A | 7/2000 | Dervan et al. |
| 6,097,485 A | 8/2000 | Lievan |
| 6,111,398 A | 8/2000 | Graham |
| 6,117,068 A | 9/2000 | Gourley et al. |
| 6,119,465 A | 9/2000 | Mullens et al. |
| 6,120,735 A | 9/2000 | Zborowski et al. |
| 6,128,133 A | 10/2000 | Bergmann |
| 6,130,034 A | 10/2000 | Aitken |
| 6,132,961 A | 10/2000 | Gray et al. |
| 6,133,044 A | 10/2000 | Van den Engh |
| 6,133,995 A | 10/2000 | Kubota |
| 6,139,800 A | 10/2000 | Chandler |
| 6,140,121 A | 10/2000 | Ellington et al. |
| 6,143,535 A | 11/2000 | Paisson |
| 6,143,901 A | 11/2000 | Dervan |
| 6,146,837 A | 11/2000 | van de Winkel |
| 6,149,867 A | 11/2000 | Seidel et al. |
| 6,153,373 A | 11/2000 | Benjamin et al. |
| 6,154,276 A | 11/2000 | Mariella, Jr. |
| 6,175,409 B1 | 1/2001 | Nielsen et al. |
| 6,177,277 B1 | 1/2001 | Soini |
| 6,193,647 B1 | 2/2001 | Beebe et al. |
| 6,201,628 B1 | 3/2001 | Basiji et al. |
| 6,207,392 B1 | 3/2001 | Weiss et al. |
| 6,208,411 B1 | 3/2001 | Vaez-Iravani |
| 6,211,477 B1 | 4/2001 | Cardott et al. |
| 6,214,560 B1 | 4/2001 | Yguerabide et al. |
| 6,221,654 B1 | 4/2001 | Quake et al. |
| 6,221,671 B1 | 4/2001 | Groner et al. |
| 6,238,920 B1 | 5/2001 | Nagai et al. |
| 6,247,323 B1 | 6/2001 | Maeda |
| 6,248,590 B1 | 6/2001 | Malachowski |
| 6,256,096 B1 | 7/2001 | Johnson |
| 6,263,745 B1 | 7/2001 | Buchanan et al. |
| 6,283,920 B1 | 9/2001 | Eberle et al. |
| 6,296,810 B1 | 10/2001 | Ulmer |
| 6,309,815 B1 | 10/2001 | Tash et al. |
| 6,316,234 B1 | 11/2001 | Bova |
| 6,317,511 B1 | 11/2001 | Horiuchi |
| 6,322,901 B1 | 11/2001 | Bawendi et al. |
| 6,323,632 B1 | 11/2001 | Husher et al. |
| 6,326,144 B1 | 12/2001 | Bawendi et al. |
| 6,328,071 B1 | 12/2001 | Austin |
| 6,329,158 B1 | 12/2001 | Hoffman et al. |
| 6,332,540 B1 | 12/2001 | Paul et al. |
| 6,357,307 B2 | 3/2002 | Buchanan et al. |
| 6,368,786 B1 | 4/2002 | Saint-Ramon et al. |
| 6,372,422 B1 | 4/2002 | Seidel et al. |
| 6,372,506 B1 | 4/2002 | Norton |
| 6,384,951 B1 | 5/2002 | Basiji et al. |
| 6,395,305 B1 | 5/2002 | Buhr et al. |
| 6,400,453 B1 | 6/2002 | Hansen |
| 6,411,835 B1 | 6/2002 | Modell et al. |
| 6,411,904 B1 | 6/2002 | Chandler |
| 6,416,190 B1 | 7/2002 | Grier et al. |
| 6,423,505 B1 | 7/2002 | Davis |
| 6,423,551 B1 | 7/2002 | Weiss et al. |
| 6,432,630 B1 | 8/2002 | Blankenstein |
| 6,432,638 B2 | 8/2002 | Dervan et al. |
| 6,452,372 B1 | 9/2002 | Husher et al. |
| 6,454,945 B1 | 9/2002 | Weigl et al. |
| 6,456,055 B2 | 9/2002 | Shinabe et al. |
| 6,463,314 B1 | 10/2002 | Haruna |
| 6,465,169 B2 | 10/2002 | Walderich et al. |
| 6,473,176 B2 | 10/2002 | Basiji et al. |
| 6,482,652 B2 | 11/2002 | Furlong et al. |
| 6,489,092 B1 | 12/2002 | Benjamin et al. |
| 6,495,333 B1 | 12/2002 | Willmann et al. |
| 6,495,366 B1 | 12/2002 | Briggs |
| 6,503,698 B1 | 1/2003 | Dobrinsky et al. |
| 6,511,853 B1 | 1/2003 | Kopf-Sill et al. |
| 6,514,722 B2 | 2/2003 | Paisson et al. |
| 6,524,860 B1 | 2/2003 | Seidel et al. |
| 6,528,802 B1 | 3/2003 | Koenig et al. |
| 6,534,308 B1 | 3/2003 | Palsson et al. |
| 6,537,829 B1 | 3/2003 | Zarling et al. |
| 6,540,895 B1 | 4/2003 | Spence et al. |
| 6,563,583 B2 | 5/2003 | Ortyn et al. |
| 6,576,291 B2 | 6/2003 | Bawendi et al. |
| 6,577,387 B2 | 6/2003 | Ross, III et al. |
| 6,580,504 B1 | 6/2003 | Ortyn et al. |
| 6,587,203 B2 | 7/2003 | Colon |
| 6,589,792 B1 | 7/2003 | Malachowski |
| 6,590,911 B1 | 7/2003 | Spinelli et al. |
| 6,596,143 B1 | 7/2003 | Wang et al. |
| 6,596,499 B2 | 7/2003 | Jalink |
| 6,604,435 B2 | 8/2003 | Buchanan et al. |
| 6,613,525 B2 | 9/2003 | Nelson et al. |
| 6,617,107 B1 | 9/2003 | Dean |
| 6,618,143 B2 | 9/2003 | Roche et al. |
| 6,618,679 B2 | 9/2003 | Loehrlein et al. |
| 6,641,708 B1 | 11/2003 | Becker et al. |
| 6,642,018 B1 | 11/2003 | Koller et al. |
| 6,658,357 B2 | 12/2003 | Chandler |
| 6,664,550 B2 | 12/2003 | Rader et al. |
| 6,667,830 B1 | 12/2003 | Iketaki et al. |
| 6,671,044 B2 | 12/2003 | Ortyn et al. |
| 6,673,095 B2 | 1/2004 | Nordquist |
| 6,674,525 B2 | 1/2004 | Bardell et al. |
| 6,698,627 B2 | 3/2004 | Garcia et al. |
| 6,700,130 B2 | 3/2004 | Fritz |
| 6,703,621 B2 | 3/2004 | Wolleschensky |
| 6,706,163 B2 | 3/2004 | Seul et al. |
| 6,707,555 B1 | 3/2004 | Kusuzawa et al. |
| 6,713,019 B2 | 3/2004 | Ozasa et al. |
| 6,729,369 B2 | 5/2004 | Neas et al. |
| 6,746,873 B1 | 6/2004 | Buchanan et al. |
| 6,752,298 B2 | 6/2004 | Garcia et al. |
| 6,753,161 B2 | 6/2004 | Koller et al. |
| 6,761,286 B2 | 7/2004 | Py et al. |
| 6,761,288 B2 | 7/2004 | Garcia |
| 6,767,706 B2 | 7/2004 | Quake |
| 6,780,377 B2 | 8/2004 | Hall et al. |
| 6,782,768 B2 | 8/2004 | Buchanan et al. |
| 6,789,706 B2 | 9/2004 | Abergel et al. |
| 6,789,750 B1 | 9/2004 | Heldt |
| 6,793,387 B1 | 9/2004 | Neas et al. |
| 6,813,017 B1 | 11/2004 | Hoffman et al. |
| 6,819,411 B1 | 11/2004 | Sharpe et al. |

| | | |
|---|---|---|
| 6,849,394 B2 | 2/2005 | Rozeboom et al. |
| 6,849,423 B2 | 2/2005 | Mutz et al. |
| 6,861,265 B1 | 3/2005 | Van den Engh |
| 6,941,005 B2 | 9/2005 | Lary et al. |
| 7,015,310 B2 | 3/2006 | Remington et al. |
| 7,094,527 B2 | 8/2006 | Seidel et al. |
| 7,105,355 B2 | 9/2006 | Kurabayashi et al. |
| 7,195,920 B2 | 3/2007 | Seidel et al. |
| 7,208,265 B1 | 4/2007 | Schenk |
| 7,221,453 B2 | 5/2007 | Sharpe et al. |
| 2001/0006416 A1 | 7/2001 | Johnson |
| 2002/0047697 A1 | 4/2002 | Husher et al. |
| 2002/0058332 A1 | 5/2002 | Quake et al. |
| 2002/0064809 A1 | 5/2002 | Mutz et al. |
| 2002/0096123 A1 | 7/2002 | Whittier et al. |
| 2002/0113965 A1 | 8/2002 | Roche et al. |
| 2002/0115055 A1 | 8/2002 | Matta |
| 2002/0119558 A1 | 8/2002 | Seidel et al. |
| 2002/0131957 A1 | 9/2002 | Gavin |
| 2002/0141902 A1 | 10/2002 | Ozasa et al. |
| 2002/0171827 A1 | 11/2002 | Van den Engh |
| 2002/0182590 A1 | 12/2002 | Strange et al. |
| 2002/0186375 A1 | 12/2002 | Asbury et al. |
| 2002/0186874 A1 | 12/2002 | Price et al. |
| 2002/0198928 A1 | 12/2002 | Bukshpan et al. |
| 2003/0048433 A1 | 3/2003 | Desjonqueres |
| 2003/0059764 A1 | 3/2003 | Ravkin et al. |
| 2003/0059945 A1 | 3/2003 | Dzekunov et al. |
| 2003/0078703 A1 | 4/2003 | Potts |
| 2003/0096405 A1 | 5/2003 | Takayama et al. |
| 2003/0098421 A1 | 5/2003 | Ho |
| 2003/0113765 A1 | 6/2003 | Dempcy et al. |
| 2003/0119050 A1 | 6/2003 | Shai |
| 2003/0119206 A1 | 6/2003 | Shai |
| 2003/0129091 A1 | 7/2003 | Seidel et al. |
| 2003/0157475 A1 | 8/2003 | Schenk |
| 2003/0165812 A1 | 9/2003 | Takayama et al. |
| 2003/0175917 A1 | 9/2003 | Cumming |
| 2003/0175980 A1 | 9/2003 | Hayenga et al. |
| 2003/0190681 A1 | 10/2003 | Shai |
| 2003/0207461 A1 | 11/2003 | Bell et al. |
| 2003/0209059 A1 | 11/2003 | Kawano |
| 2004/0005582 A1 | 1/2004 | Shipwast |
| 2004/0031071 A1 | 2/2004 | Morris et al. |
| 2004/0034879 A1 | 2/2004 | Rothstein et al. |
| 2004/0049801 A1 | 3/2004 | Seidel |
| 2004/0053243 A1 | 3/2004 | Evans |
| 2004/0055030 A1 | 3/2004 | Maxwell et al. |
| 2004/0061070 A1 | 4/2004 | Hansen |
| 2004/0061853 A1 | 4/2004 | Blasenheim |
| 2004/0062685 A1 | 4/2004 | Norton et al. |
| 2004/0072278 A1 | 4/2004 | Chou et al. |
| 2004/0107150 A1 | 6/2004 | Neas et al. |
| 2004/0132001 A1 | 7/2004 | Seidel et al. |
| 2005/0003472 A1 | 1/2005 | Anzar |
| 2005/0011582 A1 | 1/2005 | Haug |
| 2005/0064383 A1 | 3/2005 | Bashkin et al. |
| 2005/0112541 A1 | 5/2005 | Durack et al. |
| 2005/0214733 A1 | 9/2005 | Graham et al. |
| 2005/0244805 A1 | 11/2005 | Ludwig et al. |
| 2005/0282245 A1 | 12/2005 | Ludwig et al. |
| 2006/0118167 A1 | 6/2006 | Neas et al. |
| 2006/0147894 A1 | 7/2006 | Sowter |
| 2006/0203226 A1 | 9/2006 | Roche et al. |
| 2006/0263829 A1 | 11/2006 | Evans et al. |
| 2006/0281176 A1 | 12/2006 | Seidel et al. |
| 2007/0026378 A1 | 2/2007 | Schenk |
| 2007/0026379 A1 | 2/2007 | Seidel et al. |
| 2007/0042342 A1 | 2/2007 | Seidel et al. |
| 2007/0092860 A1 | 4/2007 | Schenk |
| 2007/0099171 A1 | 5/2007 | Schenk |
| 2007/0099260 A1 | 5/2007 | Seidel et al. |
| 2007/0117086 A1 | 5/2007 | Evans et al. |
| 2007/0123461 A1 | 5/2007 | Josephson |
| 2007/0248976 A1 | 10/2007 | Harding |

FOREIGN PATENT DOCUMENTS

| | | |
|---|---|---|
| CA | 1029833 | 4/1978 |
| CA | 1 250 808 | 3/1989 |
| CA | 2113957 A1 | 1/1994 |
| CN | ZL 03109426.0 | 12/2005 |
| EP | 0025296 A2 | 3/1981 |
| EP | 0 046 345 A2 | 2/1982 |
| EP | 0 068 404 B1 | 1/1983 |
| EP | 0071537 A1 | 2/1983 |
| EP | 0 026 770 B1 | 3/1983 |
| EP | 0 029 662 B1 | 2/1984 |
| EP | 0 025 296 B1 | 5/1985 |
| EP | 0140616 | 5/1985 |
| EP | 0 158 147 A2 | 10/1985 |
| EP | 0160201 A2 | 11/1985 |
| EP | 0189702 A1 | 8/1986 |
| EP | 0 229 814 B1 | 7/1987 |
| EP | 0 246 604 A2 | 11/1987 |
| EP | 0288029 B1 | 4/1988 |
| EP | 0276166 A2 | 7/1988 |
| EP | 0 289 677 A2 | 11/1988 |
| EP | 0 316 173 A1 | 5/1989 |
| EP | 0 317 809 A2 | 5/1989 |
| EP | A-0 366794 | 5/1990 |
| EP | 0 409 293 A2 | 1/1991 |
| EP | 0461618 | 12/1991 |
| EP | 0 463 562 A1 | 1/1992 |
| EP | 0468100 A1 | 1/1992 |
| EP | 0474 187 A2 | 3/1992 |
| EP | 0 316 172 B1 | 7/1992 |
| EP | 0 316 171 B1 | 9/1992 |
| EP | 0570102 A1 | 3/1993 |
| EP | 0538786 A | 4/1993 |
| EP | 0 279 000 B1 | 7/1993 |
| EP | 0 553 951 A1 | 8/1993 |
| EP | 0 288 029 B1 | 1/1994 |
| EP | 0 381 694 B1 | 6/1994 |
| EP | 0 361 504 B1 | 7/1994 |
| EP | 606847 A2 | 7/1994 |
| EP | 0 289 200 B2 | 8/1994 |
| EP | 0 555 212 B1 | 10/1994 |
| EP | 0 361 503 B1 | 11/1994 |
| EP | 0 696 731 A2 | 2/1996 |
| EP | 0 705 978 A2 | 4/1996 |
| EP | 0 711 991 A1 | 5/1996 |
| EP | 0 471 758 B1 | 9/1996 |
| EP | 0 736 765 A1 | 10/1996 |
| EP | 0 545 284 B1 | 2/1997 |
| EP | 0 360 487 B1 | 7/1997 |
| EP | 0 412 431 B1 | 10/1997 |
| EP | 0 526 131 B1 | 1/1998 |
| EP | A-0 478155 | 1/1998 |
| EP | 0 822 404 A3 | 2/1998 |
| EP | 0 822 401 A2 | 4/1998 |
| EP | 0 556 748 B1 | 10/1998 |
| EP | 0 430 402 B1 | 1/1999 |
| EP | 0 529 666 B1 | 4/2000 |
| EP | 0 994 342 A3 | 4/2000 |
| EP | 0 752 133 B1 | 6/2000 |
| EP | 1 018 644 A2 | 7/2000 |
| EP | 1 118 268 A1 | 7/2001 |
| EP | 1 147 774 A1 | 10/2001 |
| EP | 0 534 033 B1 | 11/2001 |
| EP | 0 925 494 B1 | 12/2001 |
| EP | 0 748 316 B1 | 5/2002 |
| EP | 0 662 124 B1 | 6/2002 |
| EP | 1 245 944 A3 | 10/2002 |
| EP | 1 249 502 A2 | 10/2002 |
| EP | 1250897 A1 | 10/2002 |

| | | | | | | |
|---|---|---|---|---|---|---|
| EP | 1 380 304 A2 | 1/2004 | | WO | WO 01/02836 A1 | 1/2001 |
| EP | 1403633 A3 | 4/2004 | | WO | WO 01/28700 A1 | 4/2001 |
| EP | 1 100 400 B1 | 5/2004 | | WO | WO 0129538 | 4/2001 |
| EP | 1 257 168 B1 | 2/2005 | | WO | WO 01/37655 A1 | 5/2001 |
| FR | 2574656 A1 | 6/1986 | | WO | WO 01/40765 A2 | 6/2001 |
| FR | A-2 635453 | 2/1990 | | WO | WO 01/40765 A3 | 6/2001 |
| FR | 2 647 668 A | 12/1990 | | WO | WO 01/42757 A2 | 6/2001 |
| FR | 2699678 A1 | 6/1994 | | WO | WO 01/51612 A1 | 7/2001 |
| GB | 1471019 | 4/1977 | | WO | WO 01/61313 A2 | 8/2001 |
| GB | 2 121 976 A | 1/1984 | | WO | WO 01/68110 | 9/2001 |
| GB | 2 122 369 A | 1/1984 | | WO | WO 01/68226 A2 | 9/2001 |
| GB | 2 125 181 A | 2/1984 | | WO | WO 01/71348 A1 | 9/2001 |
| GB | 2 136 561 A | 9/1984 | | WO | WO 01/75161 A2 | 10/2001 |
| GB | 2 137 352 A | 10/1984 | | WO | WO 0175176 | 10/2001 |
| GB | 2145112 | 2/1985 | | WO | WO 01/85913 A2 | 11/2001 |
| GB | 2 144 542 A | 3/1985 | | WO | WO 01/85913 A3 | 11/2001 |
| GB | 2 153 521 A | 8/1985 | | WO | WO 01/90295 A1 | 11/2001 |
| GB | 2 243 681 A | 11/1991 | | WO | WO 01/95815 A1 | 12/2001 |
| GB | 2 360 360 A | 9/2001 | | WO | WO 02/01189 A1 | 1/2002 |
| JP | 61139747 (A) | 6/1986 | | WO | WO 02/04666 A2 | 1/2002 |
| JP | 61159135 (A) | 7/1986 | | WO | WO 02/19594 | 3/2002 |
| JP | 2024535 | 1/1990 | | WO | WO 02/19943 A1 | 3/2002 |
| JP | 4126064 (A) | 4/1992 | | WO | WO 02/20850 A2 | 3/2002 |
| JP | 4126065 (A) | 4/1992 | | WO | WO 02/21102 A2 | 3/2002 |
| JP | 4126066 (A) | 4/1992 | | WO | WO 02/23163 A1 | 3/2002 |
| JP | 4126079 (A) | 4/1992 | | WO | WO 02/25269 A2 | 3/2002 |
| JP | 4126080 (A) | 4/1992 | | WO | WO 02/26114 A2 | 4/2002 |
| JP | 4126081 (A) | 4/1992 | | WO | WO 02/28311 A1 | 4/2002 |
| SU | 1056008 | 11/1983 | | WO | WO 02/29106 A2 | 4/2002 |
| SU | 1260778 A1 | 9/1986 | | WO | 02041906 A2 | 5/2002 |
| WO | WO 84/01265 A1 | 4/1984 | | WO | WO 02/41906 A2 | 5/2002 |
| WO | WO 85/04014 A1 | 9/1985 | | WO | WO 02/43486 A1 | 6/2002 |
| WO | WO 88/07198 | 9/1988 | | WO | WO 02/43574 A3 | 6/2002 |
| WO | WO 89/04470 A1 | 5/1989 | | WO | WO 02/44319 A2 | 6/2002 |
| WO | WO 89/04471 A1 | 5/1989 | | WO | WO 02/052244 A2 | 7/2002 |
| WO | WO 90/13315 A1 | 11/1990 | | WO | WO 02/054044 A2 | 7/2002 |
| WO | 91/05236 | 4/1991 | | WO | WO 02/057775 A1 | 7/2002 |
| WO | WO 92/08120 A1 | 5/1992 | | WO | WO 02/060880 A1 | 8/2002 |
| WO | WO 92/17288 A1 | 10/1992 | | WO | WO 02/077637 A1 | 10/2002 |
| WO | WO 93/10803 | 6/1993 | | WO | WO 02/092161 A1 | 11/2002 |
| WO | 9317322 A1 | 9/1993 | | WO | WO 02/092247 A1 | 11/2002 |
| WO | WO 94/22001 A1 | 9/1994 | | WO | WO 03/008102 A1 | 1/2003 |
| WO | WO 96/04542 A1 | 2/1996 | | WO | WO 03/008937 A2 | 1/2003 |
| WO | WO 96/12171 A2 | 4/1996 | | WO | WO 03/012403 A1 | 2/2003 |
| WO | WO 96/12172 | 4/1996 | | WO | WO 03/016875 A2 | 2/2003 |
| WO | WO 96/12173 A1 | 4/1996 | | WO | 03020877 A2 | 3/2003 |
| WO | WO 96/31764 | 10/1996 | | WO | WO 03/056330 A2 | 7/2003 |
| WO | WO 96/33806 A1 | 10/1996 | | WO | WO 03/056335 A2 | 7/2003 |
| WO | WO 97/29354 A1 | 8/1997 | | WO | WO 03/072765 A1 | 9/2003 |
| WO | WO 97/30338 A1 | 8/1997 | | WO | WO 03/078065 A1 | 9/2003 |
| WO | WO 97/35189 A1 | 9/1997 | | WO | WO 03/078972 A1 | 9/2003 |
| WO | WO 97/43620 A1 | 11/1997 | | WO | WO 04001401 | 12/2003 |
| WO | WO 89/04472 A1 | 5/1998 | | WO | WO 2004/006916 A1 | 1/2004 |
| WO | WO 98/34094 A1 | 8/1998 | | WO | WO 2004/009237 A2 | 1/2004 |
| WO | WO 98/48259 | 10/1998 | | WO | WO 2004/009237 A3 | 1/2004 |
| WO | WO 98/57152 A1 | 12/1998 | | WO | WO 2004/012837 A2 | 2/2004 |
| WO | WO 99/05504 A2 | 2/1999 | | WO | WO 2004/012837 A3 | 2/2004 |
| WO | WO 99/33956 A1 | 7/1999 | | WO | WO 2004/017041 A2 | 2/2004 |
| WO | WO 99/38883 A1 | 8/1999 | | WO | WO 2004/017041 A3 | 2/2004 |
| WO | WO 99/42810 A1 | 8/1999 | | WO | WO 2004/024227 A2 | 3/2004 |
| WO | WO 99/44035 | 9/1999 | | WO | WO 2004/024227 A3 | 3/2004 |
| WO | WO 99/44037 A1 | 9/1999 | | WO | WO 2004/046712 A2 | 6/2004 |
| WO | WO 99/47906 A1 | 9/1999 | | WO | WO 2004/059282 A2 | 7/2004 |
| WO | WO 99/60397 A1 | 11/1999 | | WO | WO 2004/003697 A2 | 10/2004 |
| WO | WO 9957955 | 11/1999 | | WO | WO 2004/087177 A1 | 10/2004 |
| WO | WO 99/61888 A2 | 12/1999 | | WO | WO 2004/088283 A2 | 10/2004 |
| WO | WO 00/06193 A1 | 2/2000 | | WO | WO 2004/104178 A2 | 12/2004 |
| WO | WO 00/12204 | 3/2000 | | WO | WO 2004/104178 A3 | 12/2004 |
| WO | WO 00/36396 | 6/2000 | | WO | WO 2005/094852 A2 | 10/2005 |
| WO | WO 00/49387 | 8/2000 | | WO | WO 2005/095590 A2 | 10/2005 |
| WO | WO 00/54026 | 9/2000 | | WO | WO 2005/095960 A1 | 10/2005 |
| WO | WO 00/56444 | 9/2000 | | WO | 2006012597 A2 | 2/2006 |
| WO | WO 00/70080 | 11/2000 | | WO | WO 2006/015056 A2 | 2/2006 |

| | | |
|---|---|---|
| WO | 2006060770 A2 | 8/2006 |
| WO | 2007/016090 A2 | 2/2007 |

OTHER PUBLICATIONS

Ferre, L., In vitro-derived embryo production with sexed and unsexed semen from different bulls; Reproduction Fertility and Development, vol. 16, Part 1/2, p. 253, 2004.
Dalton, J.C., et al., Effect of Time of Insemination on Number of Accessory Sperm, Fetilization Rate, and Embryo Quality in Nonlactating Dairy Cattle. J Dairy Sci. 84:2413-2418, (2001).
Dransfield, M.B.G., et al., Timing of Inseminatio for Dairy Cows Identified in Estrus by a Radiotelemetric Etrus Detection System. 1998 J Dairy Sci. 81: 1874-1882.
Maatje, K. et al. Predicting Optimal Time of Insemination in Cows that Show Visual Signs of Estrus by Estimating onset of Estrus with Pedometers, J. Dairy Science, 80 (1997).
Nebel, R.L. et al. Timing of Artificial Insemination of Dairy Cows: Fixed Time Once Daily Versus Morning and Afternoon 1994 J Dairy Sci. 77:3185-3191.
Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.
Rozeboom, K. J. et al. Late Estrus or Metestrus Insemination After Estrual Inseminations Decreases Farrowing Rate and Litter Size in Swine J. Animal Sci. 1997. 75:2323-2327.
Peeler, I. D. et al. Pregnancy Rates After Times Al of Heifers Following Removal of Intravaginal Progesterone Inserts, J. Dair Sci., 87:2868-2873; 2004.
Rath, D. Low Dose Insemination in the Sow—A Review, Reprod. Dom Anim. 37, 201-205 (2002) www.blackwell.de/synergy.
Lukaszewicz, M. et al. Attempts on freezing the Greylag (Anser anser L.) gander semen Animal Reproduction Science 80 (2004) 163-173.
Foote, R. H. et al. Sperm Numbers Inseminated in Dairy Cattle and Nonreturn Rates Revisted 1997 J Dairy Science 80:3072-3076.
Conley, H.H. et at. Intensification by Intrauterine Devices of Sperm Loss from the Sheep Uterus Biology of Reproduction 2, 401-407 (1970).
Chrenek, Peter et al. Fertilizing Capacity of Transgenic and Non-Transgenic Rabbit Spermatozoa after Heterospermic Insemination Bull Vet. Inst. Pulawy 49, 307-310, 2005.
Bakst, Murray R. Fate of Fluorescent Stained Sperm following Insemination: New Light on Ovicucal Sperm Transport and Storage in the Turkey, Biology of Reproduction, (1994).
Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.
Pursel, V. G., et al. Distribution and morphology of fresh and frozen-thawed sperm in the reproductive tract of gilts after artificial insemination; Biology of Reproduction 19, 69-76 (1978).
Rath, D., "On the Status of Sex-Specific Sperm Sorting" Review lecture ET Conference 2002, Department of Animal Production and Animal Behaviour, Mariensee, Germany.
Grossfeld, R., "Experiments to Improve the Quality of Sex-Sorted Fresh and Frozen Porcine Spermatozoa" PhD thesis of the Faculty of Agricultural Sciences, Georg-August University, Gottingen, May 2007.
de Graaf, S.P. et al., Birth of offspring of pre-determined sex after artificial insemination of frozen-thawed, sex-sorted and re-frozen-thawed ram spermatozoa, Theriogenology, 67 (2007) 391-398.
O'Brien, J.K. et al., Development fo sperm sexing and associated assisted reproductive technology for sex preselection of captive bottlenose dolphins, Reproduction Fertility and Development, 2006, 18, 319-329.
Zhang, M, et al., In vitro fertilization with flow-sorted buffalo sperm, Reproduction Fertility and Development, 2005, 18(2), 283-284, abstract only.
Schenk, J.L. et al., Insemination of cow elk with sexed frozen semen, 2003 Theriogenology 59, 514.
BD Biosciences Brochure, BD FACSCalibur Flow Cytometer, the Automated, Multicolor Flow Cytometry System, 2006.

Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.
Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.
Presicce, G.A., et al., First established pregnancies in mediterranean italian buffaloes (bubalus bubalis) following deposition of sexed spermatozoa near the utero tubal junction, Reproduction in Domestic Animals, vol. 40, No. 1, Feb. 2005 , pp. 73-75(3).
Dielemann, S.J., Superovulation in cattle: from understanding the biological mechanisms to genomics of the oocyte; $23^{rd}$ Annual Meeting A.E.T.E.—Alghero; Sep. 2007.
Hasler, J. F., Factors influencing the success of embryo transfer in cattle; $23^{rd}$ World Buiatrics Congress, Quebec, Canada Jul. 2004.
Mapletoft, R. J. et al., Superovulation in perspective, Bioniche Animal Health, Dec. 2002.
Bahr, G.F. et al., Considerations of volume, mass, DNA, and arrangement of mitochondria in the midpiece of bull spermatozoa, Experimental Cell Research 60 (1970) 338-340.
Baumber, J., et al., "The Effect of Reactive Oxygen Species on Equine Sperm Motility, Viability, Acrosomal Integrity, Mitochondrial Membrane Potential, and Membrane Lipid Peroxidation", 2000, Journal of Andrology, vol. 21 (6),pp. 895-902.
BD LSR II Flow Cytometer, BD Biosciences Clontech Discovery labware Immunocytometry systems Pharmingen Jan. 28, 2004.
Bermudez, D.et al., The immediate effect of IR, laser radiation on rat , germ, cells, was studied by cytophotometric quantification, Androligia, (1991).
Sequent Biotechnologies Inc., Welcome to the Sequent Biotechnologies Inc. website., http://www.sequentbiotech.com/ Dec. 6, 2003.
Sabuer K. et al."Effects of Angiotensin II on the Acrosome Reaction in Equine Spermatozoa" Journal of Reproduction and Fertility vol. 120, 2002 p. 135-142.
Brooks, D.E., Manipulation of Mammalian Gametes in Vitro, Biennial Report, Waite Agricultural Research Institute 1986-1989.
Bruemmer, J.E. et al., "Effect of Pyruvate on the Function of Stallion Spermatozoa Stored for up to 48 Hours", Journal of Animal Science 2002, vol. 80*1, pp. 12-18.
Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).
Chaudhry, P., et al., Casein Kinase II activity and polyamine-stimulated protein phosphorylation of cytosolic and plasma membrane protiens in bovine sperm, Archives of Biochemistry and Biophyeics vol. 271, No. 1 pp. 98-106, May 15, 1989.
Chen, Y. et al., Effects of sucrose, trehalose, hypotaurine, taurine, and blood serum on survival of frozen bull sperm, Cryobiology 30,423-431 (1993).
Chapter 16 Semen processing, storage, thawing, and handling, http://nongae.gsnu.ac.kr/~cspark/teaching/chap16.html Sep. 23, 2002.
Conover,J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).
Cressman, B.E. MD. et al., Effect of sperm dose on pregnancy rate from intrauterine insemination: a retrospective analysis, Texas Medicine, 92:74-79 (1996).
Crissman, H.A. et al., Use of DIO-C5-3 to improve hoechst 33342 uptake, resolution of DNA content, and survival of CHO cells, Experimental cell research 174: 338-396 (1988).
Graves, C.N., et al., "Metabolism of Pyruvate by Epididymal-Like Bovine Spermatozoa", 1964 Journal of Dairy Science vol. 47 (12), pp. 1407-1411.
Certified Semen Services, CSS Minimum requirements for disease control of semen produced for AI, http://www.naab-css.org/about_css/disease_control-2002.html Sep. 22, 2003.
Culling, "Handbook of Histopathological and Histochemical Techniques," 3rd Ed., Butterworths, pp. 192, (1975).
De Grooth, B. et al., Simple delay monitor for droplet sorters, Cytometry 12:469-472 (1991).

Lodge, J.R., et al., "Carbon Dioxide in Anaerobic Spermatozoan Metabolism" 1968, Journal of Dairy Science, vol. 51(1), pp. 96-103.

Delgado,N. et al., Correlation between sperm membrane destabilization by heparin and aniline blue staining as membrane integrity index, Archives of Andrology40:147-152 (1998).

Denniston, D.J. et al., "Effect of Antioxidants on the Motility and Viability of Cooled Stallion Spermatozoa", Journal Reproduction Supplement 56, 2001, pp. 121-126.

De Pauw M.C. et al. Sperm Binding to Epithelial Oviduct Explants in Bulls with Different Nonreturn Rates Investigated with a new In-Vitro Model Biology of Reproduction, 2002, vol. 67 p. 1073-1079.

Donoghue, A. et al., Effects of water- and lipid-soluble antioxidants on turkey sperm viability, membrane integrity, and motility during liquid storage, Poultry Science 76:1440-1445 (1997).

Durack, Gary; "Cell—Sorting Technology", Emerging Tools for Single-cell Analysis, Chapter 1 pp. 1-359.

Zucker, R. et al., Utility of light scatter in the Morphological analysis of sperm, Cytometry 13:39-47 (1992).

Ericsson, S. et al., Interrelationships among fluorometric analyses of spermatozoal function, classical semen quality parameters and the fertility of frozen-thawed bovine spermatozoal, Theriogenology 39:1009-1024 (1993).

Ericsson, et al. "Flow Cytometric Evaluation of Cryopreserved Bovine Spermatozoa Processed Using a New Antiobiotic Combination", Theriogenology, 1990, vol. 33(6), pp. 1211-1220.

Esteves, S. et al., Improvement in motion characteristics and acrosome status in cryopreserved human spermatozoa by swim-up processing before freezing, Human Reproduction vol. 15 No. 10 pp. 2173-2179 (2000).

Evenson, D.et al., Physiology and Management, Rapid determination on sperm cell concentration in bovine semen by flow cytometry, J Dairy Sci. 76: 86-94 (1993).

Farrell et al., "Quantification of Bull Sperm Characteristics measured by Computer-Assisted Sperm Analysis (CASA) and the Relationship of Fertility", Theriogenology, 1998, vol. 49 (4), pp. 871-879.

Fitzgerald, D., Cell sorting: An enriching Experience, The Scientist Jul. 23, 2001.

Foote, R., The history of artificial insemination: Selected notes and notables, American Society of Animal Science (2002).

Garner, D., Past, Present and future perspectives on sexing sperm, CSAS Symposium SCSA: 67-78, (2002).

Zhang, M.et al.,Development of bovine embryos after in vitro fertilization of oocytes with flow cytometrically sorted, stained and unsorted sperm from different bulls, Abstract: Theriogenology vol. 60 Issue 9,pp. 1657-1663, Dec. 2003.

Johnson, L. et al., Recent advances in sex preselection of cattle: Flow cytometric sorting of X-&Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 (1994).

Pinkel,D.et al.,Flow cytometry of mammalian sperm progress in DNA and morphology measurement, The Journal of Histochemical and Cytochemistry vol. 27 No. 1 pp. 353-358 (1979).

Fugger, E. et al., Birth of normal daughters after MicroSort sperm separation and intrauterine insemination, in-vitro fertilization, or intracytoplasmic sperm injection, http://www.microsort.net/HumRepro.htm Mar. 19, 2003.

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Salisbury; G.W., et al., Reversal by Metabolic Regulators of $CO_2$-induced Inhibition of Mammalian Spermatozoa, 1959, Proc Soc Exp Biology Med, vol. 101 (1) pp. 187-189.

Centola, G.et al., Cryopreservation of human semen. Comparison of cryopreservatives, sources of variability, and prediction of post-thaw survival. PMID: 1601749 May-Jun. 1992.

Bencic, D.C., et al., "Carbon Dioxide Reversibly Inhibits Sperm Motility and Fertilizing Ability in Steelhead (Oncorhynchus mykiss)" 2000, Fish Physiology and Biochemistry, vol. 23(4), pp. 275-281.

Boatman, D.E. et al., "Bicarbonate Carbon Dioxide Regulation of Sperm Capacitation Hyperactivated Motility and Acrosome Reactions", 1991, Biology of Reproduction vol. 44(5), pp. 806-813.

Garcia, M.A. et al., "Development of a Buffer System for Dialysis of Bovine Spermatozoa Before Freezing III.Effect of Different Inorganic and Organic Salts on Fresh and Frozen-Thawed Semen", 1989, Theriogenology, vol. 31(5),pp. 1039-1048.

Johnson, L. et al., Storage of bull semen, Animal Reproduction Science 62: 143-172 (2000).

Johnson, L. et al.,Erratum to "Storage of bull semen", Animal Reproduction Science 62: 143-172 (2000).

McNutt,T.et al., Electrophoretic gel analysis of Hoechst 33342 stained and flow cytometrically sorted bovine sperm membrane proteins, Reprod. Dom Anim.31: 703-709 (1996).

Best, T. P. et al. "Nuclear Localization of Pyrrole-Imidazole Ployamide-Flourescein Conjugates in Cell Culture", PNAS, 2003, vol. 100(21), pp. 12063-12068.

Gygi, M.P., et al. "Use of Fluorescent Sequence-Specific Polyamides to Discriminate Human Chromosomes by Microscopy and Flow Cytometry", Nuci Acids Res. 2002, vol. 30(13),pp. 2790-2799.

BD Biosciences, BD AccuDrop Potion, www.bdbiosciences.com, Sep. 2002.

Agarwal, A.et al., Filtration of spermatozoa through L4 membrane:a new method, Fertility and Sterility, vol. 06, No. 6, Dec. 1991.

Anzar, M.et al., Optimizing and Quantifing fusion of liposomes to mammalian sperm using resonance energy transfer and flow cytometric methods, Cytometry49:22-27 (2002).

Anzar, M.et al., Sperm Apoptosis in fresh and cryopreserved bull semen detected by flow cytometry and it's relationship with fertility, Biology of Reproduction 66: 354-360 (2002).

Arav, A.et al., New trends in gamete's cryopreservation, Molecular and Cellular Endocrinology 187:77-81 (2002).

Arndt-Jovin et al., "Analysis and Sorting of Living Cells According to Deoxyribonucleic Acid Content", Journal Histochem. And Cytochem., 1977, vol. 25(7), pp. 585-589.

Arts,E.et al.,Evidence for the existence of lipid-diffusion barriers in the equatorial segment of human spermatozoa, Boichem J.384:211-218 (1994).

Garner,D.et al., Spermatozoa and Seminal Plasma, Reproduction in farm animals 7th edition, (2000).

Gadella B,et al., Dynamics in the membrain organization of the mammalian sperm cell and functionality in fertilization, Vet Quart. 21:142-146 (1999).

Garner, D.et al., Chromatin stability in sex-sorted sperm, VII International Congress of Andrology, (2003).

Garner, D. et al., Morphological and ultrastructural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm, Theriogenology, vol. 57 No. 1, 1-810 (2002).

Garner, D. et al., Assessment of spermatozoal function using dual fluorescent staining and flow cytometric analyses, Biology of Reproduction 34:, 127-138 (1986).

Gebhard D., Sorting Viability . . . one more time, http://www.cyto.purdue.edu/hmarchiv/1998/2263.htm Feb. 14, 2004.

Givan,A., Flow Cytometry First Principles, (1992).

Gledhill, B.et al., Identifying and separating X- and Y- Chromosome-bearing mammalian sperm by flow cytometry, Lawrence Livermore National Laboratory, Feb. 8, 1984.

Gledhill, B.et al., Flow microflurometric analysis of sperm DNA contemt: Effect of cell shape on the fluorescence distribution, J. Cell Physiol.87: 367-378.

Gledhill, B.et al., Flow cytometry and sorting of sperm and male germ cells, Flow Cytometry and sorting, second edition, pp. 531-551 (1990).

Gordon et al., "Genetic transformation of Mouse Embryos by Microinjection of Purified DNA", Proc. Natil Acad. Sci., 1980, vol. 77 (12), pp. 7380-7384.

Graham, J.et al.,Analysis of sperm cell viability, Acrosomal integrity, and Mitocondrial function using flow cytometry, Biology of Reproduction 43: 55-64 (1990).

Graham, J.et al., Effect of some Zwitter Ion buffers on freezing and storage of spermatozoa I, Bull, J. Dairy Sci 55: 372-378 (1992).

Grogan, W. et al., DNA Analysis and sorting of viable mouse testis cells, The Journal of Histochemistry and Cytochemistry, vol. 29 No. 6 pp. 738-746, (1981).

Guthrie, et al., "Flow Cytometric Sperm Sorting: Effects of Varying laser Power on Embryo Development in Swine", Mol. Reprod. And Develop., 2002,vol. 61 (1), pp. 87-92.

Hacker-Klom, U.B., et al., Effect of doxorubicin and 4'-epi-doxorubicin on mouse spermatogenesis. Mutation Research International Journal on Mutagenesis vol. 159, pp. 39-46. 1986.

Hasler, J., Symposium: Reproductive Technology and Genetic improvementJ. Dairy Sci. 75:2857-2879 (1992).

Held, A.et al., Quasi- CW Solid-state lasers Expand their reach, Photonics Spectra, Dec. 2002.

Hinkley, R.et al., Rapid visual detection of sperm-egg fusion using the DNA-Specific Fluorochrome Hoechst 33342, Developmental Biology 118: 148-154 (1986).

Januskauskas, A.et al.,Assessment of sperm quality through Fluorometry and sperm chromatin structure assay in relation to field fertility of frozen-thawed semen from Swedish Al bulls, Theriogenology 55: 947-961 (2001).

Jayendran, R.et al., Effect of glycerol and cryopreservation on oocyte penetration by human spermatozoa, PMID: 4025843, Jul. 6, 2006, abstract only.

Johnson, L., A flow cytometric/ sorting method for sexing mammalian sperm validated by DNA analysis and live births, Cytometry, p. 42 of supplement, Sep. 4, 1990.

Zhang,M. et al., Development of bovine embryos after in vitro fertilzation of oocytes with a flow cytometrically sorted, stained and unsorted sperm from different bulls, Theriogenology 60: 1657-1663 (2003).

Johnson, M., The Macromolecular Organization of membranes and its bearing on events leading up to Fertilization, Journal of Reproduction and Fertility (1975).

Kachel, V.et al., Uniform Lateral Orentation, caused by flow forces, of flat particles in flow-through systrms, The Journal of Histochemistry and Cytochemistry, vol. 25 No. 7 pp. 774-780 (1977).

Keeler, K.et al., Flow microfluorometric analysis of living spermatozoa stained with Hoechst 33342, J. Reprod.Fert. 68:205-212 (1983).

Keij, J.et al., High speed Photodamage cell sorting: An evaluation of the Zapper Prototype, Methods in cell Biology vol. 42, (1994).

Kirchhoff, C.et al., The Molecular biology of the sperm surface:Post-Testicular Membrane Remodelling, The Fate of the Male Germ Cell, (1997).

Krueger, C.et al.,Low dose Insemination in syncrhonized gilts, Theriogenology 52: 1363-1373 (1999).

Lahdetie,J.,Induction and survival of micronuclei in rat spermatids. Comparison of two meiotic micronucleus techniques using cyclophosphamide, Mutation Research, 203:47-53 (1988).

Laser Innovations—Applications, http://www.laserinnovations.com/488nm.htm Feb. 2, 2004.

Libbus, B.et al.,Incidence of chromosome aberrations in mammalian sperm stained with Hoechst 33342 and UV-laser irradiated during flow sorting, Mutation Research, 182: 265-274 (1987).

Loken, M., Separation of viable T and B lymphocytes using a cytochemical stained, Hoechst 33342, The Journal of Histochemistry and Cytochemistry,vol. 28, No. 1, pp. 36-39 (1980).

Lucas, J.et al., Orientation measurments of microsphere doublets and metaphase chromosomes in flow, Cytometry 7:575-581 (1986).

Luttmer, S.et al.,Examination of living and fixed gametes and early embryos stained with supravital fluorochromes (Hoechst 33342 and 3,3'-dihexyloxacarocyanine Iodide), Gamete Research 15:267-283 (1986).

Maxwell, W.et al.,Physiology of spermatozoa at high dilution rates:The influence of seminal plasma, Theriogenology 52: 1353-1362 (1999).

Mazur, P., The role of Intracellular freezing in the death of cells cooled at supraoptimal rates, Cryobiology 14:251-272 (1977).

McSweeney,K.et al., Abstract: Insemination of lactating holstein cows with sexed frozen/thawed sperm, http://www.cvmbs.colostate.edu/physio/abstract/ges12.html Mar. 16, 2004.

Medeiros,C. et al., Current status of sperm cryopreservation: Why isn't it better? Theriogenology 57: 327-344 (2002).

Meistrich, M., Potential and limitations of physical methods for separation of sperm bearing an X- or Y- chromosome.

Meistrich, M.et al., "cytogenetic" studies of spermatids of mice carrying Cattanach's translocation by flow cytometry, Chromosoma 74:141-151 (1979).

Morrell, J. et al., Offspring from inseminations with mammalian sperm stained with Hoechst 33342, either with or without flow cytometry, Mutation Research 224:177-183 (1989).

Morrell et al., "Sexing of Sperm by Flow Cytometry", The Veterinary Record, 1988, pp. 322-324.

Morrier, A.et al., Glycerol addition and conservation of fresh and crypreserved ram spermatozoa, Canadian Journal of AnimalScience, Sep. 2002http://pubs.nrc-cnrc.gc.ca/aic-journals/2002ab/cjas02/sep02/cjas01-045.html.

Moruzzi, J., Selecting a mammalian species for the separationof X- and Y- chromosome-bearing spermatozoa, J. Reprod. Fert. 57:319-323 (1979).

Studt, T., MEMS-based Cell Sorter Speeds Clinical Studies, R& D Magazine, Dec. 2003: pp. 36-37 as currently presented on and printed from http://www.rdmag.com 2 pgs.

R&D Technologies & Strategies for Research & Development pp. 2 www.rdmag.com printed Feb. 17, 2007.

Gwo-Bin, L.et al., Multi-cell-line micro flow cytometers with buried SU-8/SOG Optical waveguides, Feb. 2002.

Shapiro, H. M. et al., Multistation Multprameter Flow Cytometry: Some Influences of Instrumental Factors on System Performance, 1983,pp. 11-19,4, Cytometry.

OcanaQuero, J.et al., Biological effects of helium-neon irradiation on acrosome reaction in bull, Scisearch Journal of Photochemistry and Photobiology, vol. 40 No. 3, pp. 294-298 (1997), abstract only.

Pangawkar, G. et al., Physical and biochemical characteristics of semen in relation to fertility of Holstein-Friesian bulls, Indian vet. Med.J. vol. 13:21-26 (1989).

Papa, S. et al., Chromatin organization in Isolated nuclei: Flow cytometric characterization employing forward and perpendicular light scatter, Cell Biochemistry and Function vol. 6: 31-38 (1988).

Parks, J. et al., Lipids of plasma membrane and outer acrosomal membrane from bovine spermatozoa, Biology of Reproduction 37:1249-1258 (1987).

Parks, J. Processing and handling bull semen for artificial insemination—Don't add insult to injury!, Department of Animal Science Cornell University.

Partec, Taking flow cytometry to the next generation, Catalogue 2001-2002.

Perez-Pe, R.et al., Semen plasma proteins prevent cold shock membrane damage to ram spermatozoa, Theriogenology 56 (3) : 425-434, Aug. 1, 2001, PMID: 11516122 http.//www.ncbi.nlm.nih.gov/entrez/query.fcgi?CMD=search&DB=pubmed, abstract only.

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society of Analytical Cytology, vol. 56A No. 2, Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research An International Journal, vol. 95, No. 3, Sep. 1983.

Piumi, F. et al., Specific cytogenetic labeling of bovine spermatozoa bearing X or Y chromosomes using florescent in situ hybridization (FISH), Genet, Sel. vol. 33: 89-98 (2001).

Edited by Bell-Prince, C. , NFCR Newsletter, http://www.ls.lanl.gov/NFCR/newsletter-Oc98/oct98.html Jan. 6, 2004, Oct. 1998.

Zahid, R.et al., Changes in motion characteristics, plasma membrane integrity, and acrosome morphology during cryopreservation of buffalo spermatozoa, Journal of Andrology, vol. 22 No. 2, Mar.-Apr. 2001.

Rees, William A., et al,Betaine Can Eliminate the Base Pair Composition Dependence of DNA Melting; Biochemistry 1993, 32, pp. 137-144.

Rens, W.et al.,An X-Y paint set and sperm FISH protocol that can be used for validation of cattle sperm separation procedures, Journals of Reproduction and Fertility, 121: 541-546 (2001).

Reyes, C.et al., Characterization of Secretory Proteins from cultured Cauda Epididymal Cells that significantly sustain bovine sperm motility, Molecular Reproduction and Development 63: 500-509 (2002).

Rippel,N.et al., Transcervical insemination: Effects of variation in total sperm number/dose on fertility, 83rd Annual Fall Conference for Veterinarians, Oct. 2002.

Rizzo, W. et al.,Liposome-mediated transfer of simian virus 40 DNA and minichromosome into mammalian cells, J. Gen. Virol 64:911-919 (1983).

Ruch, F., Determination of DNA content by microfluorometry, Introduction to Quanitative Cytochemistry, pp. 281-294 (1966).

Saacke, R.et al., Semen Quality test and their relationship to fertility, 4th National Association of Animal Breeders, (1972).

Salisbury, G.W.,et al."Preservation of Bovine Spermatozoa in Yolk-Citrate Diluent and Fields Results from its Use", Journal of Diary Science, 1941, vol. 24(11),pp. 905-910.

Schroter, S.et al., The glycocalyx of the sperm surface, Human Reproduction Update: vol. 5, No. 4, pp. 302-313 (1999).

Schuster, T. et al., Isolation of motile spermatozoa from semen samples using microfluidics, Reproductive BioMedicine Online,vol. 7 No. 1 75-81,www.rbmonline.com/Article/847, Apr. 16, 2003.

Seidel, George E. Jr. "What about sexed semen?" Hoard's Dairyman, The National Dairy Farm Magazine, May 10, 2001.

Sexing Technologies, Welcome to sexing Technologies, http://www.sexingtechnologies.com/ Dec. 11, 2003.

Shapiro, Howard M. M.D.,Building Flow Cytometers Chapter 9. Practical Flow Cytometry, second edition, Property of Washington University Medical Library, Aug. 1988.

Sharp, J. et al., Radially symmetric excitation and collection optics for flow cytometric sorting of aspherical cells, Cytometry, 29:363-370 (1997).

Shapiro, H., Re: cheap laser idea??, http://www.cyto.purdue.edu/hmarchiv/1998/1015.htm Feb. 3, 2004.

Smith, P.et al., Characteristics of a Novel Deep Red/ Infrared Fluorescent Cell-Permeant DNA Probe, DRAQ5, in Intact human Cells Analyzed by Flow Cytometry, Confocal and Multiphoton Microscopy, Cytometry 40:280-291 (2000).

Stanger, J.et al., The Relationship between motility and the FITC-BSA binding Properties of Mouse epididymal spermatozoa, The Journal of Experimental Zoology 227: 323-327 (1983).

Stanic,P. et al.,Comparison of protective media and freezing techniques for cryopreservation of human semen, http://www.ncbi.nlm.nih.gov/entrez/query.fcgi?CMD=search&DB=pubmed , Jul. 11, 2000, abstract only.

Stewart,R., Georgia Beef Challenge, Livestock Newsletter Jan.-Feb. 2002.

Takacs, T.et al.,Flow Cytometric determination of the sperm cell number in diluted bull semen samples by DNA staining method, Acta Biochim.Biophys.Hung. vol. 22, No. 1, pp. 45-57 (1987).

Thurston,L. et al., Identification of Amplified restriction fragment length polymorphism markers linked to genes controlling boar sperm viability following cryopreservation, Biology Of Reproduction 66: 545-554 (2992).

Tone,S.et al., A method of vital staining of mouse eggs using Hoechst dye, Department of Developmentail Biology (1986).

Tubman,L.et al., Abstract:Normality of calves resulting from sexed sperm, http://www.cvmbs.colostate.edu/bms/abstract/ges12.html Mar. 16, 2004.

Tucker,K.et al., Sperm separation techniques:Comparison of gradient products, Proceedings 2ed International workshop for Embryologists: Troubleshooting activities in the ART lab. (2002).

Van Dilla, M.et al., Measurement of Mammalian Sperm Deoxyribonucleic acid by Flow Cytometry, The journal of Histochemistry and Cytometistry vol. 25 No. 7 pp. 763-773 (1977).

Vazquez, J.et al., Nonsurgical Uterotubal Insemination in the Mare, Reproduction: Mare vol. 44 (1998).

Vishwanath,R.et al., Storage of bovine semen in liquid and frozen state, Animal Reproduction Science 62: 23-53 (2000).

Washburn, S., Sex-Sorted Semen; Still several steps short of sensational, http://www.cals.ncsu.edu/an sci/extention/animal/news/april96/april1965.html Mar. 16, 2004.

Welch,G.et al., Sex preselection: Laboratory Validation of the sperm sex ratio of Flow sorted X- and Y- sperm by sort reanalysis for DNA, Theriogenology 52:1343-1352 (1999).

Welch, G.et al., Fluidic and optical modification to a facs IV for flow sorting of X&Y Chromosomes bearing sperm based on DNA, International Society for Analytical Cytology (1994).

Wiltshire, M.et al., A Novel Deep Red/ Low infrared fluorescent flow cytometric probe DRAQ5NO, For the Discrimination of intact nucleated cells in apoptotic cell populations, Cytometry 39: 217-223 (2000).

Woelders, H. et al., Effects of Trehalose and Sucrose, Osmolality oh the freezing medium, and cooling Rate on Viability and intactness of bull sperm after freezing and thawing, Cryobiology 35: 93-105 (1997).

Wolf, D., Lipid domains in sperm plasma membranes, Molecular Membrane Biology 12: 101-104 (1995).

Wolf, D.et al., Changes in sperm plasma membrane lipid diffusibility after hyperactivation during In vitro capacitation in the mouse, The Journal of Cell Biology, vol. 102: 1372-1377(1986).

Wolf, D.et al., Diffusion and regionalization in membranes of maturing ram spermatozoa,The Journal of Cell Biology, vol. 98:1678-1684 (1984).

XY Files, Issue 1 Jun. 1999.

XY, Inc., Sex selection Procedure, http://www.xyinc.com/sex select. html, Feb. 21, 2003.

XY Files, Issue 4 Aug. 2000.

XY Files, Issue 2 Oct. 1999.

XY Files, Issue 3 Mar. 2000.

XY Files, Issue 5 Mar. 2001.

Lindsey, A. C., et al., Hysteroscopic insemination of mares with low numbers of nonsorted or flow sorted spermatozoa; Equine vet. J. (2002) 34(2) 128-132.

Sharpe, Johnathan, Advances in flow cytometry for sperm sexing, Unpublished paper, 2008.

Johnson, S.K., Possibilities with today's reproductive technologies. Available online at www.sciencedirect.com; Therio 64(2005) pp. 639-656.

Brogliatti, G. et al., Pregnancy Rates and First Born Calves by Artificial Insemination using Sexed Semen in Argentina: Therio. Jan. 2, 2002, vol. 57, No. 1 . p. 369.

Palma, G. et al., Sperm Physiology: The Ability to Produce Embryos In Vitro using Semen from Bulls with a Low Non-Return Rate. Therio. p. 308, Jan. 1, 1996, vol. 45, No. 1.

Gottlinger, Christopher et al., Cell-Cooling in Flow Cytometry by Peltier Elements. Cytometry 7:295-297 (1986).

Abstracts: American Dairy Science Assoc., American Society of Animal Science, Jun. 22-26, 2003 Phoenix AZ. J.Anim Sci. vol. 81 Suppl.1/J. Dairy Sci. vol. 86, Suppl. 1.

Garner, Duane L., et al, Effect of Semen Dilution on Bovine Sperm Viability as Determined by Dual-DNA Staining and Flow Cytometry. J. of Andrology, vol. 18, No. 3 May/Jun. 1997.

Lindsey, A. L., et al., Hysteroscopic or rectally guided, deep-uterine insemination of mares with spermatozoa stored 18 h at either 5° C. or 15° C. prior to flow-cytometric sorting, Animal Reproduction Science, vol. 85, Issues 1-2, Jan. 2005, pp. 125-130.

Schenk, J. L., et al., Pregnancy rates in heifers and cows with cryopreserved sexed sperm: Effects of sperm numbers per inseminate, sorting pressure, and sperm storage before sorting, Theriogenology (2008), doi:10.1016/j. theriogenolology. 2008:08:016.

Suh, T.K., et al., High pressure flow cytometric sorting damages sperm, Theriogenology 64 (2005) 1035-1048.

Upreti, G. C., et al., Studies on aromatic amino acid oxidase activity in ram spermatozoa: role of pyruvate as an antioxidant, Animal Reproduction Science 51 (1998) 275-287.

Schafer, D. J., et al., Comparison of progestin-based protocols to synchronize estrus and ovulation before fixed-time artificial insemination in postpartum beef cows, Journal of Animal Science Mar. 30, 2007, pp. 1-21.

Lamb, G. C., Synchronization of estrus and artificial insemination in replacement beef heifers using gonadotropin-releashing hormone, prostaglandin F2a and progesterone, Journal of Animal Science Nov. 1, 2006, vol. 84, pp. 3000-3009.

Saladarriaga, J. P., Ovarian, hormonal, and reproductive events associated with synchronization of ovulation and timed appointment breeding in Bos indicus-influenced cattle using intravaginal progesterone, gonadotropin-releasing hormone, and prostaglandin F2a, Journal of Animal Science Jan. 2007, vol. 85, pp. 151-162.

O'Brien, J. K. et al., Semen collection, characterization an preservation in a beluga (Delphinapterus leucas), 1st International workshop on Beluga whale research, husbandry and management in wild and captive environments Mar. 2007.

O'Brien, J. K. et al., Development of sperm sexing and associated assisted reproductve technology for sex preselection of captive bottlenose dolphins (Tursiops truncatus), Reproduction, Fertility and Development 2008, 18, 319-329.

Parallel Australian Patent Application No. 200237689; Office Action dated May 21, 2007.

Parallel Australian Patent Application No. 200237689; Office Action dated Oct. 3, 2007.

Parallel Australian Patent Application No. 200237689; Notice of Acceptance dated Jan. 2, 2008.

Parallel Australian Patent Application No. 200237689; Issued Patent dated Apr. 24, 2008.

Parallel Canadian Patent Application No. 2468772; Office Action dated May 9, 2008.

Parallel U.S. Appl. No. 10/433,183; Office Action dated Oct. 28, 2008.

Garner, D.L. et al., Viability Assessment of Mammalian Sperm Using SYBR-14 and Propidium Lodide, 1996, Biology of Reproduction, vol. 53, pp. 276-284.

Salisbury, G.W. et al., Substrate-Free Epididymal-Like Bovine Spermatozoa, J Repord Fertil, 1963, vol. 6, pp. 351-359.

Wong, P.Y.D., et al. Potassium Movement During sodium-induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel Anguilla Japonica, National Research Institute of Aquaculture, UNJR Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa , School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, Sep./Oct. 616-624, (2000).

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp., (1983).

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and -D-Glucuron idase Activity as Indicators of Sea Bass Semen Quality; Biology of Reproduction 70, 1679-1684 (2004).

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyciodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer.

Bavister, B.D. et al., The effects of Sperm Extracts and Energy Sources on the Motility and Acromosome Reaction of hamster Spermatozoa in vitero; Biology of Reporduction 16, 228-237 (1997).

Fattouh, El-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reporduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals; Journal of Andrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Garner, D.L. et al., Viability Assessment of Mammalian Sperm Using SYBR-14 and Propidium Lodide, 1996, Biology of Reporduction, vol. 53, pp. 276-284.

Salisbury, G.W. et al., Substrate-Free Epididymal-Like Bovine Spermatozoa, J Repord Fertil, 1963, vol. 6, pp. 351-359.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel Anguilla Japonica, National Research Institute of Aquaculture, UNJR Acquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa, School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, Sep./Oct. 616-624, (2000).

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp., (1983).

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and β-D-Glucuron idase Activity as Indicators of Sea Bass Semen Quality; Biology of Reproduction 70,1679-1684 (2004) Published online before print Feb. 11, 2004.

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Bavister, B.D. et al., The effects of Sperm Extracts and Energy Sources on the Motility and Acromosome Reaction of hamster Spermatozoa in vitero; Biology of Reproduction 16, 228-237 (1997).

Fattouh, El-S.M. et al., Effect of Caffine on the Post-Thaw Motility of Buffalo Spermatozoa; Theriogenology, Jul. 1991, vol. 36 No. 1.

U.S. Appl. No. 11/092,313, Response to Restriction filed Sep. 11, 2006.

U.S. Appl. No. 11/092,313, OA mailed Oct. 6, 2006.

U.S. Appl. No. 11/092,509, response to Restriction filed Jun. 21, 2006.

U.S. Appl. No. 11/092,509, OA mailed Jul. 21, 2006.

U.S. Appl. No. 11/092,338, Response to restriction filed Jan. 16, 2007.

U.S. Appl. No. 11/092,509, Resonse to OA filed Dec. 21, 2006.

U.S. Appl. No. 11/092,313, Response to OA filed Feb. 6, 2007.

U.S. Appl. No. 10/433,183, Office Action mailed Jan. 22, 2007.

Parallel Australian Application No. 2002237689; Office Action dated Jan. 9, 2006.

U.S. Appl. No. 11/092,509, Final OA dated Mar. 26, 2007.

U.S. Appl. No. 10/812,351, Response to Restrictive OA filed Apr. 5, 2007.

Koh-ichi Hamano, et al., Gender Preselection in Cattle with Intracytoplasmically injected, flow cytometrically sorted sperm heads, Biology of Reproduction 60, 1194-1197 (19900.

U.S. Appl. No. 60/253,787, filed Nov. 29, 2000.

U.S. Appl. No. 60/253,785, filed Nov. 29, 2000.

Parallel Australian Application No. 2002237689, Office Action dated Jan. 9, 2006.

Rath, D, et al., in Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, Tom and Currin, John Milk Production Evaluation In First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Dairy Industry $In Asia B. Japan; www.agnet.org/library/article/eb384b.html.

Crichton,E.; Huffman,S.;McSweeney,K.;and Schenk, J. 347 Artificial Insemination of Lactating Holstein Cows with sexed sperm: Abstract CSORP Publishing—Reproduction, Fertility and Development www.publish.csiro.au/nid/44/paper/RDv19n2Ab347.htm.

Lopez, H., Caraviello, D.Z., Satter, L.D. ,Fricke, P.M. and Wiltbank, M.C.; Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology www.foodsci.uoguelph.ca/dairyedu/biosyntheses.html.

Milk Production Relased Jul. 18, 2006, by the National Agricultural Statistics Service (NASS), Agri. Stats. Board, US Dept of Agri.

DeVries, A. Economic Value of Pregnancy in Diary Cattle Journal of Diary Sci. 89:3876-3885/American Dairy Sci. Assoc. 2006.

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

Akhtar, S., et al., "Prevalence of Five Stereotypes of Bluetongue Virus in a Rambouillet Sheep Flock in Pakistan", Veterinary Record 136, p. 495. (1995).

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R. P., et al. "Prospects For Sexing Mammalian Sperm," Animal Reproduction Laboratory College of Veterinary Medicine and Biomedical Sciences, Colorado State University. (1982).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Amoah, E. A. and Gelaye, S., "Biotechnological Advances in Goat Reproduction", J. Anim. Sci. 75(2): 578-585. (1996).

Anderson, V. K, et al., Intrauterine and tiefzervikale Insemination mit Gefriersperma bein Schat (Intrauterine and Deep Cervical Insemination With Frozen Semen in Sheep). Zuchthygiene 8:113-118. (1973).

Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).

Asbury, Charles A. "Fluorescence Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).
Baker, R.D., et al., "Effect of Volume of Semen, Number of Sperm and Drugs on Transport of Sperm in Artificially Inseminated Gilts", J. Anim. Sci. 27:88-93. (1968).
Bakker Schut, Tom C. "A New Principle of Cell Sorting by Using Selective Electroportation in a Modified Flow Cytometry," University of Twente, Mar. 10, 1990.
Barnes, F. L. and Eyestone, W. H., "Early Cleavage and the Maternal Zygotic Transition in Bovine Embryos", Therio. vol. 33, No. 1, pp. 141-149. (1990).
Batellier, F. et al., "Advances in Cooled Semen Technology" Animal Reproduction Science 68 p. 181-190 (2001).
Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).
Bedford, S .J. and Hinrichs, K., "The Effect of Insemination Volume on Pregnancy Rates of Pony Mares", Therio. 42:571-578. (1994).
Behrman, S. J., et al., "Freeze Preservation of Human Sperm" American Journal of Obstetrics and Gynecology vol. 103 (5) p. 654-664 Mar. 1, 1969.
Bellows, R. A., et al., "Cause and Effect Relationships Associated With Calving Difficulty and Calf Birth Weight", J. Anim. Sci. 33:407. (1971).
Berardinelli, J. G., et al., "Source of Progesterolle Prior to Puberty in Beef Heifers". J. Anim. Sci. 49:1276. (1979).
Berger, G. S. "Intratubal Insemination", Fertil. Steril. 48:328-330, (1987).
Bergfeld, E. G., et al., "Ovarian Follicular Development in Prepubertal Heifers is Influenced by Level of Dietary Energy Intake", Bio. of Repro. 51:1051. (1994).
Berry, B. W., et al., "Beef Carcass Maturity Indicators and Palatability Attributes", J. Anim. Sci. 38:507 (1974).
Beyhan, Z., et al., "Sexual Dimorphism in IVF Bovine Embryos Produced by Sperm Sorted by High Speed Flow Cytometry", abstr. Therio. 49(1): 359 (1998).
Beyhan, Z., Et Al., 1999 Sexual Dimorphism in IVM-IVF Bovine Embryos Produced from X and Y Chromosome-Bearing Spermatozoa Sorted By High Speed Flow Cytometry. Theriogenology. 52: 35-48.
Bigos, Martin "Nine Color Eleven Parameter Immunophenotyping Using Three Laser Flow Cytometry," Stanford University Dec. 22, 1998.
Bioxcell, Bovine Sperm Preservation, Advertisement Jun. 28, 2005.
Bond, J., et al., "Growth and Carcass Traits of Open Beef Heifers Versus Beef Heifers That Have Calved", Nutrition Reports International 34:621. 1986.
Boucque, C. V., et al., "Beef-Production With Maiden and Once-Calved Heifers", Livestock Prod. Sci. 7:121. 1980.
Bourdon, R. M. and J. S. Brinks. "Simulated Efficiency of Range Beef—Production III. Culling Strategies and Nontraditional Management-Systems", J. Anim. Sci. 65:963. 1987.
Bracher, V. and Allen, W.R., "Videoendoscopic Examination of the Mare's Uterus: I. Findings in Normal Fertile Mares", Equine Veterinary Journal, vol. 24, p. 274-278. 1992.
Braselton, W. E. and McShan, W. H., "Purification and Properties of Follicle Stimulating and Luteinizing Hormones From Horse Pituitary Glands" Arch. Biochem. Biophys. 139:45-48. 1970.
Braun, J. et al, "Effect of Different Protein Supplements on Motility and Plasma Membrane Integrity of Frozen-Thawed Stallion Spermatozoa", Cryobiology (1995) 32:487-492.
Brethour, J. R. and Jaeger, J. R "The Single Calf Heifer System", Kansas Agric. Sta. Rep of Progress 570. 1989.
Brinsko, S.P. et al., "Artificial Insemination and Preservation of Semen." Veterinary Clinics of North America:Equine Practice vol. 8 No. 1 Apr. 1992 pp. 205-218.
Bristol, F. "Breeding Behavior of a Stallion at Pasture With 20 Mares in Synchronized Oestrus" J. Reprod. Fertil. Suppl. 32:71. 1982.
Brookes, A. J. and O'Byrne, M., "Use of Cow-Heifers in Beef Production" J. of the Royal Agricultural Society of England 126:30. 1965.

Buchanan, B. R., et al, "Insemination of Mares with Low Numbers of Either Unsexed or Sexed Spermatozoa", Therio. vol. 53, p. 1333-1344. 2000.
Buchanan, B.R. "Pregnancy Rates in Mares Following a Single Insemination with a Low Number of Spermatozoa into the Tip of the Uterine Horn" Theriogenology p. 395, (Jan. 1999).
Burns, P. D. and Spitzer, J.C., "Influence of Biostimulation on Reproduction in Postpartum Beef-Cows", J. Anim. Sci. 70:358. 1992.
Burwash, L. D., et al., "Relationship of Duration of Estrus to Pregnancy Rate in Normally Cycling, Non Lactating Mares" J.A.V.M.A. 165:714-716. 1974.
Byerley, D. J., et al., "Pregnancy Rates of Beef Heifers Bred Either on Puberal or Third Estrus". J Anim. Sci. 65:645. 1987.
Caslick, E. A., "The Vulva and the Vulvo-Vaginal Orifice and its Relation to Genital Health of the Thoroughbred Mare", Cornell Veterinarian, vol. 27, p. 178-187. 1937.
Catt, et al., "Assessment of Ram and Boar Spermatozoa During Cell-Sorting by Flow Cytometry", Reproduction Dom Animal, vol. 32, pp. 251-258. 1997.
Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.
Cave-Penney, Tony, "Sexed Semen Offers Faster Genetic Gain", Farming News, Livestock Supplement, Feb. 1997, p. 28.
Chandler, J. E., "Videomicroscopic Comparison of Bull Sperm and Leukocyte Chromosome Areas as Related to Gender", J Dairy Sci 73, p. 2129-2135. 1990.
Chandler, J. E., et al, "Bovine Spermatozoal Head Size Variation and Evaluation of a Separation Technique Based on this Size", Therio. 52, p. 1021-1034. 1999.
Chen, S.H. "Effects of Oocyte Activation and Treatment of Spermatozoa on Embryonic Development Following Intracytoplasmic Sperm Injection in Cattle" Theriogenology 48: 1265-1273, 1997.
Chen, Y. et al., Survival of Bull Spermatozoa Seeded and Frozen at Different Rates in Egg Yolk-Tris and Whole Milk Extenders, 1993 J Dairy Sci 76:1028-1034.
Chin, W. W. and Boime, I. 1990. In Glycoprotein Hormones. Serona Symp. Norwell, MA. pp. 19-20.
Choi, Y.H. "Developmental Cappacity of Equine Oocytes Matured and Cultured in Equine Trophoblast-Conditioned Media" Theriogenoogy 56: 320-339, 2001.
Chung, Y. G., et al. "Artificial insemination of Superovulated Heifers With 600,000 Sexed Sperm". J Anim. Sci. Suppl. 1. 836:215. 1998 abstr.
Clement, F., et al., "Which Insemination Fertilizes When Several Successive Inseminations are Performed Before Ovulation" 7th Int. Symp. Eq. Repro. 151. 1998 abstr.
Cran, D. G., et al, "Production of Lambs by Low Dose Intrauterine Insemination With Flow Cytometrically Sorted and Unsorted Semen", Therio. p. 267. 1997.
Cran, D. G., et al., "Sex Preselected in Cattle: A Field Trial", Veterinary Record 136, 1995, p. 495-496.
Cran, D. G., et al., "Production of Bovine Calves Following Separation of X- and Y-Chromosome Bearing Sperm and In Vitro Fertilization". Vet. Rec. 132:40-41. 1993.
Cran, D. G., et al., "The Predetermination of Embryonic Sex Using Flow Cytometrically Separated X and Y Spermatozoa" Human Reproduction Update 1996, vol. 2 (4) p. 355-63.
Crowley, J. P. "The facts of Once-Bred Heifer Production" School of Agric., Univ. of Aberdeen, Scotland. 1973.
Cui, K. et al, "X Larger than Y", Nature 366, p. 177-118, 1993.
Cui, K., "Size Differences Between Human X and Y Spermatozoa and Prefertilization Diagnosis", Molecular Human Reproduction, vol. 3, No. 1, pp. 61-67. 1997.
Curran, S. "Fetal Gender Determination" in *Equine Diagnostic Ultrasonography* 1st ed. Rantanen, N.W. and McKinnon A.O. (eds.) Williams and Williams, 1998, p. 165-69.
da Silva, Coutinho M.A.. "Effect of time of oocyte collection and site of insemination on oocyte transfer in mares." Animal Reproduction and Biotechnology Laboratory, Colorado State University, Fort Collins Journal of Animal Science 2002. 80:1275-1279.

DakoCytomation, "MoFlo® Sorters" http://www.dakocytomation.us/prod_productrelatedinformation?url=gprod_moflo_index.htm one page, printed Jun. 26, 2003.

Database up 1 BR9704313 (Alves, De Resende et al) Jun. 4, 1999.

Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.

de Leeuw, F.E. et al. "Effects of carious cryoprotective agents and membrane-stabilizing compounds on bull sperm emebrane integrity after cooling and freezing" Cryobiology US, Academic Press Inc 1993 pp. 32-44.

Dean, P.N., et al. "Hydrodynamic Orientation of Spermatozoa Heads for Flow Cytometry". Biophys. J. 23:7-13. 1978.

Demick, D.S., et al. "Effect of Cooling, Storage, Glycerization and Spermatozoal Numbers on Equine Fertility" J. Anim. Sci. 43:633-637. 1976.

DenDaas, J. H. G., et al. "The relationship between the number of spermatozoa inseminated and the reproductive efficiency of dairy bulls" J Dairy Sci. 81: 1714-1723. 1998.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From seventeen to Nineteen Days in the Melengestrol Acetate-Prostaglandin Estrous Synchronization Program for Heifers". The Professional Animal Scientist 16:164. 2000.

Diagnostic Products Corporation, "Coat-A-Count" http://www.Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post- Isemination Affects Cryosurvival of In Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Donaldson, L. E., "Effect of Insemination Regimen on Embryo Production in Superovulated Cows", The Veterinary Record, Jul. 13, p. 35-37, 1985.

Donoghue, A.M., et al. "Timing of Ovulation after Gonadotropin and its Importance to Successful Intrauterine Insemination in the Tiger (*Panthera tigris*)" J. Reprod. Fertil. 107:53-58 1996.

Douglas, R. H., "Review of Induction of Superovulation and Embryo Transfer in the Equine" Therio. 11:33-46. 1979.

Douglas, R. H., et al. "Induction of Ovulation and Multiple Ovulation on Seasonally-Anovulatory Mares with Equine Pituitary Fractions." Therio. 2(6): 133-142. 1974.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analysis of DNA content of Living Spermatozoa Using Flow Cytometry Technique Journal of Reproduction and Fertility, 1993, vol. 98, pp. 357-365.

Duchamp, G., et al. "Alternative Solutions to hCG Induction of Ovulation in the Mare" J. Reprod. Fertiil. Suppl. 35:221-228. 1987.

Evans, M. J. and Irvine, C. H. G. "Induction of Follicular Development, Maturation and Ovulation by Gonadotropin Releasing Hormone Adminstration to Acyclic Mares" Bio. Reprod. 16:452-462. 1977.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Fitzgerald, B. P., et al. "Effect of Constant Adminstration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.

Fluharty, F.L., et al., "Effects of Age at Weaning and Diet on Growth of Calves",Ohio State University Dept. of Animal Sciences. 1966 Ohio Agri. And Den. Circular, 156:29 1966.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc of the NAAB Tech. Conf. On Artificial Insemination and Reproduction, 62-70 (1984).

Foulkes, J. A., et al. "Artificial Insemination of Cattle Using Varying Numbers of Spermatozoa." Vet. Rec. 101:205. 1977.

Francon, M. and Yamamoto, T., "Un Noveau et tres simple dispositif interferentiel applicable as microscope" Optica Acta 9, p. 395-408. 1962.

Fugger, E. F. "Clinical Experience with Flow Cytometric Separation of Human X- and Y-Chromosome Bearing Sperm", Therio. vol. 52, pp. 1435-1440.1999.

Fuller, Robert R. "Characterizing Submicron Vesicles With Wavelenth-Resolved Fluorescence in Flow Cytometry," University of Illinois, May 13, 1996.

Fulwyler, M. J. "Electronic Separation of Biological Cells by Volume." Science. 150:910. 1965.

Fulwyler, M. J. "Hydrodynamic Orientation of Cells." J of Histochem. and Cytochem. 25:781-783. 1977.

Garner, D. L., et al. "Quantification of the X and Y Chromosome-Bearing Spermatozoa of Domestic Animals by Flow Cytometry." Biol. Reprod. 28:312-321. 1983.

Ginther, O. J., "Sexual Behavior Following Introduction of a Stallion into a Group of Mares" Therio. vol. 19 (6) Jun. 1983.

Ginther, O. J., "Some Factors Which Alter Estrus Cycle in Mares." J. Anim. Sci. 33:1158. 1971 abstr.

Ginther, O. J., Reproductive Biology of the Mare. (2nd Ed.) Equiservices, Cross Plains, WI. 1992.

Gledhill, B. L. "Gender Preselection: Historical, Technical and Ethical Perspective." Semen Reprod. Endocrinol. 6:385-395. 1988.

Gombe, S. and Hansel, W. "Plasma Luteinizing Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper—Mayer", Zbechr. F. Phys. 47 S.509 (1928).

Gottlinger et al., "Operation of a Flow Cytometer", Flow Cytometry and Cell Sorting, A. Radbruch (Ed.), 1992, pp. 7-23.

Gourley, D. D. and Riese, R. L. "Laparoscopic Artificial Insemination in Sheep." Vet. Clin. N. Amer: Food Anim. Prac. 6(3): 615-633 (1990).

Graham, J. Analysis of Stallion semen and its Relation to Fertility. Abstract Complete article from Reproductive Technology vol. 12 # Apr. 1, 1996 now included in XYIDS000213.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K, "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal Weaned Calves". I. Prod. Agric. 4:168 (1991).

Grondahl, C., et al, "In Vitro Production of Equine Embryos", Biology of Reproduction, Monograph Series I, p. 299-307 (1995).

Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).

Gurnsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).

Hall, J. B., et al., "Effect of Age and Pattern of Gain on Induction of Puberty with a Progestin in Beef Heifers." J. Anim. Sci. 75:1606 (1997).

Hamamatsu, "Technical Information, Optical Detector Selection: A Delicate Balancing Act", web page, http://www.optics.org/hamamatsu/photodiode.html, printed on Apr. 15, 2000, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harrison, L.A., et al., "Comparison of HCG, Buserelin and Luprostiol for Induction of Ovulation in Cycling Mares." Eq. Vet. Sci. 3:163-166 (1991).

Harte, F. J. "System of Production of Beef From Once Calved Heifers." In: J.C. Taylor (Ed.) *The Early Calving of Heifers and its Impact on Beef Production*. 123 (1975).

Hawk, H. W., et al., "Fertilization Rates in Superovulating Cows After Deposition of Semen on the Infundibulum Near the Uterotubal Junction or After Insemination with High Numbers of Sperm", XP-002103478, Therio. vol. 29, No. 5, p. 1131-1142 (1988).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," pp. 108-117, Sci.Am. 234 (1976) pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fertil. 98:597-602. 1993.

Hohenboken, W. D. "Applications of sexed semen in cattle production." Therio. 52:1421. 1999.

Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.

Horan, Paul K. "Quantitative Single Cell Ana,lysis and Sorting, Rapid Analysis and sorting of cells is emerging as an important new technology in research and medicine.", Science, Oct. 1977.

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (Mustela putorious furo) and Pregnancies After Laparoscopic Intrauterine Insemination With Frozen-Thawed Spermatozoa." J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 989, p. 181-190.

IMV Technologies, Protocol of Bioxcell with Fresh Semen, 1 page, 2000.

IMV Technologies, Protocol of Bioxcell with Frozen Semen, 2 pages, 2000.

Irvine, C H. G. and Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-266.

Jafar, et al., "Sex Selection in Mammals: A Review", Therio. vol. 46, p. 191-200. (1996).

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production*. 10. (1975).

Jasko, D. J., et al., "Effect of Insemination Volume and Concentration of Spermatozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, A. L. "Pulsatile Administration of Gonadotropin Releasing Hormone Advances Ovulation in Cycling Mares", Biol. Reprod. 35:1123-1130, (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, L.A., "Flow Cytometric Determination of Spermatozoa Sex Ratio in Semen Purportedly Enriched for X or Y Bearing Spermatozoa", Therio. 29:265 abstr.

Johnson, L.A., "Gender Preselection in Domestic Animals Using Flow Cytometrically Sorted Sperm" J. Anim. Sci. (Suppl I) 70:8-18. (1992).

Johnson, L.A., "The Safety of Sperm Selection by Flow Cytometry" Ham. Reprod. 9(5): 758. (1994).

Johnson, L.A., "Advances in Gender Preselection in Swine" Journal of Reproduction and Fertility Supplement, vol. 52, p. 255-266 (1997).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Gender Preselection in Mammals: An Overview", Deutsch. Tierarztl. Wschr, vol. 103, p. 288-291 (1996).

Johnson, L.A., "Isolation of X- and Y-Bearing Spermatozoa for Sex Preselection." Oxford Reviews of Reproductive Biology. Ed. H. H. Charlton. Oxford University Press. 303-326. (1994).

Johnson, L.A., "Sex Preselection by Flow Cytometric Separation of X and Y Chromosome Bearing Spermatozoa Based on DNA Difference: a Review." Reprod. Fertil. Dev. 7:893-903. (1995).

Johnson, L.A., "Sex Preselection in Rabbits: Live Births from X and Y Sperm Separated by DNA and Cell Sorting", Biology of Reproduction 41, pp. 199-203 (1989).

Johnson, L.A., "Sex Preselection in Swine: Altered Sex Rations in Offspring Following Surgical Insemination of Flow Sorted X- and Y-Bearing Sperm", Reproduction in Domestic Animals, vol. 26, pp. 309-314 (1991).

Johnson, L.A., "Sex Preselection in Swine: Flow Cytometric Sorting of X- and Y- Chromosome Bearing Sperm to Produce Offspring", Boar Semen Preservation IV, p. 107-114. (2000).

Johnson, L.A., "Successful Gender Preselection in Farm Animals", Agricultural Biotechnology, p. 439-452. (1998).

Johnson, L.A., et al. "Sex Preselection: High-speed Flow Cytometric Sorting of X and Y Sperm for Maximum Efficiency", Therio. vol. 52, p. 1323-1341 (1999).

Johnson, L.A., et al., "Enhanced Flow Cytometric Sorting of Mammalian X and Y Sperm: High Speed sorting and Orienting Nozzle for Artificial Insemination", Therio. 49(1): 361 (1988) abstr.

Johnson, L.A., et al., "Flow Sorting of X and Y Chromosome-Bearing Spermatozoa into Two Populations", Gamete Res. 16:203-212. (1987).

Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).

Johnson, L.A., et al., "Flow Cytometry of X- and Y-Chromosome Bearing Sperm for DNA Using an Improved Preparation Method and Staining with Hoechst 33342." Gamete Research 17: 203-212. (1987).

Johnson, L.A., et al., "Modification of a Laser-Based Flow Cytometer for High-Resolution DNA Analysis of Mammalian Spermatozoa" Cytometry 7, pp. 268-273 (1986).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley. "Meat Quality of Once-Calved Heifers." Irish J. of Agric. Research 10:281. (1971).

Kachel, V., et al., "Uniform Lateral Orientation, Caused by Flow Forces, of Flat Particles in Flow-Through Systems", The Journal of Histochemistry and Cytochemistry, vol. 25, No. 7, pp. 774-780. (1997).

Kanayama, K., et al., "Pregnancy by Means of Tubal Insemination and Subsequent Spontaneous Pregnancy in Rabbits." J. Int. Med. Res. 20:401-405. (1992).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle -Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semen." J S Afr. Vet. Assoc. 56(2): 61-63. (1985).

Levinson, G., et al., "DNA-based X-Enriched Sperm Separation as an Adjunct to Preimplantation Genetic Testing for the Preparation of X-linked Disease." Mol. Human Reprod. 10:979-982. (1995).

Lindsey, A. C., et al., "Low Dose Insemination of Mares Using Non-Sorted and Sex-Sorted Sperm" Animal Reproduction Science 68 p. 279-89 (2001).

Lindsey, A., et al., "Hysteroscopic Insemination of Mares with Nonfrozen Low-dose Unsexed or Sex-sorted Spermatozoa", pp. 1-15 currently unpublished.

Linge, F. "Faltforsok med djupfrost sperma (Field Trials With Frozen Sperm)." Farskotsel. 52:12-13. (1972).

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Loy, R. G. and Hughes, J.P. "The Effects of Human Chorionic Gonadotropin on Ovulation, Length of Estrus, and Fertility in the Mare." Cornell Vet. 56:41-50 (1965).

Lu, K. H. et al., "In Vitro Fertilization of Bovine Oocytes with Flow-Cytometrically Sorted and Unsorted Sperm from Different Bulls" Therio. abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug in Dairy Cattle?", Animal Research Station, Private Bag, Hamilton, New Zealand, Therio. vol. 18, No. 3, p. 245-253 (1982).

Manni, Jeff. "To-Photon Excitation Expands the Capabilities of Laser-Scanning Microscopy,", Biophotonics Intl. (1996).

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow ", Proceedings Annual Conference of the International Embryo Transfer Society, Netherlands, Therio. vol. 53 p. 201, Jan. 2000.

Matsuda, Y. and Tobari, I. "Chromosomal Analysis in Mouse Eggs Fertilized in Vitro With Sperm Exposed to Ultraviolet Light (UV) and Methyl and Ethyl Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calving of Heifers and its Impact on Beef Production*. (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1783 (1990).

McKinnon, A.O. and Voss, J. L. *Equine Reproduction*. Lea and Febiger. Philadelphia, London (1993).

McKinnon, A.O., et al., "Predictable Ovulation in Mares Treated With an Implant of the GnRH Analogue Deslorelin." Eq. Vet. J. 25:321-323. (1993).

McKinnon, A.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

McNutt, T. L. et al., "Flow Cytometric Sorting of Sperm: Influence on Fertilization and Embryo/Fetal Development in the Rabbit", Molecular Reproduction and Development, vol. 43, p. 261-267 (1996).

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke, E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991,vol. 30 pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michaels, C., "Beef A. I. Facilities That Work", Proc. Fifth N.A.A.B Tech. Conf. A. I. Reprod. Columbia, MO. pp. 20-22.

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 54:548, (1971).

Molinia, F. C., et al., "Successful Fertilization After Superovulation and Laparoscopic Intrauterine Insemination of the Brushtail Possum Trichosurus vulpecula, and Tammar Wallaby, Macropus eugenii." J. Reprod. Fertil. 112:9-17. (1998).

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation of X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001(Su;;I. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Pace, M. M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 23:115-121.

Parrish, J. J., et al., "Capacitation of Bovine Sperm by Heparin", Department of Meat and Animal Science, Biology Of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al., "Sex Diagnosis of Equine Preimplantation Embryos Using the Polymerase Chain Reaction", Therio. vol. 44:619-627 (1995).

Penfold, L.M.et at., "Comparative Motility of X and Y Chromosome-Bearing Bovine Sperm Separated on the Basis of DNA Content", Mol. Reprod. And Develop. 1998, vol. 50,pp. 323-327.

Perry, E. J., "Historical Background" The Artificial Insemination of Farm Animals. 4th ed. E. J. Perry (ed.) New Brunswick, Rutgers University Press, pp. 3-12. (1968).

Petersen, G. A., et al, "Cow and Calf Performance and Economic-Considerations of Early Weaning of Fall-Born Beef Claves", J. Anim. Sci., 64:15, pp. 15-22. (1987).

Petit, M. "Early Calving in Suckling Herds." In: J.C. Taylor (ed.) *The Early Calving of Heifers and its Impact on Beef Production*. p. 157-176. (1975).

Picket B.W., et al., "Livestock Production Science," 1998.

Pickett, B. W, et al., "Factors Influencing the Fertility of Stallion Spermatozoa in an A. I. Program." Proc. 8th International Congress Anim. Reprod. A. I. Krakow, Poland. 4:1049-1052. (1976).

Pickett, B. W., et al., "Effect of Seminal Extenders on Equine Fertility." J. Anim. Sci. 40:1136-1143. (1975).

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "Management of the Mare for Maximum Reproductive Efficiency." CSU Anim. Repro. Lab. Bull. No. 06. Fort Collins CO. (1989).

Pickett, B. W., et al., "Procedures for Preparation, Collection, Evaluation and Insemination of Stallion Semen." CSU Exp. Sta. Artira. Reprod. Lab. Gen. Series Bull. 935. (1973).

Pickett, B. W., et al., "Recent Developments in Artificial Insemination in Horses", Livestock Production Science, 40, p. 31-36 (1994).

Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al, "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).

Pinkel, D., et al., "High Resolution DNA Content Measurements of Mammalian Sperm", Cytometry 3:1-9. (1982).

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, Naouka Publishing House, 1983, pp. 181-195.

Province, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilzing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Low Dose Insemination Technique in the Pig", Boar Semen Preservation IV, p. 115-118. (2000).

Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).

Rathi, R. et al., "Evaluation of In Vitro Capacitation of Stallion Spermatoza", Biology of Reproduction 2001,vol. 65, pp. 462-470.

Recktenwald, Diether. "Cell Separation Methods and Applications," New York. 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (199).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rens, W., et al., "Improved Flow Cytometric Sorting of X- and Y-Chromosome Bearing Sperm: Substantial Increase in Yield of Sexed Semen", Molecular Reproduction and Development, p. 50-56(1999).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Preproduction 55, 1012-1016 1996.

Romita, A. "Some Considerations on the Beef Situation in Italy." In: J.C. Taylor (ed.) *The Early Calving of Heifers and its Impact on Beef Production*. 23. (1975).

Roser, J. F., et al., "Reproductive Efficiency in Mares With Anti-hCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Claving Heifers Versus Maiden Heifers for Beef-Production from Dairy herds. I. The Effects of Genotype (Friesian and Cardioads x Friesian) and Two Feeding Levels in the Rearing Period on Growth and Carcass Quality." Livestock Prod. Sci. 16:1 (1987).

Rowley, H. S., et al., "Effect of Insemination Volume on Embryo Recovery in Mares." J. Equine Vet. Sci. 10:298-300 (1990).

Roy, J. H., "Rearing Dairy-Herd Replacements." Journal of the Society Of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Salamon, S., *Artificial Insemination of Sheep*, Chippendale, New South Whales. Publicity Press p. 83-84 (1976).

Salisbury, G. W. and VanDemark, N. L. "Physiology of Reproduction and Artificial Insemination of Cattle." San Francisco: Freeman and Company. p. 442-551 (1978) (1961 & 1978 Combined) Chapters 16 and 17 are the complete article.

Schenk, J. L. "Applying Semen Sexing Technology to the AI Industry", Proceedings of the 18th Technical Conference on Artificial insemination & Reproduction, 2000.

Schenk, J. L, et al., "Imminent Commercialization of Sexed Bovine Sperm", Proceedings, The Range Beef Cow Symposium XVL, p. 89-96 (1999).

Schenk, J. L., "Cryopreservation of Flow-Sorted Bovine Spermatozoa", Therio. vol. 52, 1375-1391 (1999).

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K, et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination ", 7th International Symposium On Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34, Sep. 2001.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Numbers of Nonfrozen and Sexed Spermatozoa", Atlantic Breeders Cooperative, Therio. 48: pp. 1255-1264, (1997).

Seidel, G. E. Jr et al., "Current Status of Sexing Mammalian Spermatozoa," Society for Reproduction and fertiity, pp. 733-743, 2002.

Seidel, G. E. Jr., "Commercilizing Reproductive Biotechnology—The Approach used by XY, Inc.," Theriogenology, p. 5, 1999.

Seidel, G. E. Jr. et al., "Insemination of Heifers with Sexed Sperm", Therio, vol. 52, pp. 1407-1421 (1999).

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Artificial Insemination With X-and Y-Bearing Bovine Sperm", Animal Reproduction and Biotechnology Laboratory, Colorado State University, (1996).

Seidel, G. E. Jr., "Status of Sexing Semen for Beef Cattle", Texas A & M University 45th Annual Beef Cattle Short Course and Trade Show Proceedings, Aug. 9-11, p. III24-III27, (1999).

Seidel, G. E. Jr., et al, "Insemination Of Heifers With Very Low Numbers Of Frozen Spermatozoa", CSU, Atlantic Breeders Cooperative, Lancaster, PA, DUO Dairy, Loveland, CO, Jul. 1996.

Seidel, G. E. Jr., et al, "Insemination of Holstein Heifers With Very Low Numbers Of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio, vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20, Oct 1988.

Senger, P. L., et al., "Influence of Cornual Insemination on Conception in Dairy Cattle." J Anim. Sci. 66:3010-3016. (1988).

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N. W. "The Response of the Ewe to Pregnant Serum Mare Gonadotropin and to Horse Anterior Pituitary Extract." J. Reprod. Fertil. 14:175-177. (1967).

Shilova, A. V., et al., "The Use of Human Chorionic Gonadotropin for Ovulation Date Regulation in Mares." VIIIth Int. Congress on Anim. Repro. and A. I. 204-208. (1976).

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine Spermatozoa, Dairy Science 1979 J 62:1297-1303.

Solsberry G.U., Van-Denmark N. L., Theory and practice of artificial cow insemination in USA, Moscow, Kolos Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HMD 532, www.specra-physics.com.

Spectra-Physics, The Solid State Laser Company, Vanguard 350-HMD 355, www.specraphysics.com.

Squires, E. L, et al., "Effect of Dose of GnRH Analog on Ovulation in Mares." Therio. 41:757-769. (1994).

Squires, E. L, "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Procedures for Handling Frozen Equine Semen for Maximum Reproductive Efficiency", pp. 1, 39-41, 81-89, (1998).

Staigmiller, R.B. "Superovulation of Cattle with Equine Pituitary Extract and Porcine FSH" Theriogenology 37: 1091-1099 1992.

Stap J. Et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp, 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Sullivan, J. J., et al., "Duration of Estrus and Ovulation Time in Nonlactating Mares Given Human Chorionic Gonadotropin During Three Successive Estrous Periods." J.A.V.M.A. 162:895-898. (1973).

Sumner, A. T. and Robinson, J. A., "A Difference in Dry Mass Between the Heads of X and Y-Bearing Human Spermatozoa", J Reprod Fertil. 48, p. 9-15 (1976).

Swanson, E. W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Taljaard, T. L., et al., "The Effect of the Laparoscopic Insemination Technique on the Oestrus Cycle of the Ewe." J. South Afr. Vet. Assoc. 62(2): 60-61. (1991).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ, pp. 401-440, (1985).

Tervit, H.R., et al., "Successful Culture In Vitro of Sheep and Cattle Ova", Agricultural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

*Time-Bandwidth Products* "GE—100—XHP", www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

van Munster, E. B., "Geslachtsbepaling met interferometrie", Derde prijs NtvN-prijsvraag voor pas-gepromoveerden 65/4, (Sex Determination with Interferometry) p. 95-98 (1999).

van Munster, E. B., et al, "Difference in Sperm Head Volume as a Theoretical Basis for Sorting X & Y-Bearing Spermatozoa: Potentials and Limitations", Therio 52, pp. 1281-1293 (1999).

van Munster, E. B., et al, "Difference in Volume of X- and Y-chromosome Bearing Bovine Sperm Heads Matches Difference in DNA Content" Cytometry vol. 35 p. 125-128 (1999).

van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

Vazquez, J. J. et al., "Nonsurgical Uterotubal Insemination in the Mare", Proceedings of the 44th Annual Convention of the American Association of Equine Practitioners, vol. 44, pp. 68-69 (1998).

Vazquez, J. M., et al., "A. I. in Swine; New Strategy for Deep Insemination with Low Number of Spermatozoa Using a Non-surgical Methodology", 14th International Congress on Animal Reproduction, vol. 2, Stockholm, Jul. 2000, p. 289.

Vazquez, J., et al., "Development of a Non-surgical Deep Intra Uterine Insemination Technique", Boar Semen Preservation IV, IVth International Conference on Boar Semen Preservation, Maryland, pp. 262-263, (1999).

Vazquez, J., et al., "Hyposmotic Swelling Test as Predictor of the Membrane Integrity in Boar Spermatozoa", Boar Semen Preservation IV, IVth International Conference on Boar Semen Preservation, Maryland, pp. 263, (1999).

Vazquez, J., et al., "Successful low dose insemination by a fiber optic Endoscope technique in the Sow", Proceedings Annual Conference of the International Embryo Transfer Society, Netherlands, Theriogenology, vol. 53 Jan. 2000.

Vidament, M., et al., "Equine Frozen Semen Freezability and Fertility Field Results." Therio. 48:907. (1997).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Voss, J. L. and Pickett, B. W., "Reproductive Management of the Broodmare." CSU Exp. Sta. Anim. Reprod. Lab. Gen. Series. Bull. 961. (1976).

Voss, J. L., et al., "Effect of Number and Frequency of Inseminations on Fertility in Mares." J. Reprod. Fertil. Suppl. 32:53-57. (1982).

Voss, J. L., et al., Effect of Human Chorionic Gonadotropin on Duration of Estrous Cycle and Fertility of Normally Cycling, Nonlactating Mares. J.A.V.M.A. 165:704-706. (1974).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservvation of Spermatozoa and the Assessment of Their Post-Thawing Function," Reprod. Fertil. Dev. 7:871-891 (1995) Abstract.

Welch G., et al., Fluidic and Optical Modifications to a FACS IV for Flow Sorting of X- and Y-Chromosome Bearing Sperm Based on DNA. Cytometry 17 (Suppl. 7): 74. (1994).

Welch, G., et al., "Flow Cytometric Sperm Sorting and PCR to Confirm Separation of X- and Y-Chromosome Bearing Bovine Sperm", Animal Biotechnology, 6, pp. 131-139 (1995).

Wheeler, T. L, et al., "Effect of Marbling Degree on Beef Palatability in Bos-taurus and Bos-indicus cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, C. G., et al., "Effects of Repeated hCG Injections on Reproductive Efficiency in Mares." Eq. Vet. Sci. 4:301-308. (1990).

Wilson, D. E. et al., "Mammal Species of the World", Smithsonian Institution Press, 1993, 1206 pp.

Wilson, M.S. "Non-surgical Intrauterine Artificial Insemination in Bitches Using Frozen Semen." J. Reprod. Fertil. Suppl. 47:307-311. (1993).

Windsor, D. P., et al, "Sex Predetermination by Separation of X and Y Chromosome-bearing Sperm: A Review", Reproduction of Fertilization and Development 5, pp. 155-171, (1993).

Wintzer Et al.:"Krankheiten des Pferdes Ein Leitfaden fur Studium and Praxiz," 1982, nParey, Berlin Hamburg XP002281450.

Woods, G. L. and Ginther, O. J. "Recent Studies Related to the Collection of Multiple Embryos in Mares." Therio. 19:101-108. (1983).

Woods, J., et al., "Effects of Time of Insemination Relative to Ovulation on Pregnancy Rate and Embryonic-Loss Rate in Mares." Eq. Vet. J. 22(6): 410-415. (1990).

Zhou, Hongwei, et al. "Research on and Development of Flow Cell Sorting Apparatuses," Gazette of Biophysics, vol. 13, ed. 3, 1997.

Hamamatsu, "Photomultiplier Tubes," web page, http://www.optics.org/hamamatsu/pmt.html. Printed on Apr. 15, 2000 4.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23, (1999).

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.

Hollinshead F. K. et al. "Production of lambs of predetermined sex after the insemination of ewes with low Number of frozen-thawed sorted X- or Y- Chromosome-bearing spermatozoa", Reprod. Fertil. And Develop. 2002, vol. 14, pp. 503-508.

Hollinshead F. K. et al. "Sex-Sorting and Re-cryopreservation of Frozen-Thawed Ram Sperm for in Vitro Embryo Production" Theriogenology, vol. 59. (2003) pp. 209.

Dhali et al. Vitrification of Buffalo (Bubalus Bubalis)Oocytes, Embryo Theriogenology vol. 53, pp. 1295-1303 (2000).

Borini et al. Cryopreservation of Mature Oocytes: The use of a trypsin inhibitor enhances fertilization and obtained embryos rates, Fertil. Steril. (1997), vol. 68 (Suppl.).

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for In Vitro fertiliation and AI, Journal of Animal Science,vol. 77, Suppl 2/J, Dairy Sci. vol. 82, Suppl. Feb. 1999 pp. 213-220.

Peters D., The LLNL high-speed sorter: Design features,operational characteristics, and bioloical utility, Cyometry, 6:290-301 (1985).

Rens W., et al Slit-scan flow cytometry for consistent high resdolution Dna analysis of X- and Y- chromosome bearing sperm, Cytometry 25:191-199 (1996).

van Munster, E. B. Interferometry in flor to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/Isrll.htm, pp. 14, May 11, 2004.

Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.

Blecher, S.R., et al. A new approach to immunological sexing of sperm, Theriogenology, 59, pp. 1309-1321, 1999 Vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen recepters (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, 65 (2006) 943-957.

Habermann F. A., et al., Validation of sperm sexing in the cattle (Bos taurus) by dual colour flourescence in situ hybridization; J Anim Breed Genet. Apr. 2005; 122 Suppl 1:22-7 (Abstract only).

Johnson, L. A., Sexing mammalian sperm for production of offspring: the state-of-the-art; Animal Reproduction Science; 60-61 (2000) pp. 93-107.

Seidel, G.E. Jr., et al., Methods of Ovum Recovery and Factors Affecting Fertilization of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

SEPARATION SYSTEMS OF FROZEN-THAWED SPERMATOZOA INTO X-CHROMOSOME BEARING AND Y-CHROMOSOME BEARING POPULATIONS

This application is a continuation of U.S. patent application Ser. No. 10/433,183 filed May 29, 2003, which is a national stage of International Application No. PCT/US01/45023, filed Nov. 29, 2001, which claims benefit of U.S. Provisional Patent Application No. 60/253,787, filed Nov. 29, 2000 and U.S. Provisional Patent Application No. 60/253,785, filed Nov. 29, 2000, each hereby incorporated by reference herein.

I. TECHNICAL FIELD

The invention involves the substantially uniform binding of fluorochrome(s) to the DNA within mammalian spermatozoa (or sperm cells) allowing such labeled spermatozoa to be separated into high purity X-chromosome bearing and Y-chromosome bearing populations. Specifically, methods for the substantially uniform binding of fluorochrome(s) to the DNA of mammalian spermatozoa contained within previously frozen and then thawed semen. In addition, the invention further involves devices, methods, and compositions for the use of high purity separated X-chromosome bearing and Y-chromosome bearing populations of spermatozoa from previously frozen-thawed semen in processes involving, but not limited to, artificial insemination, surgical insemination, and in-vitro fertilization and embryo culturing techniques.

II. BACKGROUND

Sperm can be collected from a great variety of mammals and then separated into X-chromosome bearing and Y-chromosome bearing populations based upon the difference in DNA content. In some conventional methods of spermatozoa separation, the DNA content of the spermatozoa to be separated can be stained with a fluorochrome(s) that upon excitation emit(s) a measurable amount of fluorescence. Because X-chromosome bearing spermatozoa contain a greater amount of DNA than Y-chromosome bearing spermatozoa, each X-chromosome bearing spermatozoa has the capacity to bind a relatively greater amount of fluorochrome than the corresponding Y-chromosome bearing spermatozoa. Comparison of the relative magnitude of emitted fluorescence upon excitation of the fluorochrome(s) allows the isolation of X-chromosome bearing spermatozoa from Y-chromosome bearing spermatozoa as described by U.S. Pat. No. 5,135,759, hereby incorporated by reference.

Even though X-chromosome bearing spermatozoa and Y-chromosome bearing spermatozoa have been differentiated by and separated based upon the difference in emitted fluorescence for many years, and even though there is large commercial market for isolated populations of X-chromosome bearing spermatozoa and Y-chromosome bearing spermatozoa, there remain significant problems yet to be resolved.

A significant problem with conventional methods of separating X-chromosome bearing spermatozoa from Y-chromosome bearing spermatozoa can be that each resulting population contains a significant number of incorrectly separated spermatozoa that belong in the other population. This problem in differentiating between spermatozoa can, in part, be attributed to the lack of uniformity in the amount of fluorochrome bound to the spermatozoal DNA. As such, a range in the amount of fluorochrome bound by X-chromosome bearing spermatozoa is generated and a range in the amount of fluorochrome bound by Y-chromosome bearing spermatozoa is generated. When these ranges in the amount of fluorochrome overlap or yield some values that are similar, it can be difficult or impossible to classify those individual spermatozoa to one population or the other with any degree of certainty and cross contamination of the populations can occur.

This particular problem can be exacerbated with regard to spermatozoa obtained from frozen and subsequently thawed mammalian semen. The mean purity for separated Y-chromosome bearing spermatozoa population derived from previously frozen-thawed semen can be 85% or less, and the mean purity for separated X-chromosome bearing spermatozoa population derived from previously frozen-thawed semen can be 82% or less.

Another significant problem associated with staining of spermatozoal DNA can be the detrimental effects on fertilization rates and subsequent embryonic development of fertilized oocyte(s) (oocyte, ootid, or ovum, or a plurality of same, as may be appropriate within a specific application). One aspect of this problem may be that the amount of stain bound to the DNA may effect the viability of the spermatozoa resulting in lower fertilization rates. Another aspect of this problem can be that the amount of time that elapses during the staining of the DNA may effect the viability of the sperm resulting in lower fertilization rates. Another aspect of this problem may be that the amount of time that elapses during staining of the DNA may lower subsequent cleavage rates of oocytes fertilized with such stained spermatozoa. A 20% decline in cleavage rates have been observed for oocytes when staining time requires 190 minutes as compared to when staining time requires 60 minutes. Another aspect of this problem may be that the percent of oocytes fertilized with stained spermatozoa that proceed to blastulation may be lower as described in the journal article entitled "In vitro Fertilization with Flow-Cytometrically-Sorted Bovine Sperm", Theriogenology 52: 1393-1405 (1999), hereby incorporated by reference herein.

Another significant problem may be that cryopreserved sperm may demonstrate increased capacitation, and the length of time such spermatozoa are viable may be shortened. As such, if previously frozen spermatozoa are to be separated into X-chromosome bearing and Y-chromosome bearing populations that are to be subsequently used in applications such as in-vitro fertilization, in-vivo artificial insemination, or the like, then routine staining procedures may have to be abbreviated to maintain suitable number of viable sperm cells.

As relating to the problems of staining spermatozoa uniformly, even when spermatozoa are obtained from previously frozen-thawed semen; maintaining sperm viability; separating stained spermatozoa into X-chromosome bearing and Y-chromosome bearing populations, even when the spermatozoa being separated are obtained from previously frozen semen; generating populations of X-chromosome bearing and Y-chromosome bearing spermatozoa having high purity; and successfully using separated spermatozoa for artificial insemination, surgical insemination, and in-vitro fertilization techniques it can be understood there are significant problems with conventional technology which are addressed by the instant invention.

III. DISCLOSURE OF THE INVENTION

A broad object of embodiments of the invention can be to provide DNA staining technology that allows substantially uniform amounts of fluorochrome to be bound to the DNA of all individual spermatozoa bearing an X-chromosome and substantially uniform amounts of fluorochrome to be bound to all individual spermatozoa bearing a Y-chromosome within an amount of semen.

One aspect of this broad object of the invention can be to narrow the range in magnitude of emitted fluorescence for each of the X-chromosome bearing population and the Y-chromosome bearing population of spermatozoa upon passing through a fluorochrome excitation source.

Another aspect of this broad object of the invention can be to increase the difference between the mean values of magnitude of emitted fluorescence for each of the X-chromosome bearing population and the Y-chromosome bearing population of spermatozoa upon passing through a fluorochrome excitation source.

Another aspect of this broad object of the invention can be to decrease the number of spermatozoa incorrectly assigned to each of the X-chromosome bearing population and the Y-chromosome bearing population of spermatozoa.

Another aspect of this broad object of the invention can be to generate separate X-chromosome bearing and Y-chromosome bearing populations having greater than 85% purity or greater than 86%, 87%, 88%, 89%, 90%, 91%, 92%, 93%, 94%, 95%, 96%, 97%, 98%, or even 99% purity.

Another broad object of embodiment of the invention can be to allow assessment of a wide range of genetics. Rather than being limited to the genetics of individuals from species of mammals having proximity to a spermatozoa separating or sorting facility, genetics representing a wide variety of individuals from numerous species can be transported as frozen semen to distant spermatozoa separation facilities for subsequent separation into X-chromosome bearing and into Y-chromosome bearing populations. These species of mammals may include, but are not limited to primates, such as chimpanzees, gorillas, humans, or the like; marine mammals, such as whales, porpoises, or the like; bovids; ovids; swine; canids; felids; or equids, as but a few examples. It may also include genetics that are considered rare because the species of mammal may be endangered or few in number; or considered rare because the individual has desirable morphological, physiological, or intellectual attributes.

Another broad object of embodiments of the invention can provide separation technology for differentiating between X-chromosome bearing and Y-chromosome bearing spermatozoa obtained from frozen-thawed semen.

Another object of embodiments of the invention can be to provide DNA staining technology to more uniformly stain the DNA of spermatozoa contained in frozen-thawed semen to improve the apparent resolution between X-chromosome bearing and Y-chromosome bearing spermatozoa.

Another object of embodiments of the invention can be to provide high purity artificial insemination samples prepared from separated spermatozoa from frozen-thawed semen.

Another object of embodiments of the invention can be to provide high purity low dose artificial insemination samples prepared from separated spermatozoa from frozen-thawed semen.

Another object of embodiments of the invention can be to provide high purity insemination samples for surgical insemination procedures prepared from separated spermatozoa from frozen-thawed semen.

Another object of an embodiment of the invention can be to provide high purity insemination samples for in-vitro fertilization procedures prepared from separated spermatozoa from frozen-thawed semen.

Another object of an embodiment of the invention can be to provide high purity insemination samples for in-vitro fertilization procedures prepared from separated spermatozoa from frozen-thawed human semen.

Another object of an embodiment of the invention can be to provide technology for staining and separation of spermatozoa from frozen-thawed sperm into X-chromosome bearing populations and Y-chromosome bearing populations for in-vitro fertilization of oocyte(s) that is not detrimental to cleavage rates or embryonic development.

Naturally further objects of the invention are disclosed throughout other areas of specification.

IV. BRIEF DESCRIPTION OF THE DRAWINGS

V. MODE(S) FOR CARRYING OUT THE INVENTION

Figure 1:
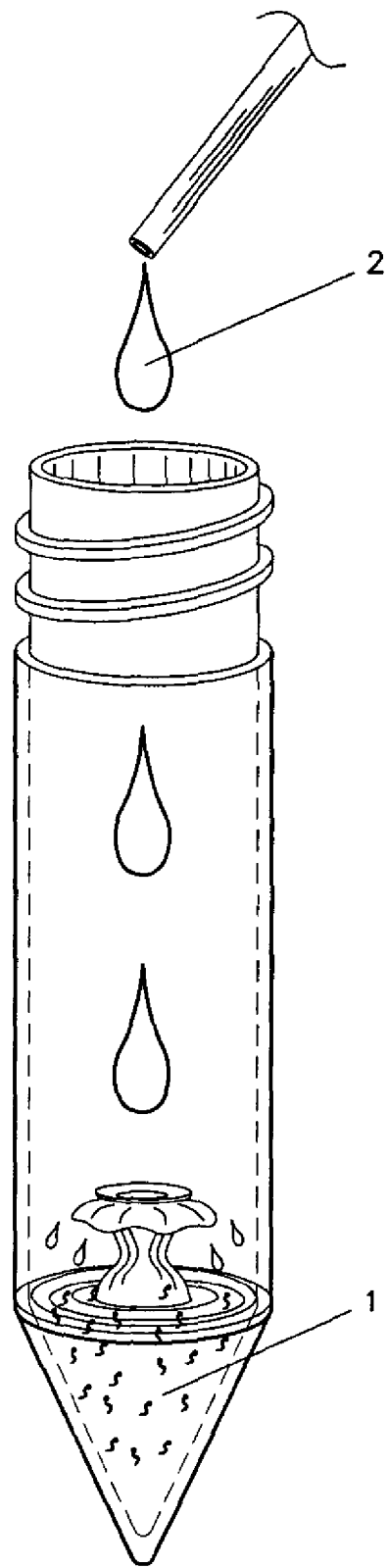
FIG. 1 shows a particular embodiment of the invention for staining the DNA of spermatozoa contained in frozen-thawed semen.

To routinely separate spermatozoa (live, fixed, viable, non-viable, or nuclei) into high purity X-chromosome bearing samples and into Y-chromosome bearing samples, the method used to sort the X-chromosome bearing and Y-chromosome bearing spermatozoa must provide sufficient resolution of the X-chromosome bearing spermatozoa from the Y-chromosome bearing spermatozoa so that separation or sorting step(s) can be achieved without substantial cross contamination.

Resolution or differentiation of spermatozoa can be based upon ascertaining the difference in the fluorescent emission from the amount of fluorochrome bound to the DNA within the X-chromosome bearing spermatozoa upon excitation and the fluorescent emission from the amount of fluorochrome bound to the DNA within the Y-chromosome bearing spermatozoa upon excitation. Separation of X-chromosome bearing spermatozoa and Y-chromosome bearing spermatozoa based upon this measurable difference may then be achieved by a number of methods such as flow cytometry, liquid chromatography, gel electrophoresis, and other technologies that similarly compare the relative magnitude of fluorescence to differentiate between X-chromosome bearing spermatozoa and the Y-chromosome bearing spermatozoa.

Spermatozoa separation systems can have problems differentiating between the fluorescent emission generated by the fluorochrome bound to the DNA of X-spermatozoa, and the fluorescent emission generated by the fluorochrome bound to the DNA of Y-spermatozoa upon excitation when the amount of the fluorochrome bound to the DNA of individual spermatozoa is not consistent within the Y-chromosome bearing or X-chromosome bearing populations. These difficulties in differentiating between the amount of fluorescent emissions generated by the bound fluorochrome(s) become exacerbated when spermatozoa are obtained from frozen-thawed sperm which are stained by conventional techniques.

The failure to stain the spermatozoal DNA consistently can generate a broader range of fluorescing species for both X-chromosome bearing and Y-chromosome bearing populations of spermatozoa. This broader range of fluorescing species for the two populations results in an increased range of apparent DNA molecular weights and a decreased ability to resolve X-chromosome bearing from Y-chromosome bearing spermatozoa. The decrease in resolution makes separation of the X-chromosome bearing spermatozoa from the Y-chromosome bearing spermatozoa more difficult and results in cross contamination between populations and a lower purity of separated spermatozoa samples are obtained.

Particular embodiments of the invention provide technology to stain the DNA of live viable spermatozoa or the spermatozoal DNA of frozen-thawed semen specimens to allow increased resolution of X-chromosome bearing from the Y-chromosome bearing spermatozoa resulting in high purity X-chromosome bearing and high purity Y-chromosome bearing populations of sperm cells. As such, it is understood that the term high purity can mean greater resolution of the X-chromosome bearing from the Y-chromosome bearing spermatozoa compared to conventional staining technology for a given application. High purity can also mean less cross contamination between separated spermatozoa populations compared to conventional separation technologies.

For example, in particular flow cytometry embodiments of the invention, high purity for stained frozen-thawed live spermatozoa can mean sorted populations of X-chromosome bearing spermatozoa and Y-chromosome bearing spermatozoa having a purity greater than about 85%. However, if live viable sperm or sperm nuclei are being sorted high purity may mean X-chromosome bearing and Y-chromosome bearing populations having a purity greater than about 90%. As can be understood, the definition of high purity is contextual involving a comparison of the results obtained from each embodiment of the invention compared to the results obtained when utilizing convention technologies for a particular application. In the context of spermatozoa having DNA that stains poorly, such as previously frozen-thawed spermatozoal DNA, high purity can mean populations of isolated spermatozoa bearing greater than 85%, 86%, 87%, 88%, 89%, 90%, 91%, 92%, 93%, 94%, 95%, 96%, 97%, 98%, or 99% of either an X-chromosome or a Y-chromosome.

Embodiments of the invention can include spermatozoa collected from numerous species of male mammals, and the invention should be understood not to be limited to the species of male mammals described by the specific examples within this application. Rather the specific examples within this application are intended to be illustrative of the varied and numerous species of male mammals from which semen can be collected and utilized in certain embodiments of the invention. Embodiments of the invention, for example, may include the spermatozoa of animals having commercial value for meat or dairy production such as swine, ovids, bovids, equids, buffalo, or the like (naturally the mammals used for meat or dairy production may vary from culture to culture). It may also include the spermatozoa of various domesticated mammalian species encompassed by canids and felids. It may also include spermatozoa from individuals of various mammalian species that have uncommon attribute(s), such as morphological characteristics including weight, size, or conformation, or other desired characteristics such as speed, agility, intellect, or the like. It may also include spermatozoa of primates, including but not limited to chimpanzees, gorillas, or humans and the spermatozoa from marine mammals such as whales and dolphins. It may also include frozen-thawed spermatozoa from all the various mammals above-described and further, including but not limited to, the spermatozoa of deceased donors, from rare or exotic mammals, zoological specimens, or endangered species.

Now referring primarily to FIG. 1, particular embodiments of the invention can comprise semen containing spermatozoa (1) collected from a male mammal, including but not limited to, those above-described. The spermatozoa can be incubated in a concentration of Hoechst 33342 stain (2) of greater than about 40 μM at a temperature between about 30° Centigrade and about 40° Centigrade for a duration of time between 50 minutes to 200 minutes to stain spermatozoal DNA with sufficient uniformity to allow X-chromosome bearing spermatozoa to be differentiated from Y-chromosome bearing spermatozoa based upon the magnitude of fluorescence at a rate greater than about 85%.

The concentration of Hoechst 33342 stain between 40 μM and 2500 μM, the temperature between 30° Centigrade and about 40° Centigrade, and the duration of time between 50 minutes and 200 minutes can be selected to adjust the purity of the separated X-chromosome bearing and Y-chromosome bearing populations, or can be selected to promote cleavage rates and embryonic development, as further discussed below.

For example, when staining spermatozoal DNA from certain bovine species, the concentration of Hoechst 33342 can be increased to between about 200 μM and about 2500 μM, incubated for a period of time between about 60 minutes to about 190 minutes at a temperature of about 37° Centigrade. Specifically with respect to certain frozen-thawed bovine spermatozoa, the Hoechst 33342 stain (2) can be adjusted to establish a concentration of 2240 μM and then incubated for about 60 minutes at about 39° Centigrade.

With respect to the cleavage rates of oocytes inseminated with mammalian sperm cells treated according to the invention, the increase in stain concentration up to at least 2240 μM does not appear to have a depressive effect on either cleavage or embryonic development. Higher stain concentrations may actually be beneficial with respect to certain embodiments of the invention because the length of incubation time may be decreased improving percent cleavage or blastocyst formation. From application to application the concentration of Hoechst 33342, the length of incubation time, or both can be adjusted to obtain the maximal cleavage rate and blastocyst formation, if desired.

Figure 2:
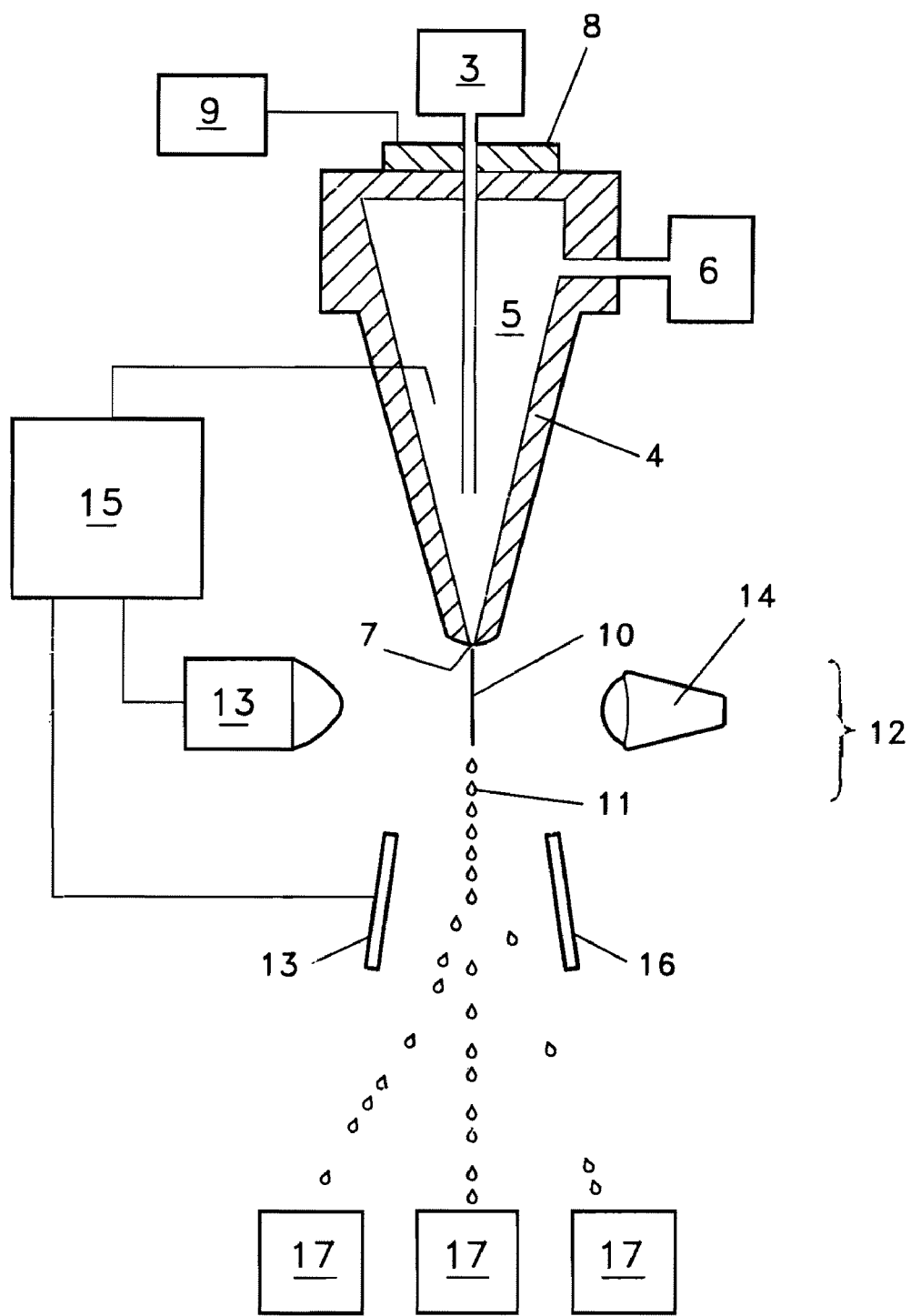
FIG. 2 shows a particular embodiment of the invention for separating spermatozoa from frozen-thawed semen into X-chromosome bearing and Y-chromosome bearing spermatozoa.
Figure 3:
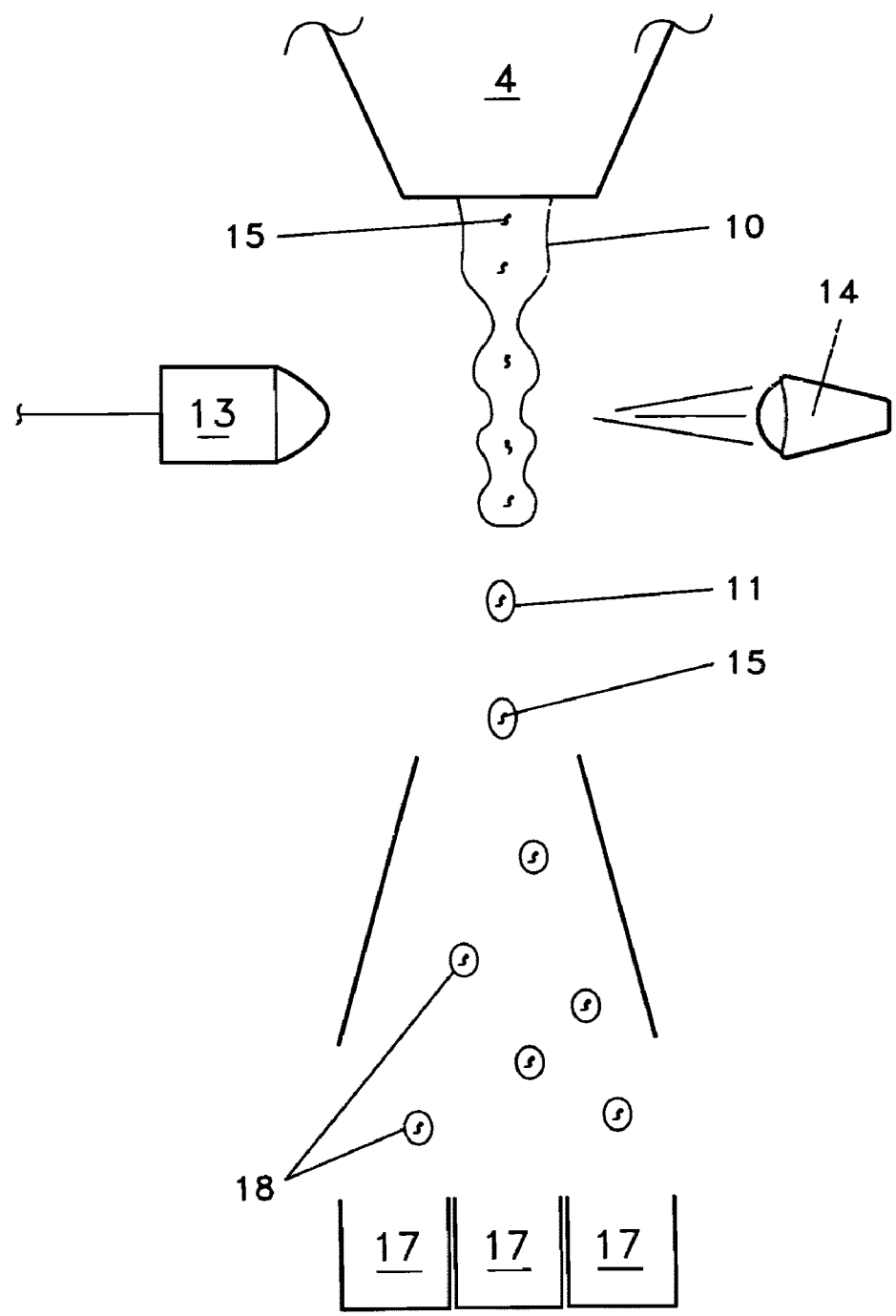
FIG. 3 shows a further view of a particular embodiment of the invention for separating spermatozoa from frozen-thawed semen into X-chromosome bearing and Y-chromosome bearing spermatozoa.

Now referring primarily to FIGS. 2 and 3, flow cytometric embodiments of the invention can include a cell source (3) which acts to establish or supply stained spermatozoa (fresh, frozen-thawed, sperm nuclei, or the like) to be analyzed by flow cytometry. The cells are deposited within a nozzle (4) in a manner such that the stained sperm cells are surrounded by a sheath fluid (5). The sheath fluid (5) is usually supplied by a sheath fluid source (6) so that as the cell source (3) supplies sperm cells, the sheath fluid (5) is concurrently fed through the nozzle (4). In this manner the sheath fluid (5) forms a sheath fluid environment for the sperm cells. Since the various fluids are provided to the flow cytometer at some pressure, they flow out of the nozzle (4) and exit at the nozzle orifice (7). By providing a type of oscillator (8) which may be very precisely controlled through an oscillator control (9), pressure waves may be established within the nozzle (4) and transmitted to the fluids exiting the nozzle (4) at the nozzle orifice (7). Since the oscillator (9) acts upon the sheath fluid (5), the stream (10) exiting the nozzle orifice (7) eventually and regularly forms drops (11). Because the sperm cells are at least partially surrounded by a sheath fluid environment, the drops (11) can contain within them individually isolated sperm cells.

Since the drops (11) generally contain individual isolated sperm cells, the flow cytometer can distinguish and separate droplets based upon the magnitude of fluorescence emitted from the fluorochrome bound to the spermatozoal DNA. This is accomplished through a cell sensing system (12). The cell sensing system involves at least some type of sensor (13) which responds to the magnitude of fluorescence emitted by each sperm cell contained within each drop (11). The sperm cell sensing system (13) may cause an action depending upon the relative presence or relative absence of fluorescence emitted by the bound fluorochrome upon excitation by some stimulant such as the laser exciter (14). While each spermatozoon can be stained by the fluorochrome, such as Hoechst 33342, as described above, the differing amount of DNA comprising the X-chromosome and the Y-chromosome causes different amounts of stain to be bound. Thus, by sensing the degree of fluorescence emitted by the fluorochrome upon excitation it is possible to discriminate between X-bearing spermatozoa and Y-bearing spermatozoa by their differing emission levels.

In order to achieve separation and isolation of the appropriate sperm cells, the signals received by sensor (14) are fed to some type of sorter discrimination system (15) which very rapidly makes a differentiation decision and can differentially charge each drop (11) based upon whether it has decided that the desired sperm cell does or does not exist within that drop (11). In this manner the separation or discrimination system (15) acts to permit the electrostatic deflection plates (16) to deflect drops (11) based on whether or not they contain the appropriate sperm cell. As a result, the flow cytometer acts to sort cells by causing them to land in one or more collectors or containment elements (17). Thus by sensing some property of the sperm cells (such as magnitude of fluorescence), the flow cytometer can discriminate between sperm cells based on that particular characteristic and place them in the appropriate collector or containment element (17). In particular embodiments of the invention using flow cytometry to sort spermatozoa, the X-bearing sperm cell containing droplets are charged positively and thus deflect in one direction, and the Y-bearing sperm cell containing droplets are charged negatively and thus deflect the other way, and the wasted stream (containing unsortable sperm cells) remain uncharged and thus can be collected in an undeflected stream into a suction tube, or the like.

Now referring primarily to FIG. 3, the nozzle (4) emits a stream (10) which because of the oscillator (8) (not shown in FIG. 3) forms drops (11). Since the sperm cell source (3) (not shown in FIG. 3) may supply sperm cells (1) which may be stained according to the above-described invention, the light emission from the bound fluorochrome excited by laser exciter (13) can be differentially determined by sensor (14) so that the existence or nonexistence of a charge on each drop (11) as it separates from stream (10) can be controlled by the flow cytometer. This control results in positively charged, negatively charged, or uncharged drops (8) based upon the sperm cell contained within each drop (11). As shown by FIG. 3, certain drops are shown as deflected drops (18). These deflected drops (18) are those containing spermatozoon differentiated by bearing either an X-chromosome or a Y-chromosome. Separated spermatozoa are then isolated in an appropriate collection element or containment element (17) for later use.

Embodiments of the invention can comprise droplets (11) each containing a sperm cell (15) bearing either an X-chromosome or a Y-chromosome. Droplets containing X-chromosome bearing sperm cells can be isolated into containment element(s) (17) at a rate of at least 1000 per second or at a rate greater than about 1000 per second, such as 2000 per second, 3000 per second, 4000 per second, 5000 per second, or higher. Similarly Y-chromosome bearing sperm cells can be isolated at a rate of at least 1000 per second or at a rate greater than about 1000 per second, such as 2000 per second, 3000 per second, 4000 per second, 5000 per second, or higher. In some embodiments of the invention, droplets containing X-chromosome bearing sperm cells and droplets containing Y-chromosome bearing sperm cells are simultaneously separated and isolated into containment elements each at a rate of at least 1000 per second, or greater than 1000 per second, such as 2000 per second, 3000 per second, 4000 per second, 5000 per second, or at even higher rates.

Embodiments of the invention can also include artificial insemination samples prepared from sperm cells collected from male mammals (which can be frozen and thawed with respect to some embodiments of the invention) that are then stained and separated according to embodiments of the invention above-described. The artificial insemination samples can then be utilization in artificial insemination protocols. For example, a bovine artificial insemination sample prepared from separated spermatozoa according to the invention can comprise fewer than $10 \times 10^6$ viable spermatozoa contained within a straw. Low dose artificial insemination samples for bovine artificial insemination can contain as few as $1-3 \times 10^6$ viable spermatozoa, or even as few as 150,000 spermatozoa as described in U.S. patent application Ser. No. 09/001,394, or PCT Patent Application US98/27909, each hereby incorporated by reference. Artificial insemination samples, having a regular number of separated sperm cells or a low dose of separated sperm cells can be used in animal breeding programs, such as those described in U.S. Patent Applications 60/224,050 and 60/21,093, each hereby incorporated by reference. Artificial insemination samples containing previously frozen and thawed spermatozoa stained and separated according to the invention can also be utilized in conjunction with synchronized breeding programs using superovulated animals as described in U.S. patent application Ser. No. 09/001,454, hereby incorporated by reference herein. Naturally, for frozen sperm cells that are of limited availability because the male mammal is deceased, or the male mammal is a rare or exotic animal, an artificial insemination sample prepared according to the invention may contain even fewer spermatozoa.

The number of viable separated spermatozoa that are stained, separated, and isolated into X-chromosome bearing or Y-chromosome bearing populations according to the invention that are used in an artificial insemination sample can vary based upon the species of mammal to be artificially inseminated. For example, equine artificial insemination samples prepared from separated spermatozoa may require a higher number of viable separated spermatozoa relative to the bovine application, as described in PCT Patent Application US99/17165, hereby incorporated by reference. An embodiment of an equine insemination sample may, as but one example, contain between about forty million to about one-hundred million spermatozoa.

In certain embodiments of the invention, the insemination sample containing separated spermatozoa collected from a male mammal or obtained from frozen-thawed sperm may be packaged for use with surgical insemination procedures Sperm cells stained, separated, or isolated according to the invention can also be used to fertilize oocyte(s) in-vitro (IVF). An attractive feature of IVF can be that fewer separated sperm are need than for artificial insemination. It may be desirable to use the fewest sperm possible, especially if the male mammal is deceased, rare, or exotic or if the spermatozoa are stained or separated in accordance with various embodiments of the invention. Also, commercial availability of sperm cells separated into X-chromosome bearing and Y-chromosome bearing populations, especially when the male mammal is located a distance from the female mammal, or is exotic, rare, or has desirable attributes, will likely result in greatly expanded use of IVF in breeding programs. Certain embodiments of the invention can include devices and methodologies for the use of separated spermatozoa, including but not limited to frozen-thawed sperm cells, with respect to the in-vitro fertilization of oocytes, the in-vitro oocyte maturation, or the in-vitro culture of zygotes, such as those described in the journal article by Lu, K. H., Cran D. G., and Seidel, G. E., *In-vitro Fertilization With Flow Cytometrically-Sorted Bovine Sperm*, Theriogenology, 52, 1393-1405 (1999), hereby incorporated by reference.

Certain embodiments of the invention involving the production or generation of mammalian embryos can comprise collection of semen (1) from a male mammal or obtaining semen or spermatozoa (1) that are or have been previously frozen. According to embodiments of the invention described above, the semen is combined with Hoechst 33342 (2) stain to establish a concentration of between 40 μM and 2500 μM. The sperm cells are incubated with the Hoechst 33342 stain at a temperature between about 30° Centigrade and about 40° Centigrade for a duration of between about 50 minutes to about 200 minutes. The stained sperm cells may be separated and isolated into X-chromosome bearing and Y-chromosome bearing populations according to embodiments of the invention described above or by other sperm cell separation techniques that also differentiate X-chromosome bearing spermatozoa from Y-chromosome bearing spermatozoa based upon the magnitude of fluorescence. The isolated sperm cells may then be used to fertilize oocytes from a female mammal of the same species, and in some cases from female mammals of different species, in-vitro.

As an example of an application of embodiments of the invention involving frozen bull sperm in IVF applications, sperm samples from two bulls were stained either at a concentration of 224 μM or 2,240 μM of Hoechst 33342 and the stained spermatozoa were then bulk sorted on a flow cytometer at 1000 sperm/sec into 2% egg yolk citrate. Spermatozoa were inseminated at $1\times10^6$/mL and embryos were cultured in the mSOF system described by Tervit H. R. et al., *Successful Culture In-Vitro of Sheep and Cattle Ova*, J. Reprod. Fertil., 30:493-497 (1992), hereby incorporated by reference. Three replicates were carried out for bull 1 and one replicate for bull 2 (Table 1). With conventional procedures, blastocyst production with separated spermatozoa can be 70-90% of controls with spermatozoa that have not been separated. For example, development to blastocyst has been shown to be 17% with bovine oocytes inseminated with separated spermatozoa, compared with >25% which might be expected with IVF using unseparated spermatozoa.

TABLE 1

Effect of stain concentration on cleavage and developmental rates of oocytes inseminated with separated stained spermatozoa from frozen-thawed sperm.

| Bull | No. E-jacu-lates | Hoechst 33342 conc. (μM) | Staining time required (min) | No. oocytes | % cleave | % blastocysts/oocyte |
|---|---|---|---|---|---|---|
| 1 | 3 | 224 | 190 | 368 | 44[a] | 17 |
| 1 | 3 | 2240 | 60 | 373 | 60[b] | 23 |
| 2 | 1 | 224 | 190 | 86 | 23[a] | 0[a] |
| 2 | 1 | 2240 | 60 | 81 | 42[b] | 16[b] |

[a,b]Percentages within bulls within columns with different superscripts differ (P < .025, $\chi^2$)

As can be understood, it can take much longer to stain frozen-thawed sperm so that they can be resolved during separation at the lower stain concentration than at 10× stain concentration. The differences observed in cleavage rates between the two stain concentrations most likely can be attributed to the extended incubation time at the lower stain level. It appears that a 10-fold increase in stain concentration does not have depressive effect on either cleavage of embryonic development.

As can be easily understood from the foregoing, the basic concepts of the present invention may be embodied in a variety of ways. It involves the staining of spermatozoa, whether fresh spermatozoa or frozen-thawed spermatozoa, separation and isolation techniques which may be used with such stained spermatozoa, as well as devices to accomplish the staining, separation, and isolation of such stained spermatozoa into X-chromosome bearing and Y-chromosome bearing populations. In this patent application, the staining and separating techniques used with spermatozoa are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this patent application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in functionally-oriented terminology, each aspect of the function is accomplished by a device, subroutine, or program. Apparatus claims may not only be included for the devices described, but also method or process claims may be included to address the functions the invention and each element performs. Neither the description nor the terminology is intended to limit the scope of the claims which now be included.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sorter" should be understood to encompass disclosure of the act of "sorting"—whether explicitly discussed or not—and, conversely, were there only disclosure of the act of "sorting", such a disclosure should be understood to encompass disclosure of a "sorter" and even a "means for sorting".

Such changes and alternative terms are to be understood to be explicitly included in the description. Additionally, the various combinations and permutations of all elements or applications can be created and presented. All can be done to optimize the design or performance in a specific application.

Any acts of law, statutes, regulations, or rules mentioned in this application for patent: or patents, publications, or other references mentioned in this application for patent are hereby incorporated by reference. Specifically, U.S. Provisional Patent Application No. 60/253,787, filed Nov. 29, 2000, U.S. Provisional Patent Application No. 60/253,785, filed Nov. 29, 2000, International Patent Application No. PCT/US01/45023 filed Nov. 29, 2001 and U.S. application Ser. No. 10/433,183 filed May 5, 2003 are hereby incorporated by reference including any figures or attachments, and each of references in the following table of references are hereby incorporated by reference.

US Patent Documents

| DOCUMENT NO. | DATE | NAME | CLASS | SUBCLASS | FILING DATE |
|---|---|---|---|---|---|
| 32,350 | Feb. 10, 1987 | Bhattacharya | | | Nov. 22, 1974 |
| 3,687,806 | Aug. 29, 1972 | Van den Bovenkamp | 195 | 1.3 | Nov. 4, 1969 |
| 3,829,216 | Aug. 13, 1974 | Persidsky | 356 | 36 | Oct. 2, 1972 |
| 3,894,529 | Jul. 15, 1975 | Shrimpton | 128 | 1 R | Apr. 10, 1969 |
| 4,009,260 | Feb. 22, 1977 | Ericsson | 424 | 105 | Dec. 11, 1974 |
| 4,067,965 | Jan. 10, 1978 | Bhattacharya | 424 | 105 | Dec. 17, 1975 |
| 4,083,957 | Apr. 11, 1978 | Lang | 424 | 78 | Feb. 4, 1976 |
| 4,085,205 | Apr. 18, 1978 | Hancock | 424 | 105 | Jan. 24, 1977 |
| 4,092,229 | May 30, 1978 | Bhattacharya | 204 | 180 R | Oct. 20, 1976 |
| 4,155,831 | May 22, 1979 | Bhattacharya | 207 | 299 R | Feb. 23, 1978 |
| 4,191,749 | Mar. 4, 1980 | Bryant | 424 | 105 | Oct. 11, 1977 |
| 4,225,405 | Sep. 30, 1980 | Lawson | 204 | 180 R | Aug. 16, 1978 |
| 4,276,139 | Jun. 30, 1981 | Lawson | 204 | 180 R | Oct. 9, 1979 |
| 4,339,434 | Jul. 13, 1982 | Ericsson | 424 | 105 | Aug. 17, 1981 |
| 4,362,246 | Dec. 7, 1982 | Adair | 209 | 3.3 | Jul. 14, 1980 |
| 4,448,767 | May 15, 1984 | Bryant | 424 | 85 | Feb. 15, 1980 |
| 4,474,875 | Oct. 2, 1984 | Shrimpton | 435 | 002 | Aug. 18, 1980 |
| 4,501,366 | Feb. 26, 1985 | Thompson | 209 | 556 | Dec. 14, 1982 |
| 4,511,661 | Apr. 16, 1985 | Goldberg | 436 | 503 | Dec. 30, 1983 |
| 4,605,558 | Aug. 12, 1986 | Shrimpton | 424 | 561 | Apr. 20, 1984 |
| 4,660,971 | Apr. 28, 1987 | Sage et al. | 356 | 39 | May 3, 1984 |
| 4,680,258 | Jul. 14, 1987 | Hammerling et al | 435 | 7 | Aug. 9, 1983 |
| 4,673,288 | Jun. 16, 1987 | Thomas et al. | | | |
| 4,683,195 | Jul. 28, 1997 | Mullis et al | | | |
| 4,683,202 | Jul. 28, 1987 | Mullis | | | |
| 4,698,142 | Oct. 6, 1987 | Muroi et al | 204 | 182.3 | Jul. 31, 1985 |
| 4,749,458 | Jun. 7, 1988 | Muroi et al | 204 | 182.3 | Mar. 2, 1987 |
| 4,790,653 | Dec. 13, 1988 | North, Jr. | | | |
| 4,988,619 | Jan. 29, 1991 | Pinkel | 435 | 30 | Nov. 30, 1987 |
| 4,999,283 | Mar. 12, 1991 | Zavos et al | 435 | 2 | Aug. 18, 1989 |
| 5,021,244 | Jun. 4, 1991 | Spaulding | 424 | 561 | May 12, 1989 |
| 5,055,393 | Oct. 8, 1991 | Kwoh et al | | | |
| 5,135,759 | Aug. 4, 1992 | Johnson | 424 | 561 | Apr. 26, 1991 |
| 5,346,990 | Sep. 13, 1994 | Spaulding | 530 | 350 | Mar. 12, 1991 |
| 5,371,585 | Dec. 6, 1994 | Morgan et al. | 356 | 246 | Nov. 10, 1992 |
| 5,437,987 | Aug. 1, 1995 | Ten et al | | | |
| 5,439,362 | Aug. 8, 1995 | Spaulding | 424 | 185.1 | Jul. 25, 1994 |
| 5,461,145 | Oct. 24, 1995 | Kudo et al | | | |
| 5,466,572 | Nov. 14, 1995 | Sasaki et al. | 435 | 2 | Apr. 25, 1994 |
| 5,480,774 | | | | | |
| 5,483,469 | Jan. 9, 1996 | Van den Engh et al. | 364 | 555 | Aug. 2, 1993 |
| 5,494,795 | Feb. 27, 1996 | Guerry et al. | 435 | 6 | May 5, 1993 |
| 5,503,994 | Apr. 2, 1996 | Shear et al. | 436 | 90 | Oct. 8, 1993 |
| 5,578,449 | Nov. 26, 1996 | Frasch et al. | 435 | 6 | Apr. 20, 1995 |
| 5,514,537 | May 7, 1996 | Chandler | 435 | 002 | Nov. 28, 1994 |
| 5,589,457 | Dec. 31, 1996 | Wiltbank | 514 | 12 | Jul. 3, 1995 |
| 5,602,039 | Feb. 11, 1997 | Van den Engh | 436 | 164 | Oct. 14, 1994 |
| 5,602,349 | Feb. 11, 1997 | Van den Engh | 73 | 864.85 | Oct. 14, 1994 |
| 5,622,820 | Apr. 11, 1997 | Rossi | 435 | 5 | Nov. 3, 1994 |
| 5,641,457 | Mar. 9, 1999 | Tomiyama et al. | 250 | 207 | Jun. 16, 1997 |
| 5,643,796 | Jul. 1, 1997 | Van den Engh et al | 436 | 50 | Oct. 14, 1994 |
| 5,660,997 | Aug. 26, 1997 | Spaulding | 435 | 7.21 | Jun. 7, 1995 |
| 5,690,895 | Nov. 25, 1997 | Matsumoto et al. | 422 | 73 | Dec. 6, 1996 |
| 5,700,692 | Dec. 23, 1997 | Sweet | 436 | 50 | Sep. 27, 1994 |
| 5,726,364 | Mar. 10, 1998 | Van den Engh | 73 | 864.85 | Feb. 10, 1997 |
| 5,819,948 | Oct. 13, 1998 | Van den Engh | 209 | 158 | Aug. 21, 1997 |
| 5,876,942 | Mar. 2, 1999 | Cheng et al | 435 | 6 | Jul. 24, 1997 |
| 5,880,457 | Mar. 9, 1999 | Tomiyama et al. | 250 | 207 | Jun. 16, 1997 |
| 5,985,216 | Nov. 16, 1999 | Rens, et al. | 422 | 073 | Jul. 24, 1997 |
| 6,071,689 | Jun. 6, 2000 | Seidel et al. | 435 | 2 | Jan. 29, 1998 |

Foreign Patent Documents

| DOCUMENT NO | DATE | COUNTRY |
| --- | --- | --- |
| WO 96/12171 | Oct. 13, 1995 | United States |
| WO 98/34094 | Jun. 8, 1998 | NZ |
| WO 99/05504 | Jul. 24, 1998 | US |
| WO 99/33956 | Aug. 7, 1999 | US |
| WO 99/38883 | May 8, 1999 | US |

-continued

| DOCUMENT NO | DATE | COUNTRY |
| --- | --- | --- |
| WO 99/42810 | Aug. 26, 1999 | US |
| WO 00/06193 | Oct. 2, 2000 | US |

OTHER REFERENCE DOCUMENTS

Roser, J F., Evans, J. W., Kiefer, D P., Neeley, D. P. and Pacheco, C. A. 1980. Reproductive efficiency in mares with anti-hCG antibodies. Proc $9^{th}$ Int. Congr. Artira. Repro. and A.I. 4: 627. abstr.
"Applying Semen Sexing Technology to the AI Industry", National Association of Animal Breeders, September 2000, pp. 1-16
"Sexed Semen Offers Faster Genetic Gain", Farming News, Livestock Supplement, February 1997, p. 28.
Akhtar, S., et al., "Prevalence of Five Stereotypes of Bluetongue Virus in a Rambouillet Sheep Flock in Pakistan", Veterinary ecord 136, 1995, p. 495.
Akhtar, S., et al., "Sex Preselected in Cattle: a Field Trial", Veterinary Record 136, 1995, p. 495-496.
Aldrich, S. L., Berger, L. L., Reiling, B. A., Kegler, D. I., and Nagh, T. G.. 1995. "Parturition and periparturient reproductive and metabolic hormone concentration in prenatally androgenized beefheifer", I. Anim. Sci. 73: 3712.
Amann, R. P. "Issues affecting commercialization of sexed sperm". Therio: 52: 1441, 1999
Amann, R. P. et al, "Prospects For Sexing Mammalian Sperm," Colorado Associated University Press, Animal Reproduction Laboratory College of Veterinary Medicine and Biomedical Sciences, Colorado State University, Fort Collins, CO, 80523, 1982
American Meat Science Association in cooperation with National Livestock and Meat Board. "Research guidelines for cookery, sensory evaluation and instrumental tenderness measurements of fresh meatK", 1995
Amoah, E. A. and Gelaye, S. 1996. Biotechnological advances in goat reproduction. J. Anim. Sci. 75(2): 578-585.
Andersen, V. K., Aamdal, J. and Fougner, J. A. 1973. Intrauterine und tiefzervikale Insemination mit Gefriersperma bein Schat. Zuchthygiene. 8: 113-118.
Bagley, C. P. 1993. Nutritional management of replacement beef heifers-A review. J. Anim. Sci. 71: 3155-3163.
Bailey, C. M., Reid, C. R., Ringkob, T. P., Koh, Y. O., and Foote, W. D. "Nulliparous versus primiparous crossbred females for beef." J. Anim. Sci. 69: 1403., 1991
Baker, R. D., Dziuk, P. J. and Norton, H. W. 1968. Effect of volume of semen, number of sperm and drugs on transport of sperm in artificially inseminated gilts. J. Anim. Sci. 27: 88-93.
Barnes, F. L. and Eyestone, W. H., "Early Cleavage and the Maternal Zygotic Transition in Bovine Embryos", Theriogeneology, Vol. 33, No. 1, January 1990, pp. 141-149
Becker, S. E. and Johnson, A. L. 1992. Effects of gonadotropin releasing hormone infused in a pulsatite or continuous fashion on serum gonadotropin concentrations and ovulation in the mare. J. Anim. Sci. 70: 1208-1215.
Bedford, S. J. and Hinrichs, K. 1994. The effect of insemination volume on pregnancy rates of pony mares. Theriogenology 42: 571-578.
Bellows, R. A., Short, R. E., Anderson, D. C., Knapp, B. W., and Pahnish, O. F. "Cause and effect relationships associated with calving difficulty and calfbirth weight", J. Anim. Sci. 33: 407, 1971
Berardinelli, J. G., R. A. Dailey, R. L. Butcher, and E. K. lnskeep. "Source of progesterolle prior to puberty in beef heifers". J. Anim. Sci. 49: 1276., 1979
Berger, G. S. 1987. Intratubal insemination. Fert. Steril. 48: 328-330.
Bergfeld, E. G., Kojima, F. N., Cupp, A. S., Wehnnan, M. E., Peters, K. T., Garciawinder, M., and Kinder, J. E., "Ovarian follicular development in prepubertal heifers is influenced by level of dietary energy-intake", Bio. of Repro. 51: 1051, 1994
Berry, B. W., Smith, G. C., and Carpente.zl, "Beef carcass maturity indicators and palatability attributes", J. Anim. Sci. 38: 507, 1974
Beyhan, Z., et al., "Sexual Dimorphism in IVF Bovine Embryos Produced by Sperm Sorted by High Speed Flow Cytometry", Theriogenology 49, 1998, p. 359.
Blanchard, T. and Dickson, V., "Stallion Management", The Veterinary Clinics of North America, Equine Practice, Vol. 8, No. 1, April 1992, pp 207-218.
Bond, J., et al., "Growth and carcass traits of open beef heifers versus beef heifers that have calved", Nutrition Reports International 34: 621. 1986
Boucque, C. V., et al., "Beef-production with maiden and once-calved heifers", Livestock Prod. Sci. 7: 121. 1980
Bourdon, R. M. and J. S. Brinks. "Simulated efficiency of range beef-production". Culling strategies and nontraditional management-systems. J. Anim. Sci. 65: 963. 1987
Bracher, V. and Allen, W. R., "Videoendoscopic Examination of the Mare's Uterus: Findings in Normal Fertile Mares", Equine Veterinary Journal, Vol. 24 (1992), pp. 274-278
Braselton, W. E. and McShan, W. H. 1970. "Purification and properties of follicle stimulating and luteinizing hormones from horse pituitary glands", Arch. Biochem. Biophys. 139: 45-48.
Brethour, J. R., "The single-calfheifer system", Kans. Agric. Sta. Rep. Frog. 570. 1989
Bristol, S. P. 1982. Breeding behavior of a stallion at pasture with 20 mares in synchronized oestrus. J. Reprod. Fert. Suppl. 32: 71.
Brookes, A. J. and Obyme, M., "Use of cow-heifers in beef production", J. of the Royal Agricultural Society of England 126: 30. 1965
Buchanan, B. R., et al, "Insemination of Mares with Low Numbers of Either Unsexed or Sexed Spermatozoa", Theriogenology, Vol. 53, pp 1333-1344, (2000)
Burns, P. D. and Spitzer, J. C., "Influence of biostimulation on reproduction in postpartum beef-cows", J. Anim. Sci. 70: 358. 1992
Burwash, L. D., Pickett, B. W., Voss, J. L. and Back, D. G. 1974. "Relationship of duration of estms to pregnancy rate in normally cycling, non-lactating mares" J.A.V.M.A. 165: 714-716.

-continued

Byerley, D. J., et al., "Pregnancy rates of beef heifers bred either on puberal or 3rd estrus". J Anim. Sci. 65: 645. 1987

Caslick, E. A., "The Vulva and the Vulvo-vaginal Orifice and its Relation to Genital Health of the Thoroughbred Mare", Cornell Veterinarian, Vol. 27, 1937, pp. 178-187

Catt, et al., "Assessment of Ram and Boar Spermatozoa During Cell-Sorting by Flow Cytometry", Reproduction Dom Animal, Vol. 32, 1997, pp 251-258.

Catt, S. L., et al., "Birth of a Male Lamb Derived from an In Vitro Matured Oocyte Fertilized by Intracytoplasmic Injection of a Single Presumptive Male Sperm", Veterinary Record 139, 1996, pp. 494-495.

Chin, W. W. and Boime, I. 1990. In: Glycoprotein Hormones. Serona Symp. Norwell, MA. pp. 19-20

Chung, Y. G., Schenk, J. L., Herickhoff, L. A. and Seidel, G. E. Jr. 1998. Artificial insemination of superovulated heifers with 600,000 sexed sperm. J Anim. Sci. Suppl. 1. 836: 215. abstr.

Clement, F., Vincent, P., Mahla, R., Meriaux, J. C. and Palmer, E. 1998. Which insemination fertilizes when several successive inseminations are performed before ovulation. $7^{th}$ Int. Symp. Eq. Repro. 151. abstr.

Coleou, J., et al., "Essai de velage tres precoce de genisses en vue de la production de viande." Essai Vauz/Aure no. 50, programme USFGC-INAPG-ITFC. 1974

Cran, D. G., et al., "Production of Bovine Calves Following Separation of X- and Y-Chromosome Bearing Sperm and In Vitro Fertilisation", Veterinary Record 132, 1993, pp. 40-41.

Cran, D. G., et al., "Production of Lambs by Low Dose Intrauterine Insemination with Flow Cytometrically Sorted and Unsorted Semen", Theriogenology 47, 1997, p. 267.

Crowley, J. P. The facts of once-bred heifer production. (Ed) J. B. Owens. The maiden female-a means of increasing meat production. School of Agric., Univ. of Aberdeen, Scotland. 1973

Curran, S. 1998. In: Equine Diagnostic Ultrasonography. Fetal gender determination. Rantanen & McKinnon. $1^{st}$ Ed. Williams and Wilkins. pp. 165-169.

Day, B. N., Abeydeera, L. R., Johnson, L. A., Welch, G. R., Wang, W. H., Cantley, T. C. and Rieke, A. 1998. Birth of piglets preselected for gender following in vitro fertilization of in vitro matured pig oocytes by X and Y bearing spermatozoa sorted by high speed flow cytometry. Theriogenology. 49(1): 360. abstr.

Dean, P. N., Pinkel, D. and Mendelsob. n, M. L. 1978. Hydrodynamic orientation of spermatozoa heads for flow cytometry. Biophys. J. 23: 7-13.

Demick, D. S., Voss, J. L. and Pickett, B. W. 1976. Effect of cooling, storage, glycerization and spermatozoal numbers on equine fertility. J. Anim. Sci. 43: 633-637.

DenDaas, J. H. G., De Jong, G., Lansbergen, L. M. T. E. and Van Wagtendonk-De Leeuw, A. M. 1998. The relationship between the number of spermatozoa inseminated and the reproductive efficiency of dairy bulls. J Dairy Sci. 81: 1714-1723.

Denham, A. "In-vitro studies on sandhill range forage as related to cattle preference", M.S. Thesis. 1965. Colorado State University.

Deutscher, G. H. "Extending interval from seventeen to nineteen days in the melengestrol acetate-prostaglandin estrous synchronization program for heifers". The Professional Animal Scientist 16: 164. 2000

"Diagnostic Products Corporation. Coat-A-Count", Progesterone.com. 1998.

Dikeman, M. E. "Cattle production systems to meet future consumer demands. J. Anim. Sci. 59: 1631, 1984

Dinnyes, A., et al., "Timing of the First Cleavage Post-insemination Affects Cryosurvival of In Vitro-produced Bovine Blastocysts", Molec Reprod Develop 53, 1999, pp 318-324.

Donaldson, L. E., "Effect of Insemination Regimen on Embryo Production in Superovulated Cows", The Veterinary Record, Jul. 13, 1985, pp. 35-37

Donoghue, A. M., Byers, A. P., Johnston, L. A., Armstrong, D. L. and Wildt, D. E. 1996. Timing of ovulation after gonadotropin induction and its importance to successful intrauterine insemination in the tiger (*Panthera tigris*). J. Reprod. Fert. 107: 53-58.

Douglas, R. H. 1979. Review of superovulation and embryo transfer in the equine. Theriogenology. 11: 33-46.

Douglas, R. H., Nuti, L. and Ginther, O. J. 1974. Induction of ovulation and multiple ovulation on seasonally-anovulatory mares with equine pituitary fractions. Theriogenology. 2(6): 133-142.

Doyle, S. P., et al. "Artificial insemination of lactating angus cows with sexed semen". Proc. Western Sect. Am.Soc.Anim. Sci. 50: 203. 1999

Duchamp, G., Bour, B., Combarnous, Y. and Palmer, E. 1987. Alternative solutions to hCG induction of ovulation in the mare. J. Reprod. Fert. Suppl. 35: 221-228.

Evans, M. J. and Irvine, C. H. G. 1977. Induction of follicular development, maturation and ovulation by gonadotropin releasing hormone administration to acyclic mares. Bio. Reprod. 16: 452-462.

Ferrell, C. L. and T. G. Jenkins. "Energy-Utilization by Mature, nonpregnant, nonlactating cows of different types" J. Anim. Sci. 58: 234. 1984

Ferrell, C. L. "Effects of post-weaning rate of gain on onset of puberty and productive performance of heifers of different breeds. J. Anim. Sci. 55: 1272. 1982

Field, R. A., et al., "Bone-ossification and carcass characteristics of wethers given silastic implants containing estradiol". I. Anim. Sci. 68: 3663-3668. 1990

Field, R., R. et al., "Growth, carcass, and tenderness characteristics of virgin, spayed, and single-calfheifers.", J. Anim. Sci. 74: 2178. 1996

Fitzgerald, B. P., Peterson, K. D. and Silvia, P. J. 1993. Effect of constant administration of a gonadotropin-releasing hormone agonist on reproductive activity in mares: Preliminary evidence on suppression of ovulation during the breeding season. Am. J. Vet. Res. 54: 1746-1751.

Fluharty, F. L., et al., "Effect of weaning and diet on growth of calves." Research and Reviews. The Ohio State University Department of Animal Sciences. 1996

Fluharty, F. L., et al., "Effects of Age at Weaning and Diet on Growth of Calves", Ohio Agri. Res. and Dev. Circular, 1996, 156: 29.

Foulkes, J. A., Stewart, D. L. and Herbert, C. N. 1977. Artificial insemination of cattle using varying numbers of spermatozoa. Vet. Rec. 101: 205.

Fugger, E. F., "Clinical Experience with Flow Cytometric Separation of Human X- and Y-Chromosome Bearing Sperm", Theriogenology, Vol. 52, pp. 1435-1440 (1999)

Fulwyler, M. J. 1965. Electronic separation of biological cells by volume. Science. 150: 910.

Fulwyler, M. J. 1977. Hydrodynamic orientation of cells. J Histochem. Cytochem. 25: 781-783.

Seidel, G. E.. Jr., "Artificial Insemination With X-and Y-Bearing Bovine Sperm", Animal Reproduction and Biotechnology Laboratory, Colorado State University, Fort Collins, CO; Germplasm and Gamete Physiology Lab, ARS, USDA, Beltsville, MD; Atlantic Breeders Coop, Lancaster, PA; DUO Diary, Loveland, CO, USA -continued January 1996.
Garner, D. L., Gledhill, B. L., Pinkel, D., Lake, S., Stephenson, D., Van Dilla, M. A. and Johnson, L. A. 1983. "Quantification of the X and Y chromosome-bearing spermatozoa of domestic animals by flow cytometry". Biol. Reprod. 28: 312-321.
Ginther, O. J. 1983. Sexual behavior following introduction of a stallion into a group of mares. Theriogenology. 19: 877.
Ginther, O. J. 1992. In: Reproductive Biology of the Mare. ($2^{nd}$ Ed.) Equiservices, Cross Plains, WI.
Gledhill, B. L. 1988. Gender preselection: historical, technical and ethical perspective. Semin Reprod. Endocrinol. 6: 385-395.
Gombe, S. and Hansel, W. "Plasma luteinizing-hormone (LH) and progesterone levels in heifers on restricted energy intakes." J. Anim. Sci. 37: 728. 1973
Gourley, D. D. and Riese, R. L. 1990. Laparoscopic artificial insemination in sheep. Vet. Clin. N. Amer: Food Anim. Prac. 6(3): 615-633.
Gravert, H. O., "Genetic Aspects of Early Calving." In: J. C. Taylor (Ed.) The early calving of heifers and it's impact on beef production. 59. 1975
Gregory, K. E., et al., "Characterization of biological types of cattle III .2." Growth-rate and puberty in females. J. Anim. Sci. 49: 461. 1979
Grimes, I. F, and T. B. Turner. "Early weaning of fall born calves II." Post weaning performance of early and normal-weaned calves. I. Prod. Agric. 4: 168. 1991
Grondahl, C., et al, "In Vitro Production of Equine Embryos", Biology of Reproduction, Monograph Series I, pp. 299-307 (1995)
Guillou, F. and Combarnous, Y. 1983. Purification of equine gonadotropins and comparative study of their acid-dissociation and receptor-binding specificity. Biochem. Biophys. Acta. 755: 229-236.
Gurnsey, M. P., and Johnson, L. A., "Recent improvements in efficiency of flow cytometric sorting of X and Y-chromosome bering sperm of domestic animals: a review", 1998, New Zealand Society of Animal Protection, three pages.
Hall, J. B., et al., "Effect of age and pattern of gain on induction of puberty with a progestin in beef heifers." J. Anim. Sci. 75: 1606. 1997
Hamano, K., et al., "Gender Preselection in Cattle with Intracytoplasmically Injected, Flow Cytometrically Sorted Sperm Heads", biology of Reproduction 60, 1999, pp. 1194-1197.
Harrison, L. A., Squires, E. L. and McKinnon, A. O. 1991. Comparison of hCG, buserelin and luprostiol for induction of ovulation in cycling mares. Eq. Vet. Sci. 3: 163-166.
Harte, F. J. "System of production of bee from once calved heifers." In: J. C. Taylor (Ed.) The early calving of heifers and it's impact on beef production. 123. 1975
Hawk, H. W., et al., "Fertilization Rates in Superovulating Cows After Deposition of Semen on the Infundibulum Near the Uterotubal Junction or After Insemination with High Numbers of Sperm", XP-002103478, Theriogenology, May 1988, Vol. 29, No. 5, pp 1131-1142.
Hemlesmeyer, G. N., et al. "Effects of lactation and prenatal androgenization on the perfomlance, carcass coompostion and longissimus muscle sensory characteristics of heifers in the single-calfheifer system." The Professional Animal Scientist 15: 14. 1999
Hennegmeyer, G. N., et al. "Effects of prenatal androgenization and implantation on the performance and carcass composition of lactating heifers in the single-calfheifer system." The Professional Animal Scientist 15: 173. 1999
Hilton, G. G., et al., "An evaluation of current and alternative systems for quality grading carcasses of mature slaughter cows." I. Anim. Sci. 76: 2094. 1998
Ho, L., et al., "Influence of gender, breed and age on maturity characteristics of sheep." J. Anim. Sci. 67: 2460-2470. 1989
Hofferer, S., Lecompte, F., Magallon, T., Palmer, E. and Combarnous, Y. 1993. Induction of ovulation and superovulation in mares using equine LH and FSH separated by hydrophobic interaction chromatography. J. Reprod. Fert. 98: 597-602.
Hohenboken, W. D. "Applications of sexed semen in cattle production." Therio.52: 1421. 1999
Holtan, D. W., Douglas, R. H. and Ginther, O. J. 1977. Estrus, ovulation and conception following synchronization with progesterone, prostaglandin F2 ct and human chorionic gonadotropin in pony mares. J. Anim. Sci. 44: 431-437.
Householder, D. D., Pickett, B. W., Voss, J. L. and Olar, T. T. 1981. Effect of extender, number of spermatozoa and hCG on equine fertility. J. Equine Vet. Sci. 1: 9-13.
Howard, J. G., Bush, M., Morton, C., Morton, F., Wentzel, K. and Wildt, D. E. 1991. Comparative semen cryopreservation in ferrets (*Mustela putorious furo*) and pregnancies after laparoscopic intrauterine insemination with frozen-thawed spermatozoa. J. Reprod. Fert. 92: 109-118.
Howard, J. G., Roth, T. L., Byers, A. P., Swanson, W. F. and Wildt, D. E. 1997. Sensivity to exogenous gonadotropins for ovulation and laparoscopic artificial insemination in the theetab and clouded leopard. Biol. Reprod. 56: 1059-1068.
Hunter, R. H. F. 1980. Transport and storage of spermatozoa in the female reproductive tract. Proc $4^{th}$ Int. Congr. Artira. Repro. and A.I. 9: 227-233.
Hyland, J. H., Ainsworth, C. G. V. and Langsford, D. A. 1988. Gonadotropin-releasing hormone (GnRH) delivered by continuous infusion induces fertile estrus in mares during seasonal acyclicity. Proc. Amer. Assoc. Eq. Prac. 181-190.
Irvine, C. H. G. and Alexander, S. L. 1993. In: Equine Reproduction. Edited by McKirmon and Voss. Lea and Febiger. Philadelphia, London. pp. 37.
Jafar, et al., "Sex Selection in Mammals: A Review", Theriogenology, vol. 46, 1996, pp 191-200.
Jarriage, R. "Age of cows at first calving in France." J. C. Taylor (Ed.) The early calving of heifers and it's impact on beef production. 10. 1975
Jasko, D. J., Martin, J. M. and Squires, E. L. 1992. Effect of volume and concentration of spermatozoa on embryo recovery in mares. Theriogenology. 37: 1233-1239
Johnson L. A., et al., 1987. Flow cytometry of X- and Y-chromosome bearing sperm for DNA using an improved preparation method and staining with Hoechst 333-42. Garnete Research 17: 203-212
Johnson, "Gender preselection in Mammals: An overview", Dtsch. Tierarztl. Wschr, Vol. 103, August/September 1996, pp 288-291.
Johnson, A. L. 1986. Pulsatile release of gonadotropin releasing hormone advances ovulation in cycling mares. Biol. Reprod. 35: 1123E 1130.
Johnson, A. L. and Becker, S. E. 1988. Use of gonadotropin-releasing hormone (GnRH) treatment to induce multiple ovulations in the anestrous mare. Eq. Vet. Sci. 8: 130-134.

-continued

Johnson, L., "Sex Preselection by Flow Cytometric Separation of X and Y Chromosome-Bearing Sperm Based on DNA Difference: a Review", Reproduction and Fertilization Development 7, 1995, pp. 893-903.

Johnson, L., "Successful Gender Preselection in Farm Animals", Agricultural Biotechnology, 1998, pp. 439-452.

Johnson, L. A. 1988. Flow cytometric determination of spermatozoa sex ratio in semen purportedly enriched for X or Y bearing spermatozoa. Theriogenology. 29: 265. abstr.

Johnson, L. A. 1992. Gender preselection in domestic animals using flow cytometrically sorted sperm. J Anim. Sci. Suppl 1.70: 8-18.

Johnson, L. A. 1994. Isolation of X- and Y-bearing spermatozoa for sex preselection. In: Oxford Reviews of Reproductive Biology. Ed. H H Charlton. Oxford University Press. 303-326.

Johnson, L. A. 1995. Sex preselection by flow cytometric separation of X and Y chromosome bearing spermatozoa based on DNA difference: a review. Reprod. Fert. Dev. 7: 893-903.

Johnson, L. A. and Schulman, J. D. 1994. The safety of sperm selection by flow cytometry. Ham. Reprod. 9(5): 758.

Johnson, L. A., "Sex preselection in swine: altered sex ratios in offspring following surgical insemination of flow-sorted X- and Y-bearing sperm", Reprod. Domest. Anim. 26: 309-314, 1991

Johnson, L. A., and Pinkel, D., "Modification of a Laser-Based flow Cytometer for High-Resolution DNA Analysis of Mammalian Spermatozoa", Cytometry 7, 1986, pp 268-273.

Johnson, L. A., et al., "Sex Preselection in Rabbits: Live Births from X and Y Sperm Separated by DNA and Cell Sorting", Exceptional Paper-Rapid Publication, XP-002103476, Biology of Reproduction 41, 199-203, 1989, pp 199-203.

Johnson, L. A., et al., 1994. Improved flow sorting resolution of X- and Y-chromosome bering viable sperm separation using dual staining and dead cell gating. Cytometry 17 (suppl 7): 83.

Johnson, L. A., Flook, J. P., Look, M. V. and Pinkel, D. 1987b. Flow sorting of X and Y chromosome bearing spermatozoa into two populations. Gam. Res. 16: 203-212.

Johnson, L. A., Welch, G. R., Rens, W. and Dobrinsky, J. R. 1998. Enhanced flow cytometric sorting of manunalian X and Ysperm: high speed sorting and orienting no77.1e for artificial insemination. Theriogenology. 49(1): 361. abstr.

Joseph, R. L. "Carcass composition and meat quality in once calved heifers." In: J. C. Taylor (Ed.) The early calving of heifers and it's impact on beef production. 143. 1975

Joseph, R. L. and J. P. Crowley. "Meat quality of once-calved heifers." Irish J. of Agric. Research 10: 281. 1971

Kachel, V., et al., A Uniform Lateral Orientation, Cused by Flow Forces, of Flat Particles in Flow-Through Systems@, The Journal of Histochemistry and Cytochemistry, 1997, Vol. 25, No. 7, pp 774-780.

Kanayama, K., Sankai, T., Nariaik, K., Endo, T. and Sakuma, Y. 1992b. Pregnancy by means of tubal insemination and subsequent spontaneous pregnancy in rabbits. J. Int. Med. Res. 20: 401-405.

Karabinus, et al., "Effects of Egg Yolk-Citrate and Milk Extenders on Chromatin Structured Viability of Cryopreserved Bull Sperm", Journal of Dairy Science, Vol. 74, No. 11, 1999, pp 3836-3848.

Keeling, P. C. B. M. S. T. G. D. I. a. P. W. J., "A modeling study of once-bred heifer beef production." Proceedings of the New Zealand Society of Animal Production. 51. 1991

Kilicarslan, M. R., Horoz, H., Senunver, S. C., Konuk, S. C., Tek, C. and Carioglu, B. 1996. Effect of GrnRH and hCG on ovulation and pregnancy in mares. Vet. Rec. 139: 119-120.

Kinder, J. E., et al. "Endocrine basis for puberty in heifers and ewes." J. Repro. and Fertility 393. 1995

Klindt, J. and J. D. Crouse. "Effect of ovariectomy and ovariectomy with ovarian auto transplantation on feedlot performance and carcass characteristics of heifers." J. Anim. Sci. 68: 3481. 1990

Klosterman, E. W. and C. F. Parker. "Effect of size, beed and sex upon feed efficiency in beef cattle." North Central Regional Research Publication 235, Ohio Agric. Research and Development Center 1090: 3. 1976

Kniffen, D. M., Wagner, W. R., and Lewis. P. E. "Effects oflong-tenn estrogen implants in beef heifers." I. Anim. Sci. 77: 2886. 1999

Koch, R. M., et al., "Characterization of biological types of cattle-Cycle-II .3." Carcass composition, quality and palatability. I. Anim. Sci. 49: 448. 1919

Lapin, D. R. and Ginther, O. J. 1977. Induction of ovulation and multiple ovulations in seasonally anovulatory and ovulatory mares with an equine pituitary extract. J. Anim. Sci. 44: 834-842.

Laster, D. B., "Factors affecting dystocia and effects of dystocia on subsequent reproduction in beef-cattle." J. Anim. Sci. 36: 695. 1973

Lawrenz, R. 1985. Preliminary results of non-surgical intrauterine insemination of sheep with thawed frozen semen. J S Afr. Vet. Assoc. 56(2): 61-63.

Levinson, G., et al, 1995. DNA-based X-enriched sperm separation as an adjunct to preimplantation genetic testing for the preparation of X-linked disease. Mol. Human Reprod. 10: 979-982.

Lindsey, A., et al., A Hysteroscopic Insemination of Mares with Nonfrozen Low-dose Unsexed or Sex-sorted Spermatozoa@, currently unpublished, pp. 1-15.

Linge, F. 1972. Faltforsok med djupfrost sperma (field trials with frozen sperm). Farskotsel. 52: 12-13.

Lonergan, P., et al., "Effect of Time Interval from Insemination to First Cleavage on the Development of Bovine Embryos In Vitro and In Vivo", Theriogenology, 1999, p. 326

Long, C. R., Rath, D., Welch, G. R., Schreier, L. L., Dobrinsky, J. R. and Johnson, L. A. 1998. AIn vitro production of porcine embryos from semen sorted for sex with a high speed cell sorter: comparison of two fertilization media.@, Theriogenology. 49(1): 363. abstr.

Loy, R. G. and Hughes, J. P. 1965. The effects of human chorionic gonadotropin on ovulation, length of estrus, and fertility in the mare. Cornell Vet. 56: 41-50.

Lu, K. H., et al., "In Vitro Fertilization with Flow-Cytometrically-Sorted Bovine Sperm", Theriogenology 52, 1999, pp. 1393-1405.

Lynch, I. M., et al., "Influence of timing of gain on growth and reproductive performance ofbeefreplacement heifers." I. Anim. Sci. 75: 1715. 1997

Macmillan, K. L. and A. M. Day, "Prostaglandin F2a - A Fertility Drug In Dairy Cattle?",, Ruakura Animal Research Station, Private Bag, Hamilton, New Zealand, Theriogenology, September 1982, Vol. 18 No. 3, pages 245-253

Martin, A. H., et al., "Characteristics of youthful beef carcasses in relation to weight, age and sex .3. meat quality attributes." Canadian I. Anim. Sci. 51: 305. 1971

Martin, L. C., J. S. Brinks, R. M. Bourdon, and L. V. Cundiff. "Genetic-effects on beef heifer puberty and subsequent reproduction." J. Anim. Sci. 70: 4006. 1992

Matsuda, Y. and Tobari, I. 1988. Chromosomal analysis in mouse eggs fertilized in vitro with sperm exposed to ultraviolet light (UV) and methyl and ethyl methanesulfonate (MMS and EMS). Mutat. Res. 198: 131-144.

-continued

Matulis, R. J., F. K. Mckeith, D. B. Faulkner, L. L. Berger, and P. George. "Growth and carcass characteristics of cull cows after different times-on-feed." J. Anim. Sci. 65: 669. 1987
Mauleon, P. "Recent research related to the physiology of puberty." Commission of the European Communities. The early calving of heifers and it's impact on beef production. 1975
Maxwell, W. and Johnson, L., "Chlortetracycline Analysis of Boar Spermatozoa after Incubation, Flow Cytometric Sorting, Cooling, or Cryopreservation", Molecular Reproduction and Development 46, 1997, pp. 408-418.
Maxwell, W. M. C., Evans, G., Rhodes, S. L., Hillard, M. A. and Bindon, B. M. 1993. Fertility of Superovulated Ewes after Intrauterine or Oviductal Insemination with Low Numbers of Fresh or Frozen-Thawed Spermatozoa. Reprod. Fertil. Dev. 5: 57-63.
Mccomlick, R. J. "The flexibility of the collagen compartment of muscle." Meat Sci. 36: 79. 1994
McCue, P. M. 1996. Superovulation. Vet. Clin. N. Amer. Eq. Prac. 12: 1-11.
McCue, P. M., Fleury, J. J., Denniston, D. J., Graham, J. K. and Squires, E. L. 1997. Oviductal insemination in the mare. $7^{th}$ Int Symp. Eq. Reprod. 133. abstr.
McDonald, L. E. 1988. Hormones of the pituitary gland. In: Veterinary Pharmacology and Therapeutics. $6^{th}$ ed. Edited by N. H. Booth and L. E. McDonald. Ames, Iowa State Univ. Press. pp. 590.
McKenna, T., Lenz, R. W., Fenton, S. E. and Ax, R. L. 1990. Nonreturn rates of dairy cattle following uterine body or cornual insemination. J. Dairy Sci. 73: 1179-1783.
McKinnin, A. and Voss, J., "Equine Reproduction", Lea & Febiger, Philadelphia, 1993, pp 291, 299-302, 345-348, 739-797.
McKinnon, A. et al, 1993. Predictable ovulation in mares treated with an implant of the GnRH analogue deslorelin. Eq. Vet. J. 25: 321-323.
McKinnon, A. O. et al, 1996. Repeated use of a GnRH analogue deslorelin (Ovuplant) for hastening ovulation in the transitional mare. Eq. Vet. J. 29: 153-155.
McNutt, et al., "Flow Cytometric Sorting of Sperm: Influence on Fertilization and Embryo/Fetal Development in the Rabbits", Molecular Reproduction and Development, Vol. 43, 1996, pp 261-267.
Meilgaard, M., G. V. Civille, and B. T. Carr. "Sensor Evaluation Techniques." CRC Press Inc., Boca Raton, FL. 1991
Meinert, C., et al., "Advancing the time of ovulation in the mare with a short-term implant releasing the GnRH analogue deslorelin", Equine Veterinary Journal, 25, 1993, pp 65-68.
Merton, J., et al., "Effect of Flow Cytometrically Sorted Frozen/Thawed Semen on Success Rate of In Vitro Bovine Embryo Production", Theriogenology 47, 1997, pp. 295.
Meyers, P. J., Bowman, T., Blodgett, G., Conboy, H. S., Gimenez, T., Reid, M. P., Taylor, B. C., Thayer, J., Jochle, W. and Trigg, T. E. 1997. Use of the GnRH analogue, deslorelin acetate, in a slow release implant to accelerate ovulation in oestrous mares. Vet. Rec. 140: 249-252.
Michaels, Charles, "Beef A.I. Facilities that work", Proc. Fifth N.A.A.B Tech. Conf. A.I. Reprod. Columbia, MO. pp. 20-22.
Michel, T. H., Rossdale, P. D. and Cash, R. S. G. 1986. Efficacy of human chorionic gonadotrophin and gonadatrophin releasing hormone for hastening ovulation in Thoroughbred mares. Eq. Vet. J. 6: 438-442.
Miller, S. J. 1986. Artificial Breeding Techniques in Sheep. In Morrow, D. A. (ed): Current Therapy in Theriogenology 2. Philadelphia, W B Saunders.
Mirskaja, L. M. and Petrapavlovskii, V. V. 1937. The reproduction of normal duration of heat in the mare by the administration of Prolan. Probl. Zivotn. Anim. Breed. Abstr. 5: 387.
Moe, P. W., H. F. Tyrrell, and W. P. Flatt. "Energetics of bodytissue mobilization." J. of Dairy Sci. 54: 548.
Molinia, F. C., Gibson, R. J., Brown, A. M., Glazier, A. M. and Rodger, J. C. 1998. Successful fertilization after superovulation and laparoscopic intrauterine insemination of the brushtail possum, *Trichosurus vulpecula*, and tammar wallaby, *Macropus eugenii*. J. Reprod. Fert. 112: 9-17.
Moms, S. T., et al., "Biological efficiency: How relevent is this concept to beef cows in a mixed livestock seasonal pasture supply context?" Proceedings of the New Zealand Society of Animal Production 54: 333. 1994
Monensin." J. Anim. Sci. 55: 357-362. 1982
Moran, C., J. F. Quirke, and J. F. Roche. "Puberty in heifers-a review." Animal Reproduction Sci. 18: 167. 1989
Morcom, C. B. and Dukelow, W. R. 1980. A research technique for the oviductal insemination of pigs using laparoscopy. Lab. Anim. Sci. 1030-I031.
Morgan, J. B., et al., "National beef tenderness survey." J. Anim. Sci. 69: 3274. 1991
Morris, L. H., et al., "Hysteroscopic insemination of small numbers of spermatozoa at the uterotubal junction of preovulatory mares", Journal of Reproduction and Fertility, Vol. 118, pp. 95-100 (2000)
Moseley, W. M., et al., 1982. "Relationship of Growth and Puberty in Beef Heifers Fed
Mount, D. E. "Fibrous and non-fibrous carbohydrate supplementation to ruminants grazing forage from small grain crops." M.S. Thesis. Colorado State University. 2000
Muller, W. and Gautier, F. 1975. Interactions of heteroaromatic compounds with nucleic acids. Euro. J Biochem. 54: 358.
Munne, S. 1994. Flow cytometry separation of X and Y spermatozoa could be detrimental to human embryos. Hum. Reprod. 9(5): 758
Myers, S. E., "Performance and carcass traits of early-weaned steers receiving either a pasture growing period or a finishing diet at weaning." J. Anim. Sci. 77: 311. 1999
Myers, S. E., et al., "Comparison of three weaning ages on cow-calf performance and steer carcass traits." J. Anim. Sci. 77: 323. 1999
Myers, S. E., et al., "Production systems comparing early weaning to normal weaning with or without creep feeding for beef steers." J. Anim. Sci. 77: 300. 1999
Nix, I. P., I. C. Spitzer, and P. I. Chenoweth. "Serum testosterone concentration, efficiency of estrus detection and libido expression in androgenized beef cows." Therio. 49: 1195. 1998
Nowshari, et al., "Superovulation of Goats with Purified pFSH Supplemented with Defined Amounts of pLH", Theriogenology, Vol 43, 1995, pp 797-802.
Nowshari, et al., Theriogenology, Vol 43, 1995, pp 797-802.
NRC. Nutrient requirements for beef cattle. National Academy of Sci. National Research Council, Washington, DC. 1996
Olson, S. E. and Seidel, G. E. Jr., "Reduced Oxygen Tension and EDTA improve Bovine Zygote Development in a Chemically Defined Medium", Journal of Animal Science 78, 2000, pp. 152-157.
Owen, J. B. "The maiden female-a means of increasing meat production." Proc. Symp. on the use of once bred heifers and gilts. 1973
Pace, M. M. and Sullivan, J. J. 1975. Effect of timing of insemination, numbers of spermatozoa and extender -continued components on pregnancy rates in mares inseminated with frozen stallion semen. J Reprod. Fert. Suppl. 23: 115-121.
Parent U.S. application Ser. No. 09/001,394, entitled "Sheath Fluids and Collection Systems for Sex-Specific Cytometer Sorting of Sperm", filed on Dec. 31, 1997, 87 total pages which includes four drawings.
Parrish, J., et al., "Capacitation of Bovine Sperm by Heparin", Technology of Reproduction 38, 1988, pp. 1171-1180.
PCT application, PCT/US99/17165, filed 28 Jul. 1999, entitled "Equine System for Non-Surgical Artificial Insemination".
PCT application, PCT/US98/27909, filed 31 Dec. 1998, entitled "Commercially Practical Sex-Specific Insemination of Mammals".
Peippo, J., et al., "Sex diagnosis of equine preimplantation embryos using the polymerase chain reaction", Theriogenology, Vol. 44 619-627 (1995)
Perry, E. J. 1968. Historical Background In: The Artificial Insemination of Farm Animals. 4$^{th}$ ed. Edited by E. J. Perry. New Brunswick, Rutgers University Press, pp. 3-12.
Petersen, G. A., et al, "Cow and Calf Performance and Economic Considerations of Early Weaning of Fall-Born Beef Calves", J. Anim. Sci., 1987, 64: 15, pp 15-22.
Petit, M. "Early Calving in Suckling Herds." In: (Ed.) J. C. Taylor. The early calving of heifers and it's impact on beef production. 157. 1975
Pickett G W, et al., "Management of the mare for maximum reproductive efficiency", Bulletin No. 6 Colorado State University, Ft. Collins CO. (1989)
Pickett, B. W, et al., 1976. Factors influencing the fertility of stallion spermatozoa in an A.I. program. Proc. 8$^{th}$ Internat. Congr. Anim. Reprod. A.I. Krakow, Poland. 4: 1049-1052.
Pickett, B. W. and Back, D. G. 1973. Procedures for preparation, collection, evaluation and insemination of stallion semen. C.S.U. Exp. Sta. Artira. Reprod. Lab. Gen. Series Bull. 935.
Pickett, B. W., and Shiner, K. A., "Recent developments in artificial insemination in horses", Livestock Production Science, 40, 1994, pp 31-36.
Pickett, B. W., Burwash, L. D., Voss, J. L. and Back, D. G. 1975b. Effect of seminal extenders on equine fertility. J. Anim. Sci. 40: 1136-1143.
Pinkel, D., et al, "Flow Cytometric Determination of the Proportions of X- and Y-Chromosome-Bearing Sperm in Samples of Purportedly Separated Bull Sperm", Journal of Animal Science, Vol. 60, No. 5, 1985, pp 1303-1307.
Pinkel, D., Gledhill, B. L., Van Dilla, M. A., Stephenson, D. and Watchmaker, G. 1982b. High resolution DNA measurements of mammalian spermatozoa. Cytometry. 3: 1-9. (1982b)
Polge, E. J., "Historical Perspective of AI: Commercial Methods of Producing Sex Specific Semen, IVF Procedures", Proceedings of the 16$^{th}$ Technical Conference on Artificial Insemination & Reproduction, Cambridge, England, 1996, pp. 7-11.
Purvis, H. T. and J. C. Whittier. "Effects of ionophore feeding and anthelmintic administration on age and weight at puberty in spring-born beef heifers." J. Anim. Sci. 74: 736-744. 1996
Randel, R. D. "Nutrition and postpartum rebreeding in cattle." J. Anim. Sci. 68: 853. 1990
Rath, D., et al., "Low Dose Insemination Technique in the Pig", Boar Semen Preservation IV, 2000, pp. 115-118.
Rath, D., et al., "Production of Piglets Preselected for Sex Following in Vitro Fertilization with X and Y Chromosome-Bearing Spermatozoa Sorted by Flow Cytometry", Theriogenology, 47, 1997, pp 795-800.
Reiling, B. A., et al., "Effect of Prenatal Androgenization on Performance, Location, and Carcass and Sensory Traits on Heifers in Single Calf Heifer System", J. Anim. Sci., 1995, 73: 986, pp 986-992.
Rens, W., et al, "A Novel Nozzle for More Efficient Sperm Orientation to Improve Sorting Efficiency of X and Y Chromosome-Bearing Sperm", Cytometry 33, 1998, pp. 476-481
Rens, W., et al., "Improved Flow Cytometric Sorting of X- and Y-Chromosome Bearing Sperm: Substantial Increase in Yield of Sexed Semen", Molecular Reproduction and Development, 1999, pp 50-56.
Rieger, D., et al, "The Relationship Between the Time of First Cleavage of Fertilized Cattle Oocytes and Their Development to the Blastocyst Stage", Theriogenology, 1999, pp. 190.
Ritar, A. and Ball, A. 1991. Fertility of young cashmere goats after laparoscopic insemination. J. Agr. Sci. 117: 271-273.
Roberts, J. R. 1971. In: Veterinary Obstetrics and Genital Diseases. Ithaca, New York. pp. 740-749.
Romita, A. "Some considerations on the beef situation in Italy." (Ed.) J. C. Taylor. The early calving of heifers and it's impact on beef production. 23. 1975
Roth, T. L., Wolfe, B. A., Long, J. A., Howard, J. and Wildt, D. E. 1997. Effects of equine chorionic gonadotropin, human chorionic gonadotropin, and laparoscopic artificial insemination on embryo, endocrine, and luteal characteristics in the domestic cat. Bio Reprod. 57: 165-171.
Roux, M., J. H. Teissier, J. Bonnemaire, and R. Dumont. "Early calving heifers versus maiden heifers for beef-production from dairy herds. 1." The effects of genotype (Friesian and Charolais × Friesian) and 2 feeding levels in the rearing period on growth and carcass quality. Livestock Prod. Sci. 16: 1. 1987
Rowley, H-S., Squires, E. L. and Pickett, B. W. 1990. Effect of insemination volume on embryo recover}' in mares. J. Equine Vet. Sci. 10: 298-300.
Roy, J. H. B. "Rearing dairy-herd replacements." J. of the Soc. of Dairy Technology 31: 73-79. 1978
Rutter, L. M., et al., "Effect of abomasal infusion of propionate on the GnRH-induced luteinizing-hormone release in prepuberal heifers." J. Anim. Sci. 56: 1167. 1983
Salamon, S. 1976. Artificial Insemination of Sheep. Chippendale, New South Whales. Publicity Press. p. 83-84.
Salisbury, G. W. and VanDemark, N. L. 1961. Physiology of Reproduction and Artificial Insemination of Cattle. San Francisco: Freeman and Company.
SAS, SAS/STAT, "Useres Guide (Release 6.03)", SAS Inst. Inc., Cary, NC., 1988. 3 pages
SAS. "The SAS System for Windows." Ver 7.0. Rel 6.12. SAS Inst.Inc., Cary, NC. 2000
Schenk, J. L., T. K. Suh, D. G. Cran, and G. E. Seidel. "Cryopreservation of flow-sorted bovine spennatozoa." Therio. 52: 1375. 1999
Schenk, J. L. and Seidel, Jr., G. E., "Imminent Commercialization of Sexed Bovine", Proceedings, The Range Beef Cow Symposium XVL, 1999, pp 89-96.
Schillo, K. K., J. B. Hall, and S. M. Hileman. "Effects of nutrition and season on the onset of puberty in the beef heifer." J. Anim. Sci. 70: 3994. 1992
Schmid R. L., et al, "Fertilization with Sexed Equine Spermatozoa Using Intracytoplasmic Sperm Injection and Oviductal Insemination", 7th International Symposium On Equine Reproduction, pp. 139 (Abstract) (1998)
Schnell, T. D., K. E. Belk, J. D. Tatum, R. K. Miller, and G. C. Smith. "Performance, carcass, and palatability traits for cull cows fed high-energy concentrate diets for 0, 14, 28, 42, or 56 days." J. Anim. Sci. 75: 1195. 1997
Schoonmkker, J. P., et al., "Effects of age at weaning and implant strategy on growth of steer calves." J. Anim.

-continued

Sci. (Suppl2) 76: 71 (Abstr.). 1998
Seidel, G. E. and L. A. Johnson. "Sexing mammalian spenn-overview." Therio. 52: 1267. 1999
Seidel, G. E., "Insemination of heifers with sexed sperm." Therio. 52: 1407. 1999
Seidel, G. E. Jr., "Uterine Horn Insemination of Heifers With Very Low Numbers of Nonfrozen and Sexed Spermatozoa", Atlantic Breeders Cooperative, Theriogenology 48: pp. 1255-1264, (1997)
Seidel, G. E. Jr., Cran, D. G., Herickoff L. A., Schenk, J. L., Doyle, S. P. and Green, R. D. 1999. Insemination of heifers with sexed frozen or sexed liquid semen. Theriogenology. 51. (in press). abstr.(1999)
Seidel, G. E., Jr., et al, "Artificial Insemination With X-and Y-Bearing Bovine Sperm", Animal Reproduction and Biotechnology Laboratory, Colorado State University, Fort Collins, CO; Germplasm and Gamete Physiology Lab, ARS, USDA, Beltsville, MD; Atlantic Breeders Coop, Lancaster, PA; DUO Diary, Loveland, CO, USA January 1996.
Seidel, G. E., Jr., et al, "Insemination Of Heifers With Very Low Numbers Of Frozen Spermatozoa.", Colorado State University, Fort Collins, Atlantic Breeders Cooperative, Lancaster, PA, DUO Dairy, Loveland, CO, July 1996.
Seidel, Jr., G. E., et al, "Insemination of Holstein Heifers With Very Low Numbers Of Unfrozen Spermatozoa", Colorado State University, Atlantic Breeders Cooperative, (1995)
Seidel, Jr., G. E. et al, "Insemination Of Heifers With Very Low Numbers Of Frozen Spermatozoa", Colorado State University (1996)
Sell, R. S., D. L. Watt, R. D. Little, and T. A. Petry. "Single-calfheifer profitability compared to other north dakota beef production systems." Department of Ag. Eco., North Dakota State University, Ag. Econ. Rpt. 20.
Senger, P. L., Becker, W. C., Davidge, S. T., Hillers, J. K. and Reeves, J. J. 1988. Influence of cornual insemination on conception rates in dairy cattle. J Anim. Sci. 66: 3010-3016.
Shackelford, S. D., M. Koohmaraie, and T. L. Wheeler. "Effects of slaughter age on meat tenderness and usda carcass maturity scores of beef females." I. Anim. Sci. 73: 3304. 1995
Shelton, J. N. and Moore, N. W. 1967. The response of the ewe tot pregnant mare gonadotropin and to horse anterior pituitary extract. J. Reprod. Fert. 14: 175-177.
Shilova, A. V., Platov, E. M. and Lebedev, S. G. 1976. The use of human chorionic gonadothrophin for ovulation date regulation in mares. VIIIth Int. Congr. On Anim. Repro. and A.I. 204-208.
Shorthose, W. R. and P. V. Harris. "Effect of animal age on the tenderness of selected beef muscles." I. Food Sci. 55: 1-. 1990
Silbennann, M., "Honnones and Cartilage. Cartilage: development, differentiation, and growth." pp. 327-368. Academic Press, Inc. 1983
Simon, M., "The effect of management option on the perfonnance of pregnant feedlot heifers." M.S. Thesis. Kansas State University. 1983
Smith, G. C., B. W. Berry, J. W. Savell, and H. R. Cross. "USDA maturity indexes and palatability of beefrib steaks." J. of Food Quality 11: 1. 1988
Smith, G. C., et al., "Relationship of usda maturity groups to palatability of cooked beef." J. of Food Sci. 47: 1100. 1982
Squires, E., "Simultaneous Analysis of Multiple Sperm Attributes by Flow Cytometry☐, Diagnostic Techniques and Assisted Reproductive Technology, The Veterinary Clinics of North America, Equine Practice, Vol. 12, No. 1, April 1996, pp 127-130.
Squires, E. L, Moran, D. M., Farlin, M E., Jasko, D. J., Keefe, T. J., Meyers, S. A., Figueiredo, E., McCue, P. M. and Jochle, W. 1994. Effect of dose of GnRH analogue on ovulation in mares. Theriogenology. 41: 757-769.
Squires, E. L., "Early Embryonic Loss in Equine Diagnostic Ultrasonography", $1^{st}$ Ed. pp 157-163 Eds Rantanen & McKinnon. Williams and Wilkins, Baltimore, Maryland (1998)
Squires, E. L.., et al, "Cooled and frozen stallion semen", Bulletin No. 9, Colorado State University, Ft. Collins, CO. (1999)
Stellflug, J. N., D. K. Ran, R. D. Randel, and Eo L. Moody. "Plasma estrogens in peri-parturient cow." Therio 10: 269. 1978
Stevenson, J. S., M. W. Smith, J. R. Jaeger, L. R. Corah, and D. G. Lefever. "Detection of estrus by visual observation and radiotelemetry in peripubertal, estrus-synchronized beefheifers." J. Anim. Sci. 74: 729. 1996
Story, C. E., R. J. Rasby, R. T. Clark, and C. T. Milton. "Age of calf at weaning of spring-calving beef cows and the effect on cow and calf perfomlance and production economics." J. Anim. Sci. 78: 1403. 2000
Sullivan, J. J., Parker, W. G. and Larson, L L. 1973. Duration of estrus and ovulation time in nonlactating mares given human chorionic gonadotropin during three successive estrous periods. J.A.V.M.A. 162: 895-898.
Swanson, E. W. "Future research on problems of increasing meat production by early calving." Comm. Eur. Commun., Eur. 5545. 1975. The Early Calving of Heifers and its Impact on Beef Production.
Taljaard, T. L., Terblanche, S. J., Bertschinger, H. J. and Van Vuuren, L. J. 1991. The effect of the laparoscopic insemination technique on the oestrus cycle of the ewe. J. S Afr. Vet. Assoc. 62(2): 60-61.
Tatum, J. D., G. C. Smith, B. W. Berry, C. E. Murphey, F. L. Williams, and Z. L. Carpenter. "Carcass characteristics, time on feed and cooked beef palatability attributes." J. Anim. Sci. 50: 833. 1980
Taylor, C. S., Moore, A. J. Thiessen, R. B. and Bailey, C. M., AFRC Animal Breeding Research Organisation, West Mains Road, Edinburg EH9 3JQ, "Efficiency of Food Utilization in Traditional and Sex-Controlled Systems of Beef Production", pp 401-440.
Taylor, S. C. S., A. J. Moore, R. B. Thiessen, and C. M. Bailey. "Efficiency of food utilization in traditional and sex-controlled systems of beef-production." Animal Production 40: 401. 1985
Tervit, H. R., et al., "Successful Culture In Vitro of Sheep and Cattle Ova", Agricultural Research Council, Unit of Reproduction Physiology and Biochemistry, University of Cambridge, 1972, p. 493-497.
Unruh, J. A. "Effects of endogenous and exogenous growth-promoting compounds on carcass composition, meat quality and meat nutritional-valu~." J. Anim. Sci. 62: 1441. 1986
U.S. application Ser. No. 09/454,488, entitled "Improved Flow Cytometer Nozzle and Flow Cytometer Sample Handling Methods", filed Dec. 3, 1999.
U.S. application Ser. No. 60/238,294, entitled "Hysteroscopic Insemination of Mares" filed Oct. 5, 2000.
U.S. application Ser. No. 09/448,643, entiled "Multiple Sexed Embryo Production System for Mammals", filed Nov. 24, 1999.
U.S. application Ser. No. 09/511,959 entitled "Methods For Improving Sheath Fluids and Collection Systems For Sex-Specific Cytometer Sorting of Sperm", filed Feb. 23, 2001.
U.S. application Ser. No. 09/001,394, entitled "Sheath Fluids and Collection Systems for Sex-Specific Cytometer Sorting of Sperm", filed on Dec. 31, 1997, 87 total pages which includes four drawings.

-continued

U.S. application Ser. No. 09/015,454, entitled "System for Improving Yield of Sexed Embryos in Mammals", filed on Jan. 29, 1998, 59 total pages which includes drawings.
U.S. application Ser. No. 60/211,093, entitled "Integrated System for Herd Management Using Sexed Semen", filed Jun. 12, 2000.
U.S. application Ser. No. entitled "System For Separating Frozen-Thawed Sperm Cells Into X-Chromosome And Y-Chromosome Bearing Populations", filed Nov. 28, 2000.
U.S. application Ser. No. 60/094,720, entitled "System for Low Dose Insemination of Equines", filed Jul. 30, 1998.
U.S. application Ser. No. 60/113,143, entitled "Equine Insemination System", Dec. 18, 1998.
U.S. application Ser. No. 60/203,089, entitled "Detector System for Resolving Small Differences in Photo-generated Signal", filed May 9, 2000.
U.S. application Ser. No. 60/211,093, entitled "Integrated System for Herd Management Using Sexed Semen", filed Jun. 12, 2000.
U.S. application Ser. No. 60/224,050., entitled "Integrated System for Herd Management With Terminal-Cross Program Using Sexed Semen", filed Aug. 9, 2000.
USDA "Official United States standards for grades of carcass beef." Agric, Marketing Serv., USDA. Washington, DC. 1997
Vazquez, J. et al., "Nonsurgical Uterotubal Insemination in the Mare", Proceedings of the 44th Annual Convention of the American Association of Equine Practitioners, Baltimore, Maryland, Dec. 6-9, 1998, Vol. 44, pp 68-69
Vazquez, J., et al., "A.I. in Swine; New Strategy for Deep Insemination with Low Number of Spermatozoa Using a Non-surgical Methodology", $14^{th}$ International Congress on Animal Reproduction, Vol. 2, Stockhlom, July, 2000, p. 289.
Vazquez, J., et al., "Development of a Non-surgical Deep Intra Uterine Insemination Technique", IV International Conference on Boar Semen Preservation, Maryland, August, 1999, p 35 and photo of display board.
Vazquez, J., et al., "Successful Low-Dose Insemination by a Fiberoptic Endoscope Technique in the Sow", Proceedings Annual Conference of the International Embryo Transfer Society, Netherlands, Theriogenology, Vol. 53, January, 2000, pp. 201.
Vazquez, J., et al., "Hypoosmotic Swelling Test as Predictor of the Membrane Integrity in Boar Spermatozoo", Boar Semen Preservation IV, IVth International Conference on Boar Semen Preservation, Maryland, pp. 263.
Vidament, M., Dupere, A. M., Julienne, P., Evain, A., Noue, P. and Palmer, E. 1997. Equine frozen semen freezeability and fertility field results. Theriogenology. 48: 907.
Vincent, B. C., S. D. M. Jones, L. E. Jeremiah, M. A. Price, and J. A. Newman. "Carcass characteristics and meat quality of once-calved heifers." Canadian J. Anim. Sci. 71: 311. 1991
Voss, J. L. and Pickett, B. W. 1976. Reproductive management of the broodmare. C.S.U. Exp. Sta. Anim. Reprod. Lab. Gen. Series. Bull. 1-12
Voss, J. L., Pickett, B. W., Burwash, L. D. and Daniels, W. H. 1974. Effect of human chorionic gonadotropin on duration of estrous cycle and fertility of normally cycling, nonlactating mares. J.A.V.M.A. 165: 704-706.
Voss, J. L., Squires, E. L., Pickett, B. W., Shideler, R. K. and Eikenberry, D. J. 1982. Effect of number and frequency of inseminations on fertility in mares. J. Reprod. Fertil. Suppl. 32: 53-57.
Waggoner, A. W., M. E. Dikeman, I. R. Brethour, and K. E. Kemp. "Performance, carcass, cartilage calcium, sensory and collagen traits of longissimus muscles of open versus 30-month-old heifers that produced one calf." I. Anim. Sci. 68: 2380. 1990
Welch G. R., et al., 1994. Fluidic and optical modifications to a FACS IV for flow sorting of X- and Y-chromosome bearing sperm based on DNA. Cytometry 17 (suppl. 7): 74.
Welch, G., et al., "Flow Cytometric Sperm Sorting and PCR to Confirm Separation of X- and Y-Chromosome Bearing Bovine Sperm☐, Animal Biotechnology, 6 (2), 131-139, 1995, pp 131-139.
Wheeler, T. L., L. v. Cundiff. and, R. M. Koch. "Effect of marbling degree on beef palatability in Bos-Taurus and Bos-Indicus cattle." J. Anim. Sci. 72: 3145. 1994
Wickersham, E. W. and L. H. Schultz. "Infilience of age at first breeding on growth, reproduction, and production of well-fed holstein heifers." J. Dairy Sci. 46: 544. 1963
Wilson, C. G., Downie, C. R., Hughes, J. P. and Roser, J. F. 1990. Effects of repeated hCG injections on reproductive efficiency in mares. Eq. Vet. Sci. 4: 301-308.
Wilson, M. S. 1993. Non-surgical intrauterine artificial insemination in bitches using frozen semen. J. Reprod. Fert Suppl. 47: 307-311.
Woods, J. and Ginther, O. J. 1983. Recent studies related to the collection of multiple embryos in mares. Theriogenology. 19: 101-108.
Woods, J., Bergfelt, D. R. and Ginther, O. J. 1990. Effects of time of insemination relative to ovulation on pregnancy rate and embryonic-loss rate in mares. Eq. Vet. J. 22(6): 410-415.
XP-002103478, File Biosis, one page.

In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. However, as to each of the above, to the extent that such information or statements incorporated by reference might be considered inconsistent with the patenting of this/these invention(s) such statements are expressly not to be considered as made by the applicant(s).

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like.

Thus, the applicant(s) should be understood to have support to claim at least: i) each of the staining, separation, isolation, insemination, or fertilization procedures as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, and x) the various combinations and permutations of each of the elements disclosed.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the subject matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A process for preparing sperm cell samples, the process comprising:
    collecting semen from a male mammal;
    freezing said semen to form frozen semen;
    thawing said frozen semen to form frozen-thawed semen;
    incubating sperm cells contained within said frozen-thawed semen in a concentration of Hoechst 33342 stain of greater than 40 micro-molar;
    establishing the temperature at which said sperm cells are incubated between about 30 degrees centigrade and about 40 degrees centigrade;
    adjusting a duration of time said sperm cells are incubated in said concentration of Hoechst 33342 stain;
    staining said sperm cells with sufficient uniformity to allow X-chromosome bearing sperm cells to be differentiated from Y-chromosome bearing sperm cells based upon the magnitude of fluorescence;
    determining the sex characteristic of a plurality of sperm cells contained within said frozen-thawed semen;
    separating said sperm cells according to the determination of their sex characteristic;
    isolating sperm cells separated according to the determination of their sex in a collection element;
    establishing a sample from said sperm cells isolated in said collection element;
    wherein fertilizing at least one egg of a female mammal with said sample at success levels of at least about 70% of success with spermatozoa that have not been separated and/or frozen is achieved.

2. The process of claim 1, wherein the sperm cells isolated in said collection element comprises spermatozoa sorted into separate populations, wherein the spermatozoa of one of the populations comprises at least about 85% X chromosome bearing sperm cells or at least about 85% Y chromosome bearing sperm cells.

3. The process of claim 1, wherein the sperm cells isolated in said collection element comprises spermatozoa sorted into separate populations, wherein the spermatozoa of one of the populations comprises at least about 90% X chromosome bearing sperm cells or at least about 90% Y chromosome bearing sperm cells.

4. The process of claim 1, wherein the sperm cells isolated in said collection element comprises spermatozoa sorted into separate populations, wherein the spermatozoa of one of the populations comprises at least about 95% X chromosome bearing sperm cells or at least about 95% Y chromosome bearing sperm cells.

5. The process of claim 1, wherein said male mammal is selected from the group of mammals consisting of primates, humans, swine, ovids, bovids, equids, canids, felids, and dolphins.

6. The process of claim 1, wherein said step of staining DNA within said sperm cells with a concentration of Hoechst 33342 greater than 40 micro-molar comprises staining of sufficient uniformity to allow X-chromosome bearing sperm cells to be differentiated from Y-chromosome bearing sperm cells based upon the magnitude of fluorescence at a rate of up to about 95%.

7. The process of claim 6, wherein said step of staining DNA within said sperm cells with sufficient uniformity to allow X-chromosome bearing sperm cells to be differentiated from Y-chromosome bearing sperm cells based upon the magnitude of fluorescence at a purity of up to about 95% comprises differentiating said magnitude of fluorescence with a flow cytometer.

8. The process of claim 7, wherein said step of isolating sperm cells separated according to the determination of their sex in a collection element comprises isolating Y-chromosome bearing sperm cells into a separate collection element at a rate selected from a group consisting of about 1000 per second, and about 2000 per second.

9. The process of claim 7, wherein said step of isolating sperm cells separated according to the determination of their sex in a collection element comprises isolating X-chromosome bearing sperm cells into a separate collection element at a rate selected from a group consisting of about 1000 per second, and about 2000 per second.

10. The process of claim 1, wherein said male mammal is a bovid, and wherein said concentration of Hoechst 33342 stain is between about 200 micro-molar and about 2500 micro-molar.

11. The process of claim 10, wherein said male mammal is a bovid, and wherein said concentration of Hoechst 33342 stain is 224 micro-molar.

12. The process of claim 10, wherein said male mammal is a bovid and wherein said concentration of Hoechst 3342 stain is 2240 micro-molar.

13. The process of claim 10, further comprising the step of adjusting a duration of time said sperm cells are incubated with said concentration of Hoechst 33342 stain between about 50 minutes and about 200 minutes.

14. The process of claim 1, further comprising the step of limiting the number of isolated sperm cells in said sample to about 10% to about 50% of the number of said sperm cells relative to a typical unseparated artificial insemination sample.

15. The process of claim 1, wherein said sample has the number of isolated sperm cells limited to about one million to three million.

16. The process of claim 1, wherein said sample has the of number isolated sperm cells limited to between about one-hundred and fifty thousand and about one million.

17. The process of claim 1, wherein said sample has the number of isolated sperm cells limited to between about forty million and about one hundred million.

18. The process of claim 1, wherein said step of establishing said sample from said sperm cells isolated in said collection element comprises the step of establishing an in-vitro fertilization sample from said sperm cells isolated in said collection element.

19. The process of claim 1, wherein said step of establishing said sample from said sperm cells isolated in said collection element comprises the step of establishing an artificial insemination sample from said sperm cells isolated in said collection element.

20. A process for preparing sperm cell samples, the process comprising:

collecting semen from a male mammal;
  freezing said semen to form frozen semen;
  thawing said frozen semen to form frozen-thawed semen;
  incubating sperm cells contained within said frozen-thawed semen in a concentration of Hoechst 33342 stain of greater than 40 micro-molar;
  establishing the temperature at which said sperm cells are incubated between about 30 degrees centigrade and about 40 degrees centigrade;
  adjusting a duration of time said sperm cells are incubated in said concentration of Hoechst 33342 stain;
  staining said sperm cells with sufficient uniformity to allow X-chromosome bearing sperm cells to be differentiated from Y-chromosome bearing sperm cells based upon the magnitude of fluorescence;
  determining the sex characteristic of a plurality of sperm cells contained within said frozen-thawed semen;
  separating said sperm cells according to the determination of their sex characteristic;
  isolating sperm cells separated according to the determination of their sex in a collection element, wherein the sperms cells are stained with sufficient uniformity to produce a population of either X-chromosome bearing sperm cells or Y-chromosome bearing sperm cells with a rate of between about 85% and about 95%;
  establishing a sample from said sperm cells isolated in said collection element; wherein fertilizing at least one egg of a female mammal with said sample at success levels of at least about 70% of success with spermatozoa that have not been separated and/or frozen is achieved.

* * * * *